US012661234B2

(12) United States Patent (10) Patent No.: US 12,661,234 B2
Moses et al. (45) Date of Patent: Jun. 23, 2026

(54) PIEZOELECTRIC SPINAL IMPLANT AND METHODS OF MAKING AND USING SAME

(71) Applicant: Spark Assets LLC, Needham, MA (US)

(72) Inventors: Ziev Moses, Needham, MA (US); Kevin Chappuis, Saugus, MA (US); Luke Diehl, Medford, MA (US); Lance Smith, Edmond, OK (US)

(73) Assignee: Spark Assets LLC, Needham, MA (US)

( * ) Notice: Subject to any disclaimer, the term of this patent is extended or adjusted under 35 U.S.C. 154(b) by 144 days.

(21) Appl. No.: 18/308,406

(22) Filed: Apr. 27, 2023

(65) Prior Publication Data

US 2023/0346568 A1 Nov. 2, 2023

Related U.S. Application Data

(60) Provisional application No. 63/335,343, filed on Apr. 27, 2022.

(51) Int. Cl.
*A61F 2/44* (2006.01)
*A61F 2/30* (2006.01)
(52) U.S. Cl.
CPC .... *A61F 2/442* (2013.01); *A61F 2002/30087* (2013.01); *A61F 2002/30904* (2013.01);
(Continued)
(58) Field of Classification Search
CPC .................... A61F 2/442; A61F 2/4425; A61F 2002/30136
See application file for complete search history.

(56) References Cited

U.S. PATENT DOCUMENTS

| | | | |
|---|---|---|---|
| 5,057,111 A | 10/1991 | Park | |
| 5,797,912 A | 8/1998 | Runciman et al. | |

(Continued)

FOREIGN PATENT DOCUMENTS

| | | |
|---|---|---|
| CN | 114401684 A | 4/2022 |
| CN | 116473649 A | 7/2023 |

(Continued)

OTHER PUBLICATIONS

United States Patent and Trademark Office, International Search Report and the Written Opinion of the International Searching Authority, or the Declaration, issued in International Patent Application No. PCT/US2023/020201, dated Jul. 21, 2023, 18 pages.

(Continued)

*Primary Examiner* — Jan Christopher L Merene
(74) *Attorney, Agent, or Firm* — Alliance IP, LLC

(57) ABSTRACT

A spinal implant capable of generating an electric output includes a first endplate, a second endplate, and a piezoelectric component disposed between the first and second endplates. The spinal implant may further include an intermediate body and a second piezoelectric component disposed between the intermediate body and the second endplate. The inner surfaces of the endplates and/or the intermediate body may be non-planar, such as having an undulating shape. The electric output is produced when the endplates of the spinal implant undergo a force, including a compressive force and/or a shear force.

32 Claims, 61 Drawing Sheets

(52) U.S. Cl.
CPC ................. *A61F 2250/0018* (2013.01); *A61F 2310/00023* (2013.01)

(56) References Cited

U.S. PATENT DOCUMENTS

| | | | |
|---|---|---|---|
| 6,034,296 | A | 3/2000 | Elvin et al. |
| 6,290,724 | B1* | 9/2001 | Marino ................. A61F 2/4611 |
| | | | 623/17.11 |
| 7,431,734 | B2 | 10/2008 | Danoff et al. |
| 7,766,947 | B2 | 8/2010 | Hawkes et al. |
| 7,862,597 | B2 | 1/2011 | Gause et al. |
| 8,083,741 | B2 | 12/2011 | Morgan et al. |
| 8,551,092 | B2 | 10/2013 | Morgan et al. |
| 2002/0062153 | A1* | 5/2002 | Paul .................... A61F 2/30942 |
| | | | 623/17.11 |
| 2003/0135275 | A1 | 7/2003 | Garcia et al. |
| 2004/0049270 | A1* | 3/2004 | Gewirtz ................... A61F 2/28 |
| | | | 606/247 |
| 2005/0228503 | A1 | 10/2005 | Gundolf |
| 2005/0273170 | A1* | 12/2005 | Navarro ................. A61F 2/442 |
| | | | 600/595 |
| 2006/0052782 | A1 | 3/2006 | Morgan et al. |
| 2006/0116678 | A1 | 6/2006 | Impellizzeri |
| 2006/0190080 | A1 | 8/2006 | Danoff et al. |
| 2006/0259143 | A1 | 11/2006 | Navarro et al. |
| 2008/0177330 | A1 | 7/2008 | Ralph et al. |
| 2009/0182432 | A1 | 7/2009 | Zdeblick et al. |
| 2009/0198284 | A1 | 8/2009 | Henry |
| 2011/0015682 | A1 | 1/2011 | Lewis et al. |
| 2011/0118852 | A1 | 5/2011 | Evans |
| 2011/0224737 | A1 | 9/2011 | Lewis et al. |
| 2013/0052254 | A1 | 2/2013 | Arinzeh et al. |
| 2013/0304211 | A1* | 11/2013 | Trautwein ............... A61L 27/04 |
| | | | 623/17.15 |
| 2013/0317615 | A1 | 11/2013 | Jimenez et al. |
| 2014/0025168 | A1 | 1/2014 | Klimek et al. |
| 2014/0094856 | A1 | 4/2014 | Sinha |
| 2015/0134061 | A1 | 5/2015 | Friis et al. |
| 2016/0135858 | A1 | 5/2016 | Dacosta et al. |
| 2016/0325241 | A1 | 11/2016 | May et al. |
| 2017/0007420 | A1* | 1/2017 | Stevenson .............. A61B 5/076 |
| 2018/0110550 | A1 | 4/2018 | Pengo |
| 2018/0132913 | A1 | 5/2018 | Davison et al. |
| 2018/0140339 | A1 | 5/2018 | Silva et al. |
| 2018/0303616 | A1* | 10/2018 | Bhattacharyya ....... B33Y 50/02 |
| 2019/0099276 | A1 | 4/2019 | Chin et al. |
| 2019/0274838 | A1 | 9/2019 | Manwill et al. |
| 2020/0129312 | A1 | 4/2020 | Donahoe et al. |
| 2020/0345399 | A1 | 11/2020 | Gregory, II et al. |
| 2021/0367134 | A1 | 11/2021 | Friis et al. |
| 2022/0015811 | A1 | 1/2022 | Lopez Camacho et al. |
| 2022/0339429 | A1 | 10/2022 | Li et al. |
| 2023/0029611 | A1* | 2/2023 | Shanks ............... A61F 2/30771 |
| 2023/0346437 | A1 | 11/2023 | Moses et al. |
| 2023/0414365 | A1* | 12/2023 | Davis ........................ A61F 2/28 |
| 2024/0058504 | A1* | 2/2024 | Johnson ............... H10N 30/857 |
| 2025/0018181 | A1* | 1/2025 | Moses .................. A61F 2/4455 |

FOREIGN PATENT DOCUMENTS

| | | | |
|---|---|---|---|
| EP | 1023872 | A2 | 8/2000 |
| WO | 2005120203 | A2 | 12/2005 |
| WO | 2006084239 | A2 | 8/2006 |
| WO | 2017062399 | A1 | 4/2017 |
| WO | 2020231929 | A1 | 11/2020 |
| WO | 2021052356 | | 3/2021 |
| WO | 2022015696 | A2 | 1/2022 |

OTHER PUBLICATIONS

U.S. Patent and Trademark Office, International Search Report and the Written Opinion of the International Searching Authority, or the Declaration, issued in International Patent Application No. PCT/US2023/020208, dated Nov. 6, 2023, 18 pages.

USPTO; Non-Final Office Action issued in U.S. Appl. No. 18/308,455, dated Nov. 18, 2025; 16 pages.

EPO; Extended European Search Report issued for EP Patent Application No. 23797281.5 dated Mar. 19, 2026; 15 pages.

EPO; Extended European Search Report issued in EP Patent Application No. 23797284.9, dated Mar. 9, 2026; 8 pages.

* cited by examiner

600

606

602

604

608

1602

1608

1602

Force sensor readout

3100

3102

3106

3108

3104

3106

3110

3112

3104

3402

3402

3402

3402

4100

4102

4104

4104

4100

4502

4504

4502

4504

4802

4802

4902

4902

PIEZOELECTRIC SPINAL IMPLANT AND METHODS OF MAKING AND USING SAME

CROSS-REFERENCE TO RELATED APPLICATIONS

This application claims priority from U.S. Provisional Patent Application 63/335,343, filed Apr. 27, 2022, which is hereby incorporated herein by reference in its entirety.

FIELD OF THE INVENTION

The present application relates to spinal implants comprising piezoelectric material capable of stimulating bone and tissue growth around the implant. Specifically, the application relates to a spinal implant having piezoelectric properties capable of generating an electric charge on its surface, leading to enhanced bone growth around the cage. The electrical output from the piezoelectric material may be produced by fluctuations of an applied mechanical load.

BACKGROUND OF THE INVENTION

Electrical stimulation has long been used to stimulate bone growth and promote fusion after spinal implant surgery. If, after a period of recovery, a patient does not naturally generate the type of growth anticipated by their physician, a second surgery may be required to place an electrical implant and associated battery under the skin, with a cathode running to the area of fusion around the bone. This type of treatment is generally only used as a secondary means of stimulating bone growth given its invasive nature and need for additional surgery.

Alternatively, patients may be instructed to wear a non-invasive vest or harness or to apply small skin pads/electrodes that are capable of generating a weak electrical current within the target sight using either pulsed electromagnetic fields, capacitive coupling, or combined magnetic fields. However, there is limited data evidencing the effectiveness of this type of noninvasive treatment.

SUMMARY OF THE INVENTION

In accordance with one embodiment of the invention, a spinal implant capable of generating an electric output includes a first endplate with an inner surface, a second endplate with an inner surface, and a first piezoelectric component disposed between the inner surfaces of the first endplate and the second endplate. The piezoelectric component has a non-planar shape when a force is applied to the first and second endplates.

In an embodiment, the inner surfaces of the first and second endplates may be non-planar. For example, they may be undulating. The piezoelectric component may have an upper surface that conforms to the inner surface of the first endplate and a lower surface that conforms to the inner surface of the second endplate. The force may be an assembly force, and/or it may be a spinal compression force. The force may be between 25 N and 10,000 N.

In accordance with another embodiment, the spinal implant may further include a second piezoelectric component disposed between the first endplate and second endplate, and an intermediate body with a non-planar top surface and a non-planar bottom surface disposed between the first piezoelectric component and the second piezoelectric component.

In accordance with related embodiments, the first piezoelectric component has an upper surface that conforms to the inner surface of the first endplate and a lower surface that conforms to the top surface of the intermediate body. The second piezoelectric component may have an upper surface that conforms to the bottom surface of the intermediate body and a lower surface that conforms to the inner surface of the second endplate.

In related embodiments, the intermediate body may be an insulator. The first and second endplates may be conductive and further comprise a plurality of conductive jumpers disposed through the intermediate body. One end of each jumper may be connected to a surface of a piezoelectric component and the other end of each jumper may be flush with an exterior surface of the intermediate body.

In related embodiments the spinal implant may comprise at least one connecting component affixed to both the first and second endplate, the connecting component acting as an insulator, wherein the intermediate body acts as a conductor.

In one or more embodiments, the first and second endplates have outer surface textures that are uneven. The piezoelectric component or components may include a plurality of distinct layers, with at least one of the layers being piezoelectric. There may additionally be at least one layer that is non-piezoelectric.

In accordance with an embodiment the first and second endplates have outer surfaces and the piezoelectric component is configured to produce an electrical output corresponding to a load applied to the outer surfaces of the first and second endplates.

An embodiment of a method of using the spinal implant may include attaching the first endplate to a first vertebra and a second endplate to a second vertebra.

An embodiment of a spinal implant capable of generating an electric output includes a first endplate with a non-planar inner surface, a second endplate with a non-planar inner surface, and a first piezoelectric component disposed between the inner surfaces of the first endplate and the second endplate.

Another embodiment of a spinal implant capable of generating an electric output includes a first endplate with an inner surface, a second endplate with an inner surface, a first piezoelectric component disposed between the inner surfaces of the first endplate and the second endplate, and an intermediate body having a structural geometry that distributes compressive forces applied to the endplates unevenly to the piezoelectric material. In a related embodiment, the structural geometry may be a variation in material stiffness and/or material shape.

BRIEF DESCRIPTION OF THE FIGURES

Further embodiments of the present application can be understood with reference to the appended figures.

DETAILED DESCRIPTION OF THE INVENTION

Figure 1:
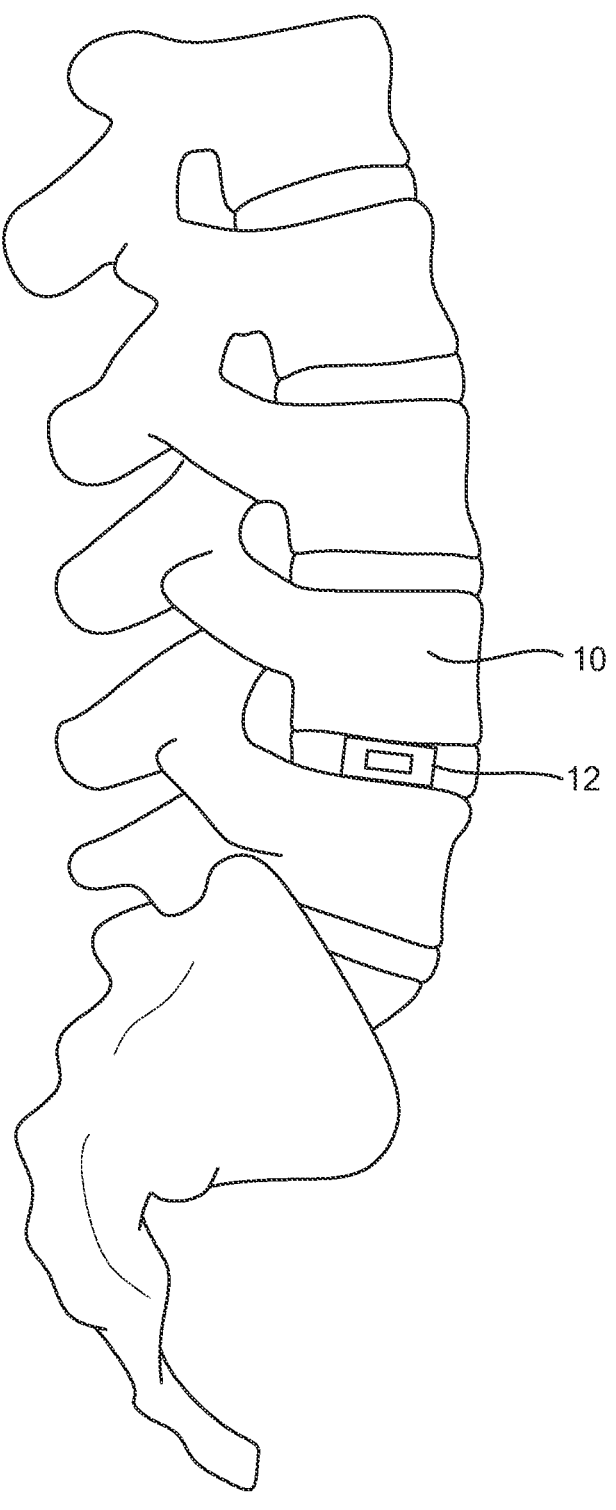
FIG. 1 is a side view of a piezoelectric spinal implant disposed between two vertebrae of a spinal column, in accordance with an embodiment of the invention.

A spinal implant capable of generating an electrical current is provided. As shown in FIG. 1, a spinal implant 10 may include piezoelectric material, which generates an electrical charge as pressure is applied thereto in order to facilitate tissue stimulation and promote fusion of the implant 10 to the surrounding vertebrae 12. As will be shown with reference to FIGS. 2-50, the design of the implant may include various embodiments, each generally including an upper and lower endplate 14, 16, a cage body (i.e., intermediate body) 18, and a piezoelectric material component 20.

Before explaining at least one aspect of the disclosed and/or claimed inventive concept(s) in detail, it is to be understood that the disclosed and/or claimed inventive concept(s) is not limited in its application to the details of construction and the arrangement of the components or steps or methodologies set forth in the following description or illustrated in the drawings. The disclosed and/or claimed inventive concept(s) is capable of other aspects or of being practiced or carried out in various ways. Various embodiments containing different features and aspects are shown in this disclosure. It should be understood that other embodiments containing some of these features and aspects, and other features and aspects known in the art, are within the scope of this disclosure, even if such an exact combination is not shown or described specifically. Also, it is to be understood that the phraseology and terminology employed herein is for the purpose of description and should not be regarded as limiting.

As utilized in accordance with the disclosure, the following terms, unless otherwise indicated, shall be understood to have the following meanings.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

The singular forms "a," "an," and "the" include plural forms unless the context clearly dictates otherwise specified or clearly implied to the contrary by the context in which the reference is made. The term "Comprising" and "Comprises of" includes the more restrictive claims such as "Consisting essentially of" and "Consisting of".

For purposes of the following detailed description, other than in any operating examples, or where otherwise indicated, numbers that express, for example, quantities of ingredients used in the specification and claims are to be understood as being modified in all instances by the term "about". The numerical parameters set forth in the specification and attached claims are approximations that may vary depending upon the desired properties to be obtained in carrying out the invention.

All percentages, parts, proportions, and ratios as used herein, are by weight of the total composition, unless otherwise specified. All such weights as they pertain to listed ingredients are based on the active level and, therefore; do not include solvents or by-products that may be included in commercially available materials, unless otherwise specified.

All publications, articles, papers, patents, patent publications, and other references cited herein are hereby incorporated herein in their entirety for all purposes to the extent consistent with the disclosure herein.

The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "each independently selected from the group consisting of" means when a group appears more than once in a structure, that group may be selected independently each time it appears.

As shown in FIGS. 2-50, the spinal implant 12 may include many different embodiments. For the purpose of illustration, FIGS. 2a-i will be referred to in detail. However, it should be understood that the embodiments disclosed in FIGS. 3-50 may include the same or similar elements, and may include various additional components.

Figures 2A, 2B, 2C, 2D:
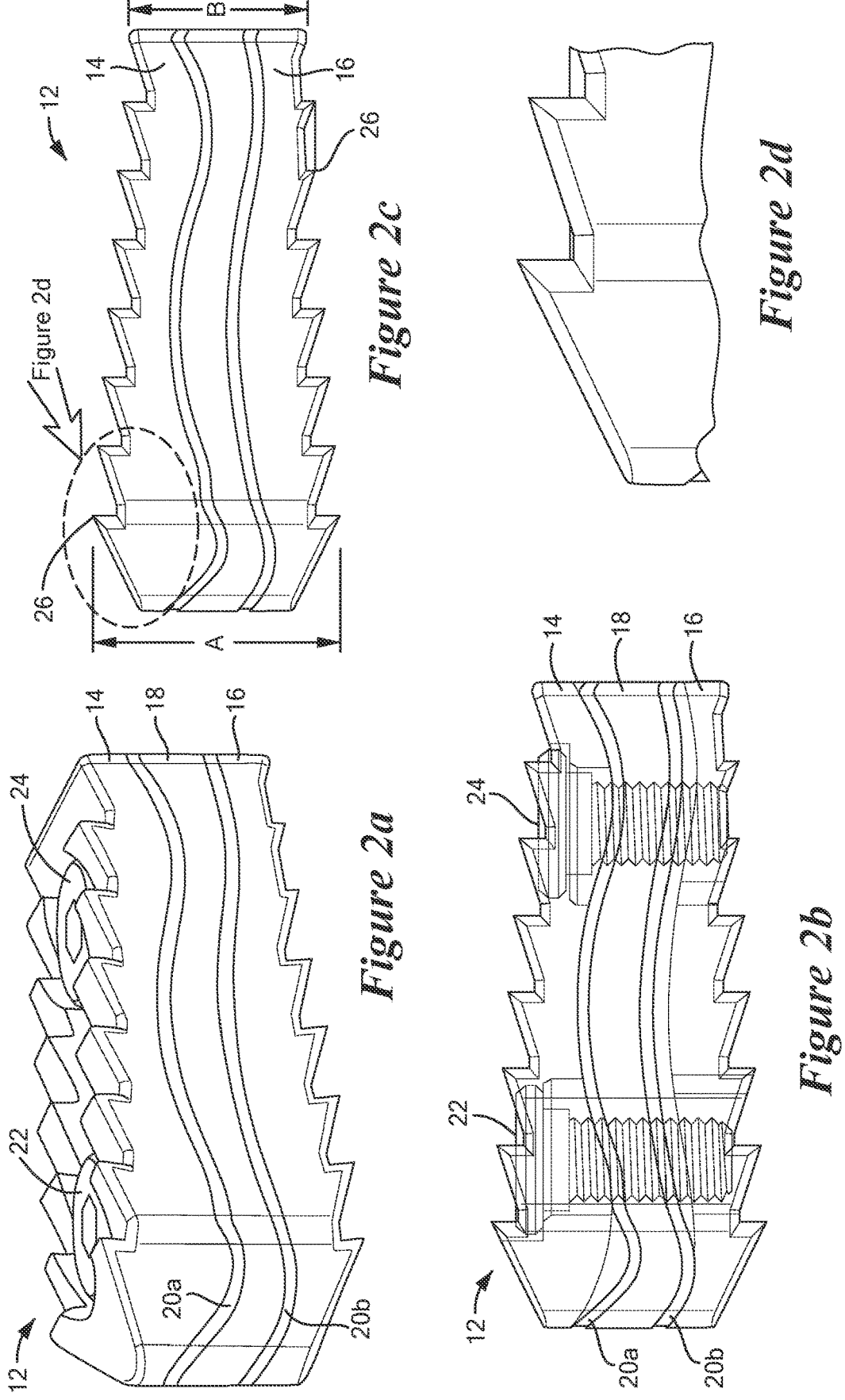
FIG. 2a is a front perspective view of one embodiment of the piezoelectric spinal implant with layers described as top and bottom endplates used to anchor the implant to opposing bony surfaces, piezoelectric components such as PVDF that can create an electric output when loaded or strained, and a middle layer that can be made from an electrically conductive or insulating material.
FIG. 2b is a partially transparent side view of the embodiment of FIG. 2a showing lag screws used to assemble the implant and without shielding forces applied in the compression direction.
FIG. 2c is a side view of the embodiment of FIG. 2*a*.
FIG. 2*d* is a detail view of a portion of FIG. 2*c*.

Referring now to FIG. 2a, a piezoelectric spinal implant 12 may include an upper endplate 14, a lower endplate 16, a cage body 18, and at least one layer of piezoelectric material 20. In this embodiment, the implant 12 includes a first and second layer of piezoelectric material 20a and 20b disposed above and below the cage body 18, which may be referred to herein as an intermediate body or middle layer. The top and bottom endplates 14 and 16 may be used to engage and/or anchor the implant to opposing bony surfaces, such as vertebrae. The piezoelectric components 20a and 20b may create an electric output when loaded or strained, and the cage body can be made from an electrically conductive or insulating material. In this embodiment, the components of the implant 12 may be joined together using a set of tantalum or titanium screws 22 and 24, which are excellent conductors, and which are disposed vertically through the layers of the implant 12, as shown in FIG. 2b.

It should be understood that the components may be adjoined using any suitable material, structure, or method, such as a tantalum rod (see embodiments of FIGS. 3, 4, and 5), 3D printing (FIGS. 10, 11, and 12), saturation or dispersion (FIG. 7), coating (FIG. 8), rivets (embodiment of FIG. 9), adhesive (FIGS. 14, 17, 18, 21), friction fit (FIGS. 13, 15, 19, 20), swing lock (FIG. 16), or a combination thereof (FIG. 6).

Referring now to FIGS. 2c and d, the upper endplate 14 and the lower endplate 16 are typically made of titanium, or other suitable material, such as polyether ether ketone (PEEK), carbon-ceramic composite, tantalum, silicon nitride or other biocompatible materials. It should be understood that the material used for the upper and lower endplates may have varying conductive qualities. However, one of ordinary skill in the art would understand that the materials of the endplates, and of the cage body, should have sufficient conductive and insulative qualities to promote the transference of the electrical charge produced by the piezoelectric material to the bone surrounding the implant itself.

The endplates may include a plurality of teeth 26, ranging from 0.5 mm to 2 mm in height, and protruding vertically from an outer surface of the plates. The teeth 26 are generally configured to engage the vertebrae 10 of the spinal column, thereby affixing or securing the implant 12 to the vertebrae from the top and bottom of the implant 12. In another embodiment, the implant 12 may be configured to include piezoelectric wings 28 that are configured to extend through the cage body 18 and be affixed within the vertebrae, as shown in FIG. 22.

As shown in FIG. 2c, the endplates 14 and 16 may be configured to decrease in height along a vertical direction at an angle of about 0° to 25°, measured from the first tooth of the implant to the last, such that the front portion (A) of the implant is thicker than the back (B). Typically, the implant with be about 7 mm to about 15 mm from top to bottom, measured tooth to tooth, about 8 mm to about 2 mm in width, and about 22 mm to about 40 mm long. In general, the slope of the endplates is configured to match the slope and curvature of the patient's spinal column, allowing it to sit snugly within between the vertebrae.

The cage body 18 may be made of a suitable polymer material, such as PEEK, 3-D printed titanium carbon fiber, or other suitable biocompatible material capable of insulating the electrical current produced by the piezoelectric material and providing visibility for post operation evaluation.

Figure 2F:
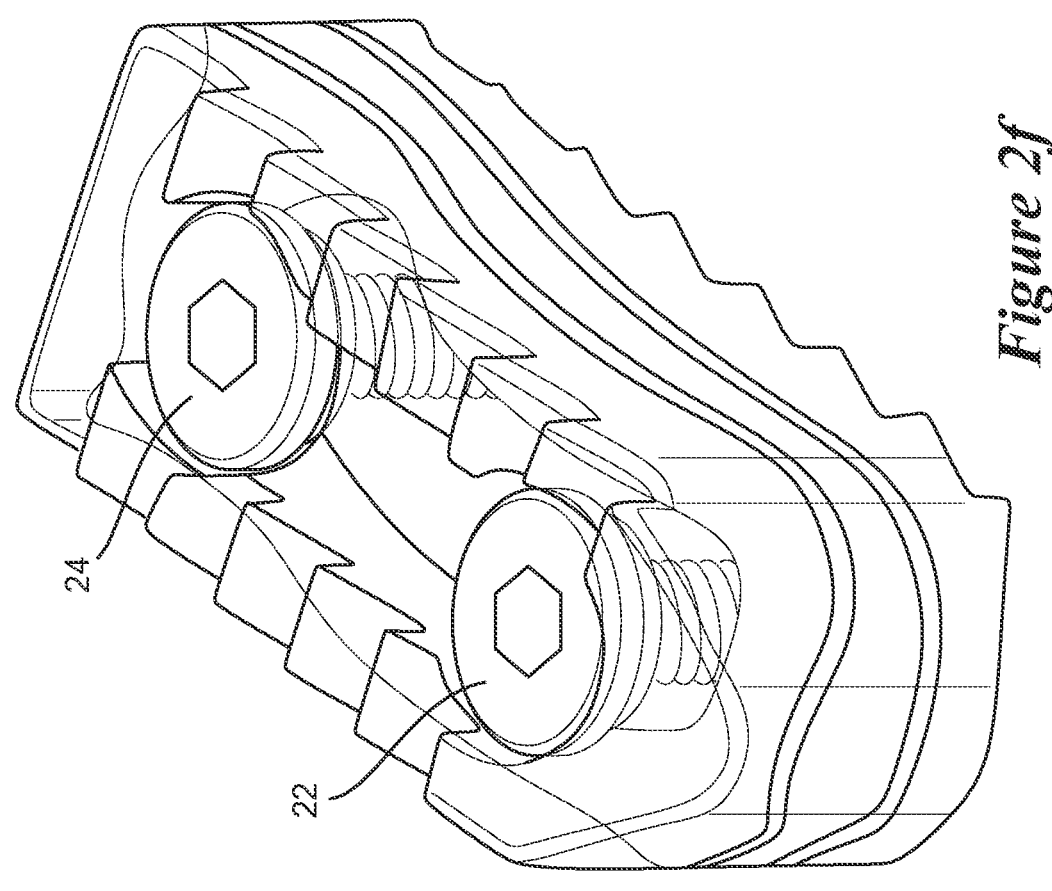
FIG. 2*f* is a partially transparent top perspective view of the embodiment of FIG. 2*a*.
Figure 2E:
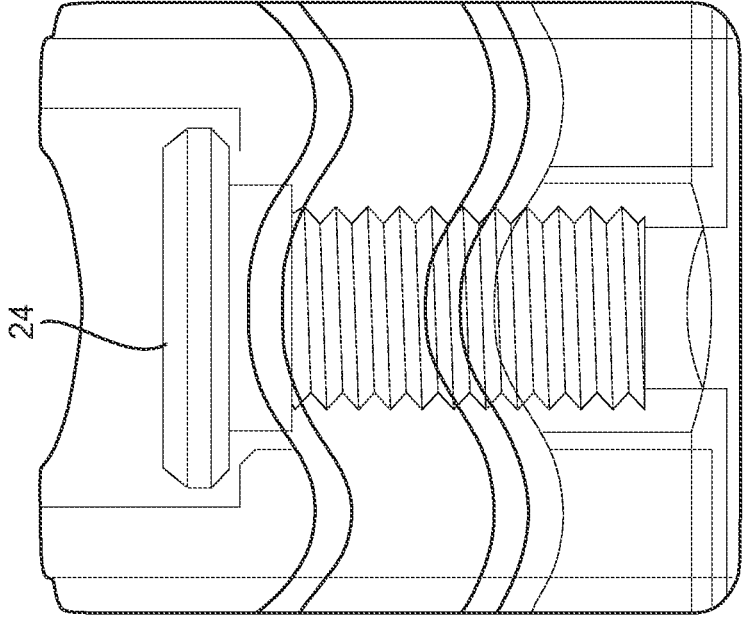
FIG. 2*e* is a partially transparent front view of the embodiment of FIG. 2*a*.
Figure 2H:
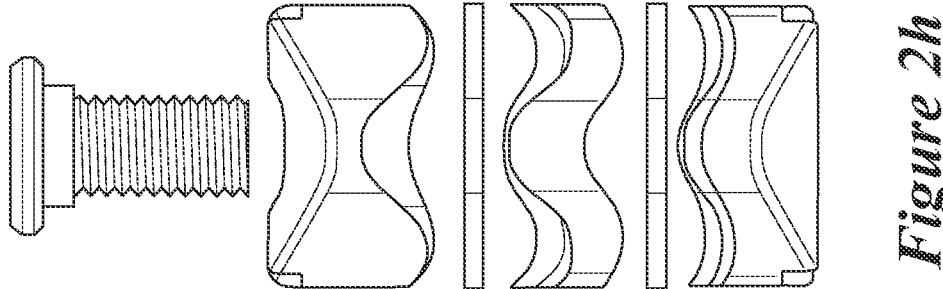
FIGS. 2*g-i* are side, front, and top perspective exploded views of the embodiment of FIG. 2*a*.
Figure 2G:
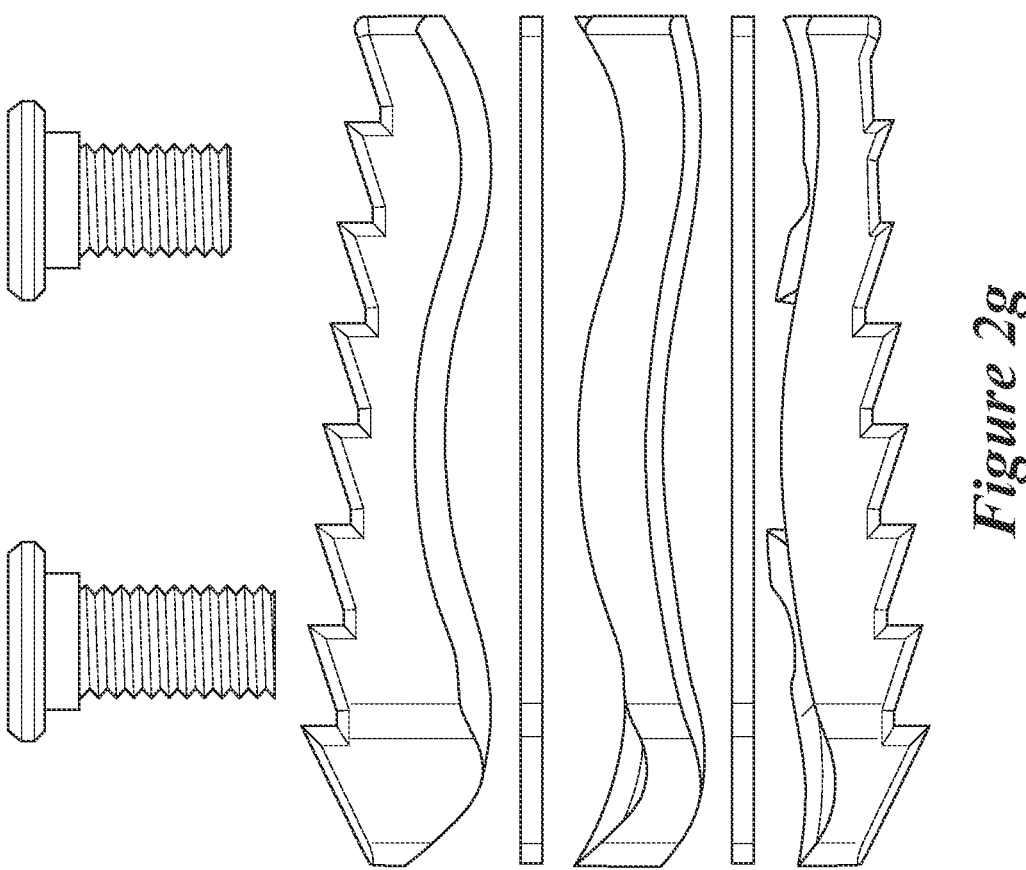
Figure 2I:
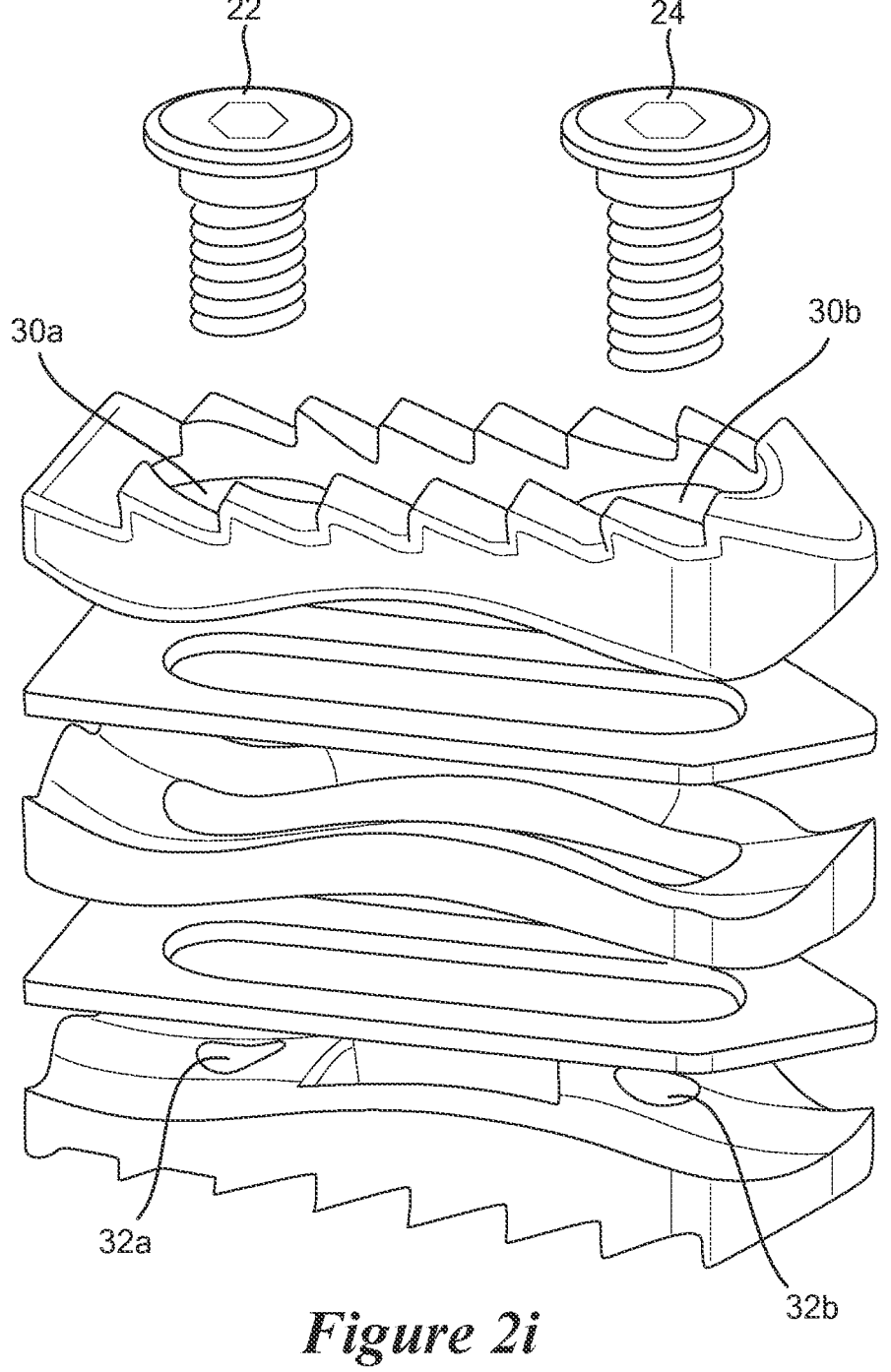
Figures 3A, 3B, 3C:
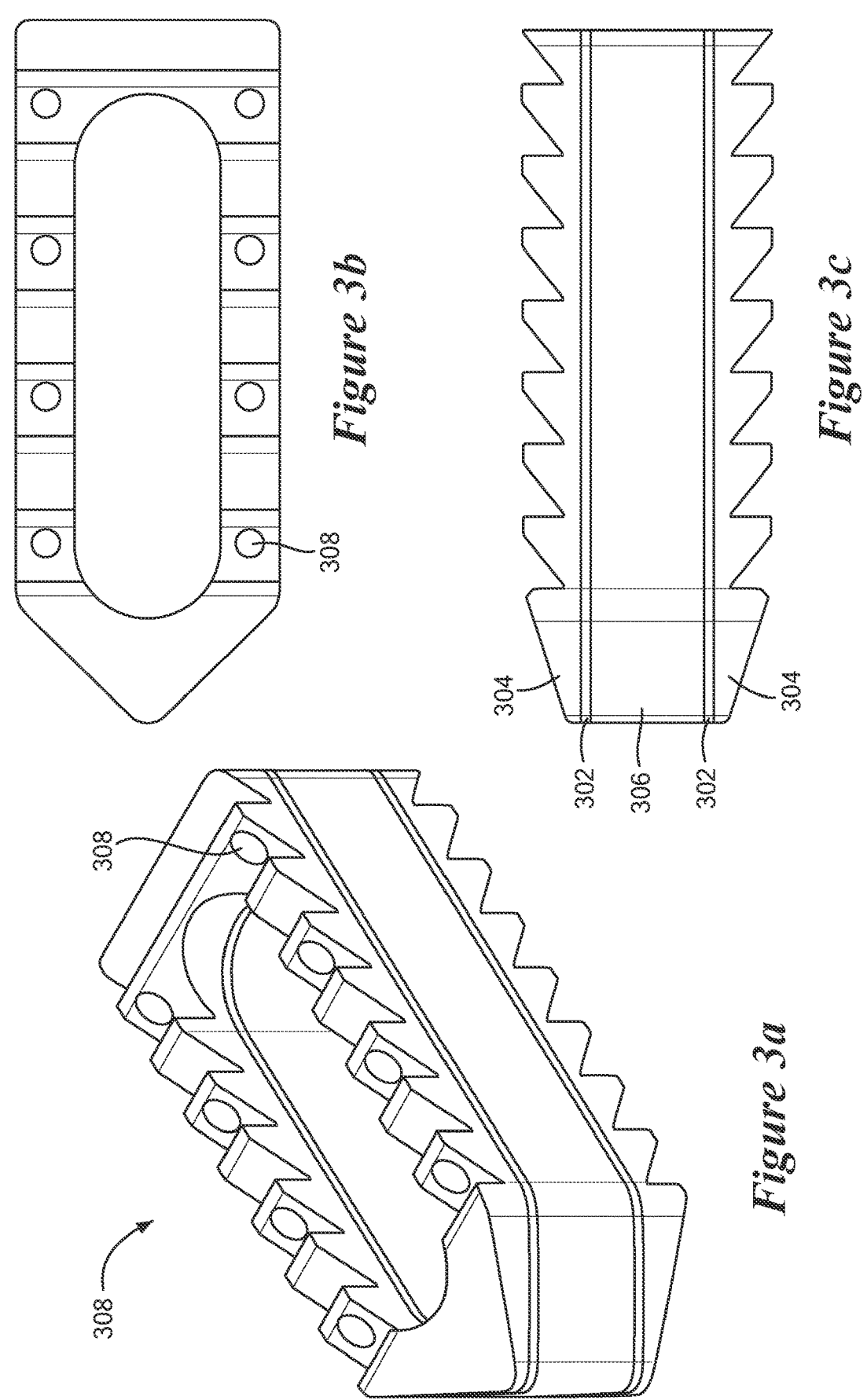
FIG. 3*a-f* are top perspective, top, side, partially transparent top perspective, bottom, and partially transparent side views of another embodiment of a piezoelectric spinal implant.
Figures 3D, 3E, 3F:
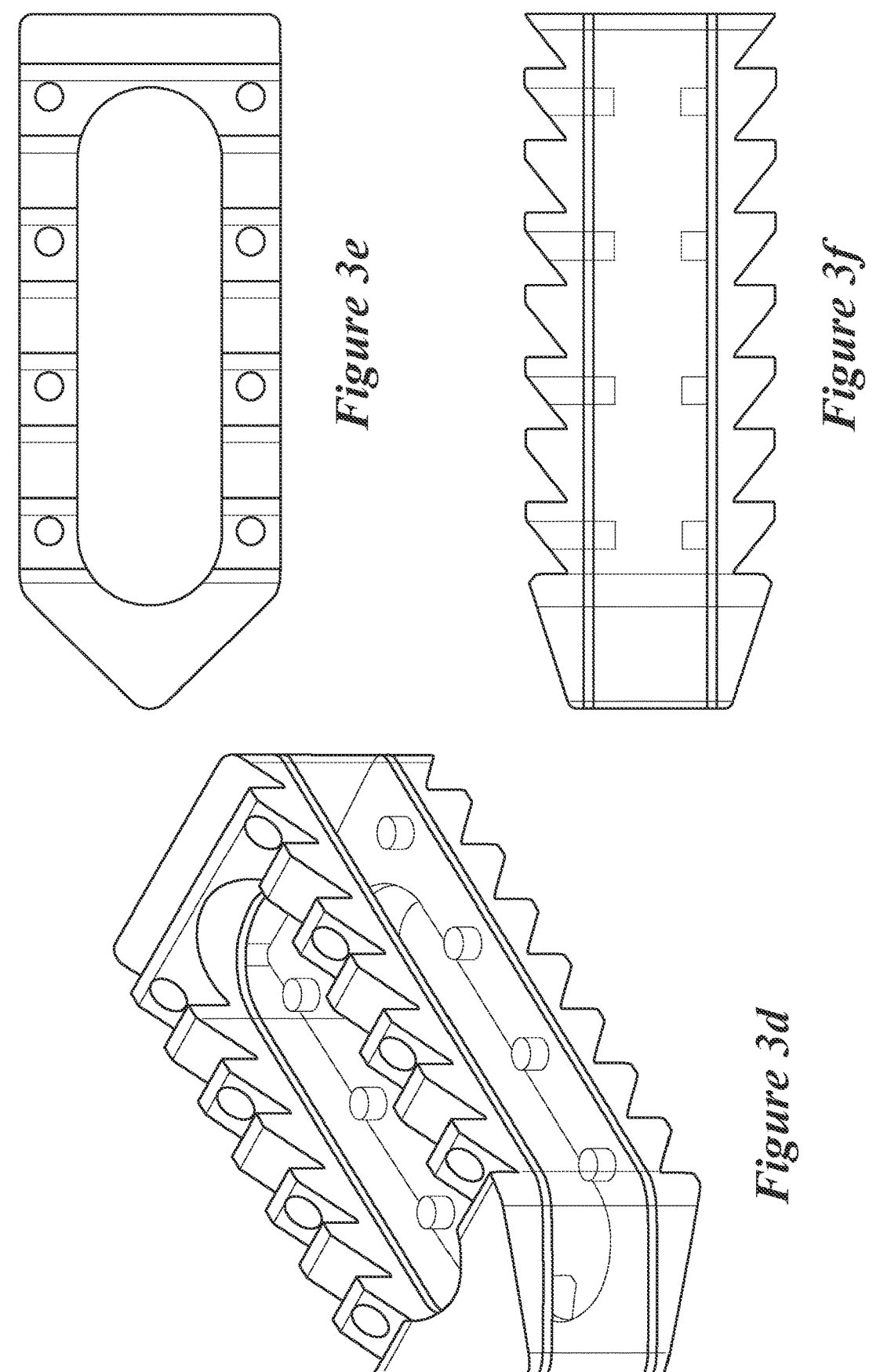

Referring now to FIGS. 2g-i, the primary components of the spinal implant 12 may have an undulating or wavy shape. As shown in FIG. 2g, the upper endplate 14 includes a plurality of teeth 26 along its upper outer surface and an undulating lower inner surface. That surface is configured to conform to the upper surface of the cage body 18, which is generally about 1 mm, at its thinnest portion, to about 10 mm, at its thickest portion. Similarly, the lower endplate 16 has a lower outer surface with a plurality of teeth 26 and an undulating upper inner surface that is configured to conform to the shape of the lower surface of the cage body 18. In this embodiment, two layers of piezoelectric material 20a and 20b, such as, without limitation, a PVDF (or polyvinylidene difluoride) film, are disposed between each endplate 14, 16 and the cage body 18. The layers 20a and 20b generally mold to the shape of the surfaces between which they are disposed and are from 25 μm-1 mm in thickness.

As shown in FIGS. 2f and 2i, the upper end lower endplates 14 and 16 are configured to include two threaded holes 30a,b and 32a,b, through which the screws 22 and 24 are placed. As the screws 22 and 24 are threaded through the holes, the heads of each screw are generally configured to sit beneath the upper surface of the endplate teeth, as shown in FIG. 2e. The area between the holes 30a,b and 32a,b, respectively, may be empty, as shown in FIG. 2i. Moreover, the piezoelectric layers 20a and b and the cage body 18 may also configured to be hollow in their centers.

FIGS. 3a-f are top perspective, top, side, partially transparent top perspective, bottom, and partially transparent side views of an embodiment of a piezoelectric spinal implant 300. This embodiment has one or more layers of piezoelectric material 302 assembled between a bone-facing endplate 304, which may be titanium, and an insulating layer 306, which may be PEEK, that is used to prevent short circuiting or offsetting positive/negative electrical output. Conductive leads such as tantalum or titanium dowels 308 can be used to contact the piezoelectric material and transfer the electrical output to the exterior of the implant.

Figure 4A:
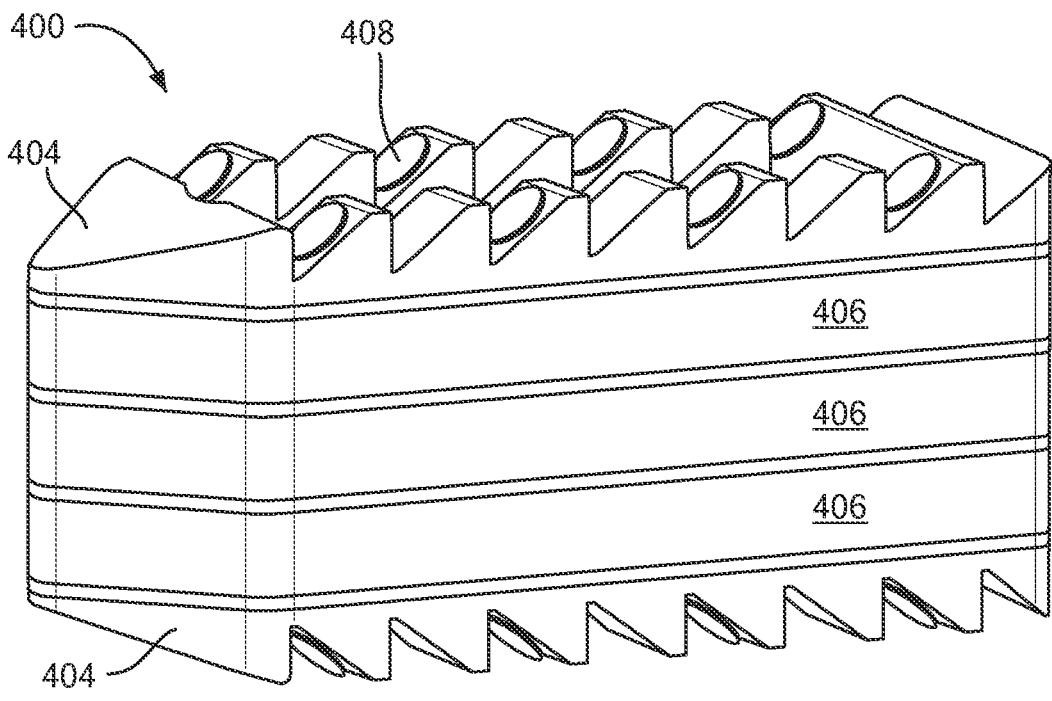
FIG. 4*a-b* are top perspective and partially transparent top perspective views of another embodiment of a piezoelectric spinal implant.
Figure 4B:
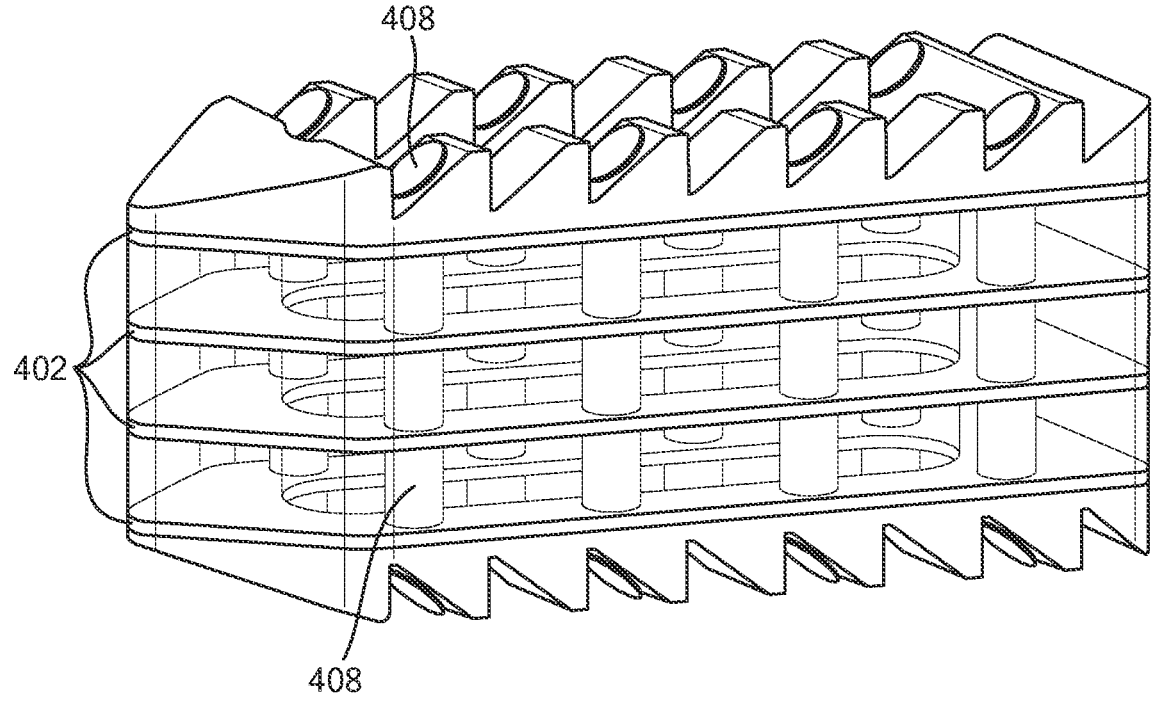

FIGS. 4a-b are top perspective and partially transparent top perspective views of an embodiment of a piezoelectric spinal implant 400. This embodiment has a multiple layers of piezoelectric material 402 assembled in series. The piezoelectric components can be assembled between bone-facing endplates 404 with or without insulating layers 406 between the piezoelectric components. Conductive leads such as tantalum dowels 408 are placed throughout the implant to carry the electrical charge from the piezoelectric components to the exterior of the implant.

Figures 5A, 5B, 5C:
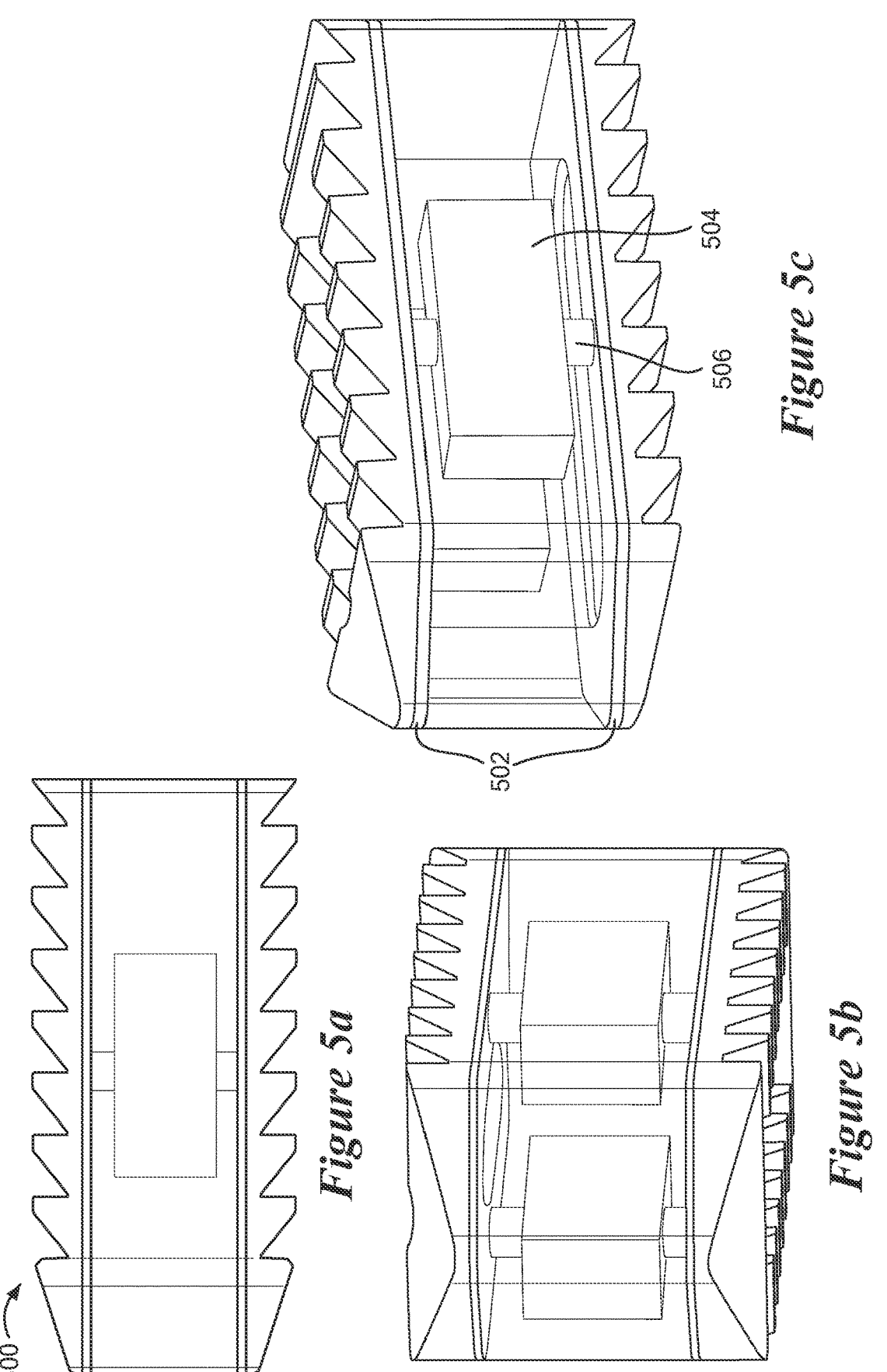
FIGS. 5*a-c* are side, partially transparent front and side perspective views of another embodiment of a piezoelectric spinal implant.

FIGS. 5a-c are side, partially transparent front and side perspective views of an embodiment of a piezoelectric spinal implant 500. This embodiment has one or more layers of piezoelectric material 502 that are connected to a conductive block 504 used to dissipate the electrical output at a focused point inside, or outside, or both sides of the implant. The conductive block can be located directly in contract with the piezoelectric material 502 or at a distance away connected by conductive leads such as tantalum dowels 506. The conductive block 504 can dissipate the electrical output through windows in the implant that expose one or more surfaces of the conductive block to the outside of the implant.

Figure 6A:
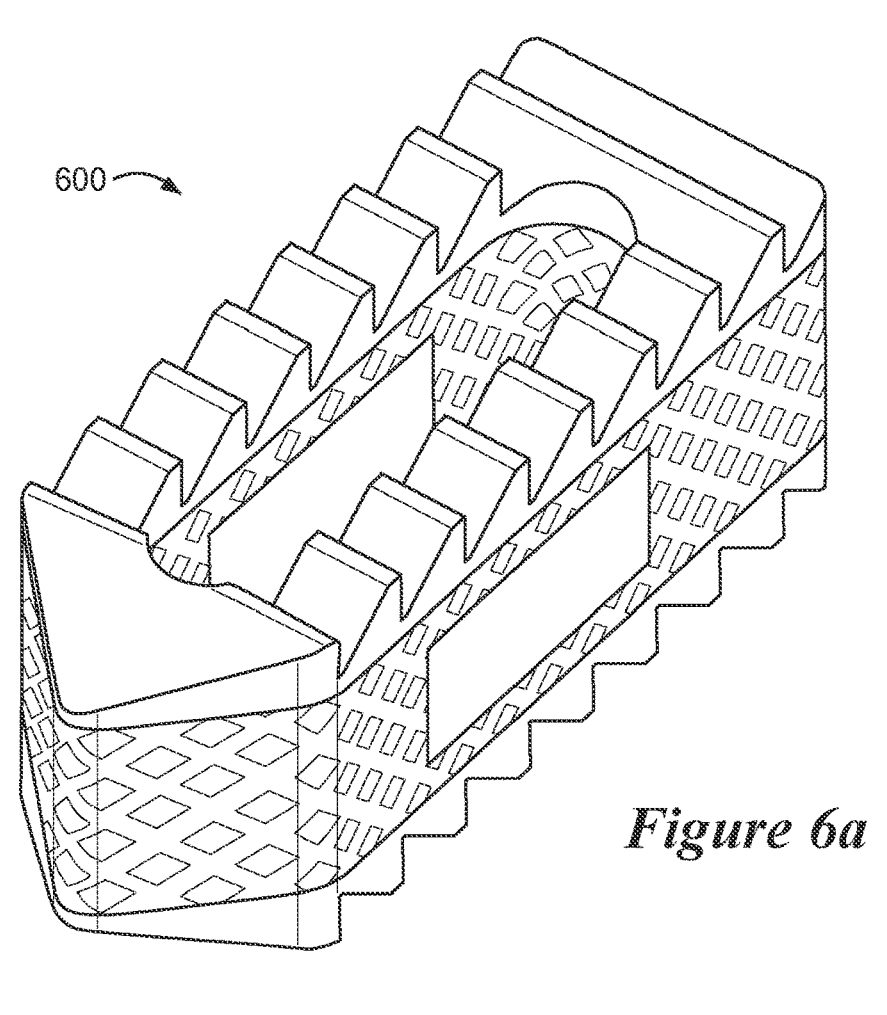
FIGS. 6*a-b* are top and side perspective views of another embodiment of a piezoelectric spinal implant.
Figure 6B:
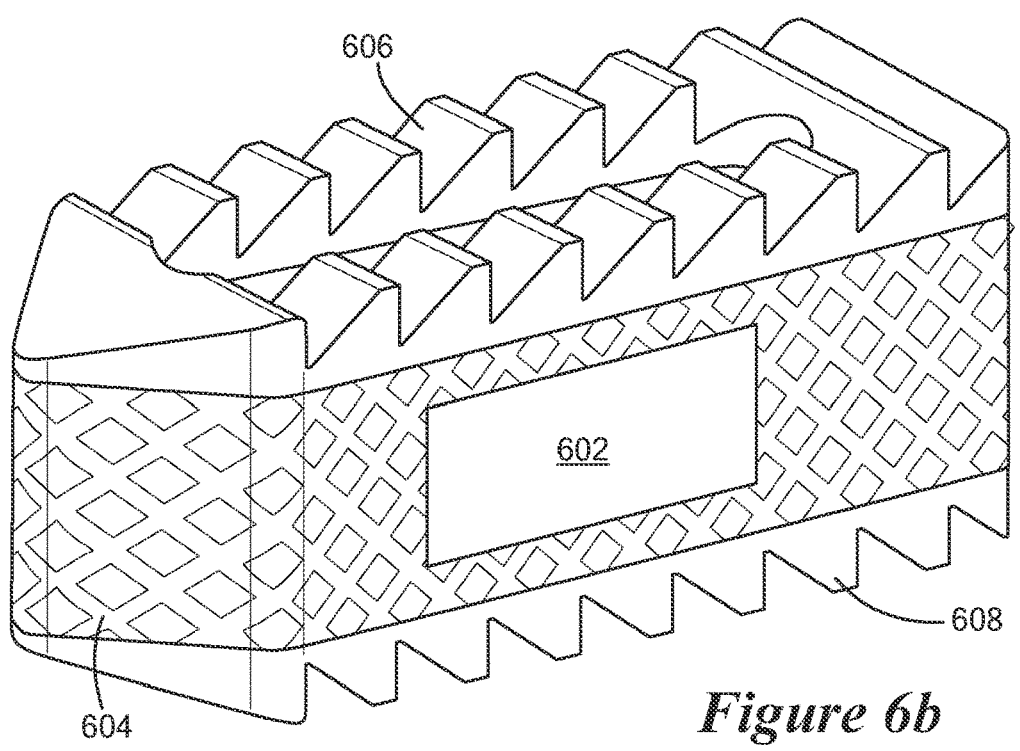

FIGS. 6a-b are top and side perspective views of an embodiment of a piezoelectric spinal implant 600. The embodiment shows an implant with a piezoelectric component 602 surrounded by a mechanical lattice or other load bearing structure that would transfer the mechanical forces from the top 606 and bottom 608 implant surfaces directly or indirectly to the piezoelectric component.

Figure 7B:
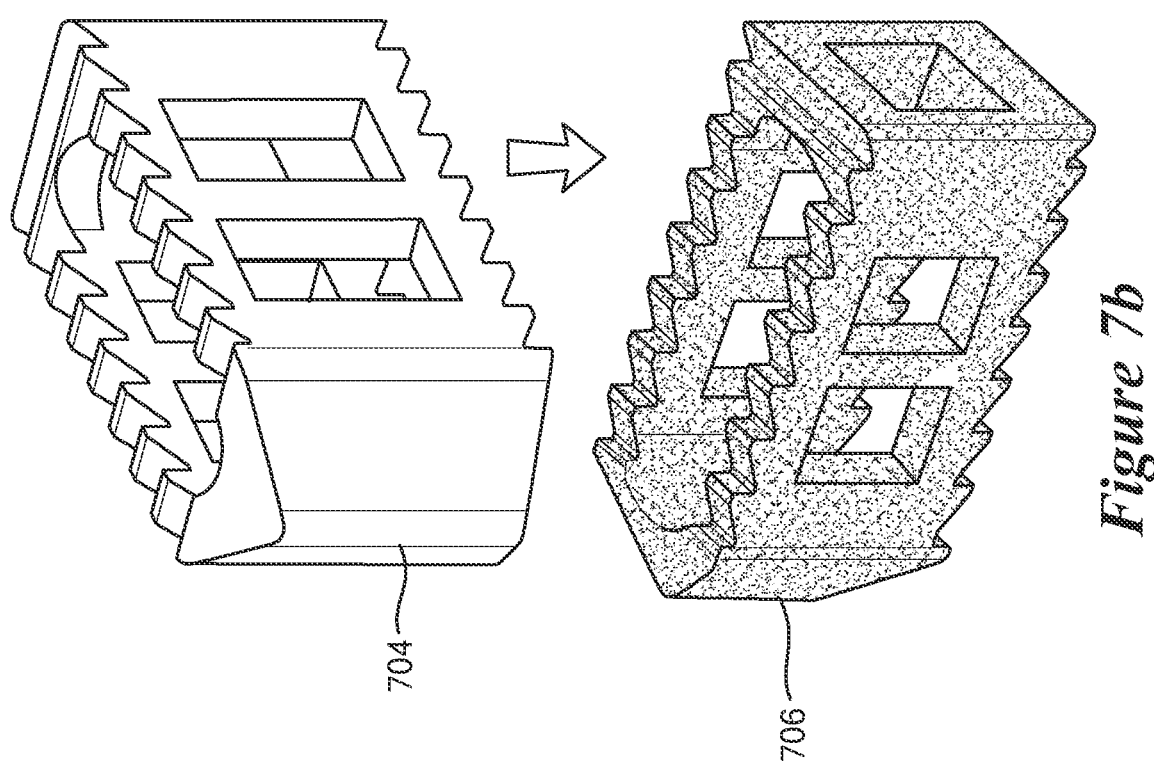
FIGS. 7*a-b* are side perspective views of another embodiment of a piezoelectric spinal implant.
Figure 7A:
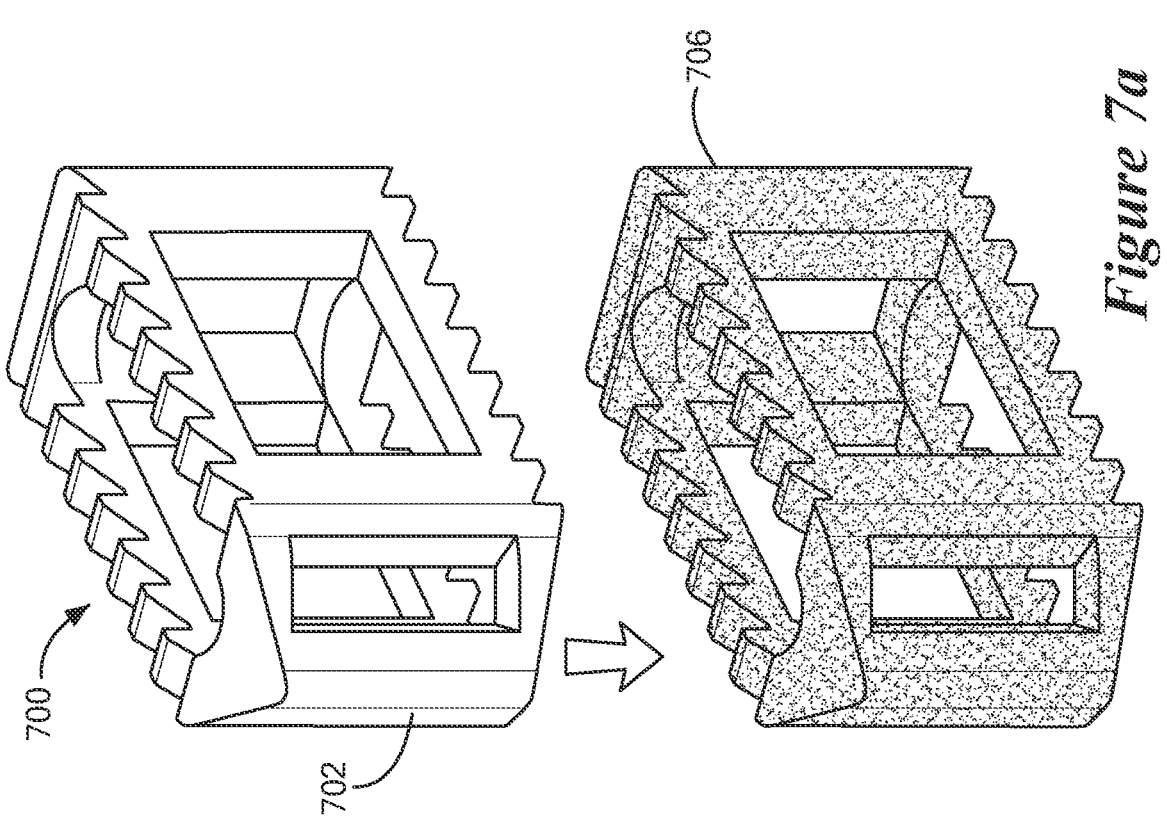

FIGS. 7a-b are side perspective views of an embodiment of a piezoelectric spinal implant 700. This embodiment shows a titanium 702 or PEEK 704 implant coated, or saturated, with a piezoelectric material 706.

Figure 8B:
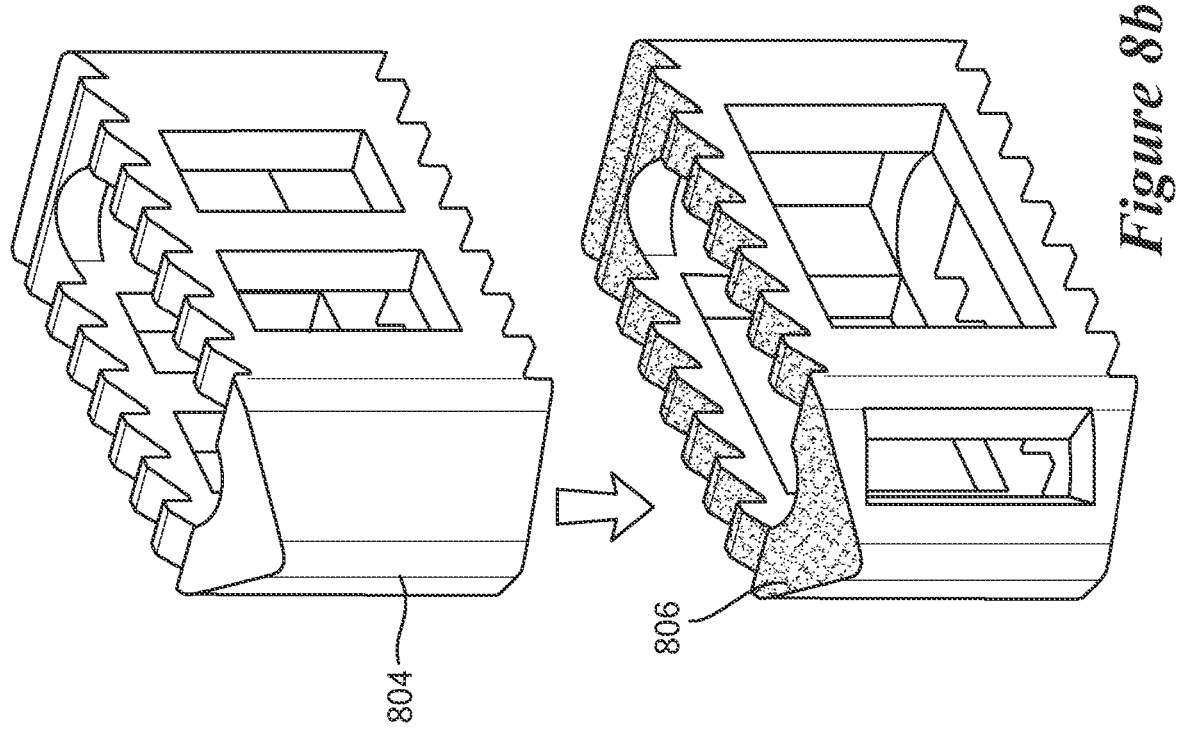
FIGS. 8*a-b* are side perspective views of another embodiment of a piezoelectric spinal implant.
Figure 8A:
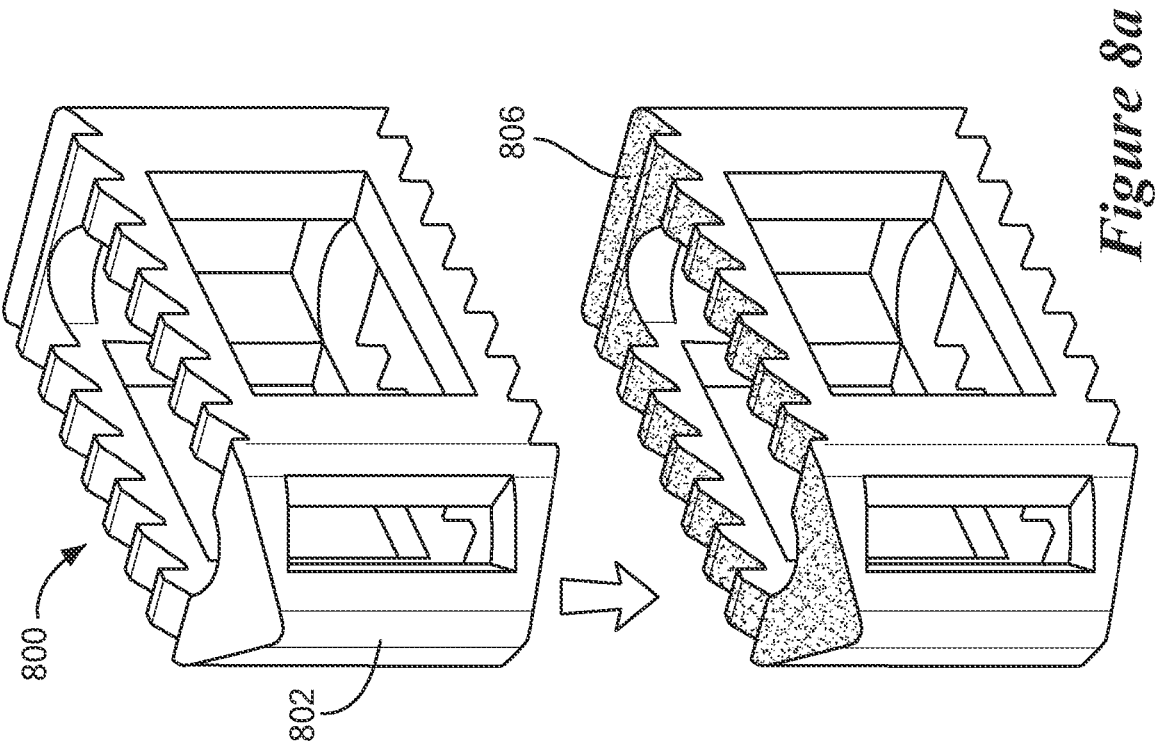

FIGS. 8a-b are side perspective views of an embodiment of a piezoelectric spinal implant 800. This embodiment shows a titanium 802 or PEEK 804 implant with top and bottom surfaces coated with a piezoelectric material 806.

Figure 9A:
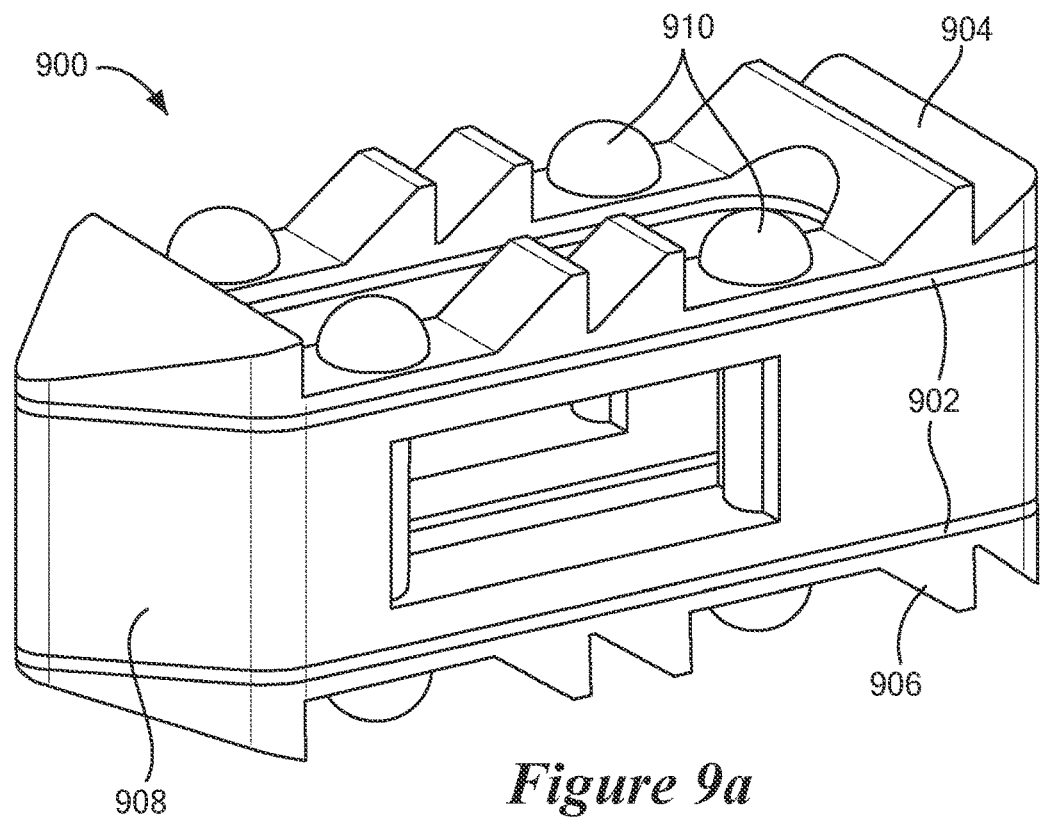
FIGS. 9*a-b* are top and bottom perspective views of another embodiment of a piezoelectric spinal implant.
Figure 9B:
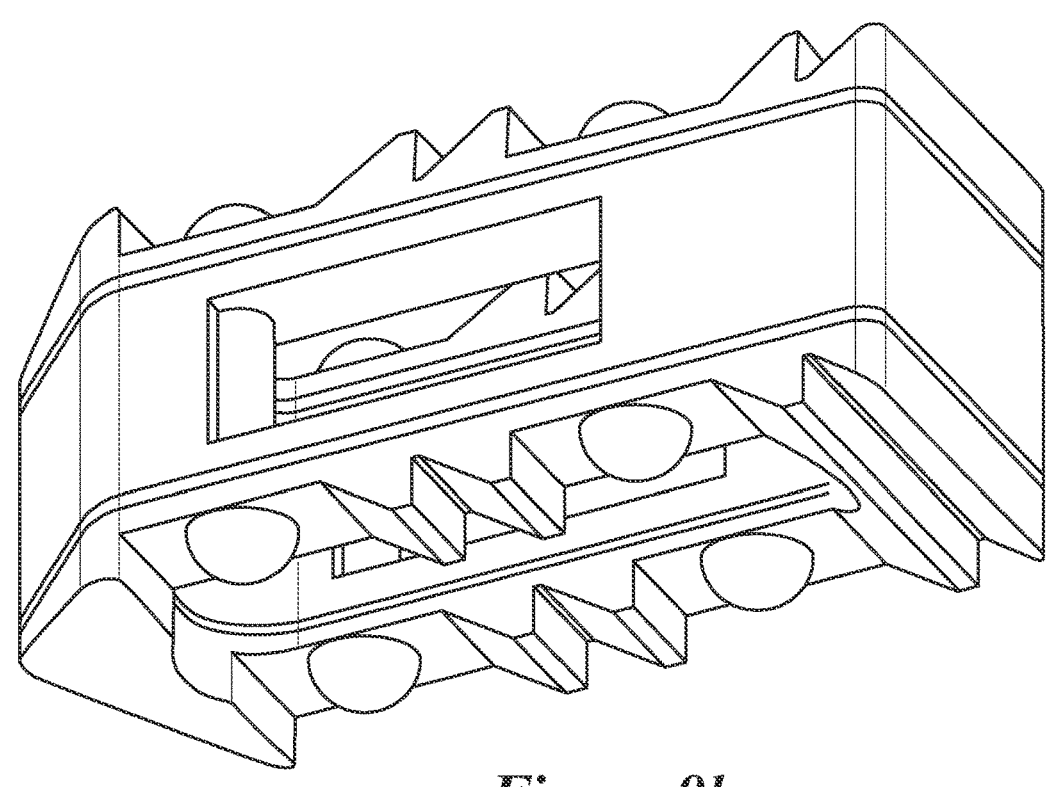

FIGS. 9a-b are top and bottom perspective views of an embodiment of a piezoelectric spinal implant 900. The embodiment shows one or more piezoelectric components 902 assembled between a top 904 and bottom 906 endplate and an insulating or conductive material 908 in the center. The assembly can be constructed using a fastener 910, such as rivets, screws, or dowels to prevent disassembly but allow a mechanical load to be transferred from the endplates to the piezoelectric material.

Figure 10A:
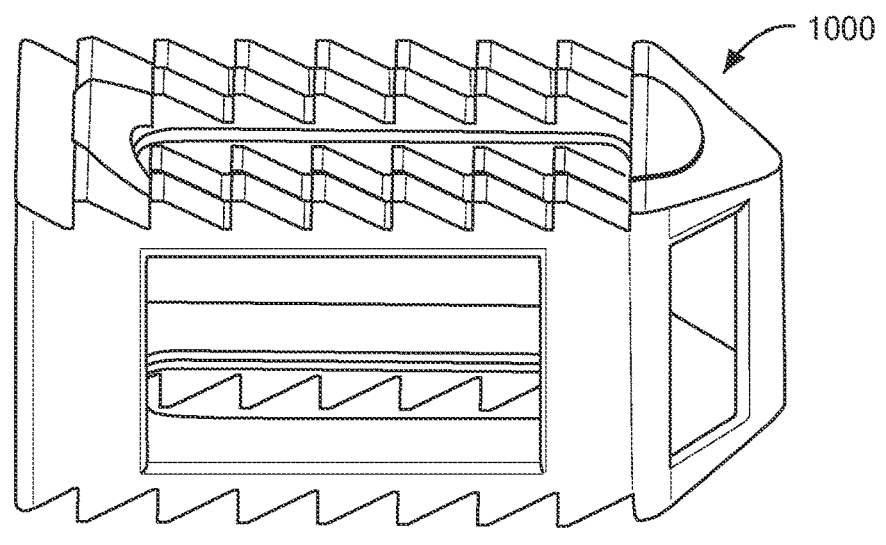
FIGS. 10*a-c* are side perspective and detail views of another embodiment of a piezoelectric spinal implant.
Figure 10B:
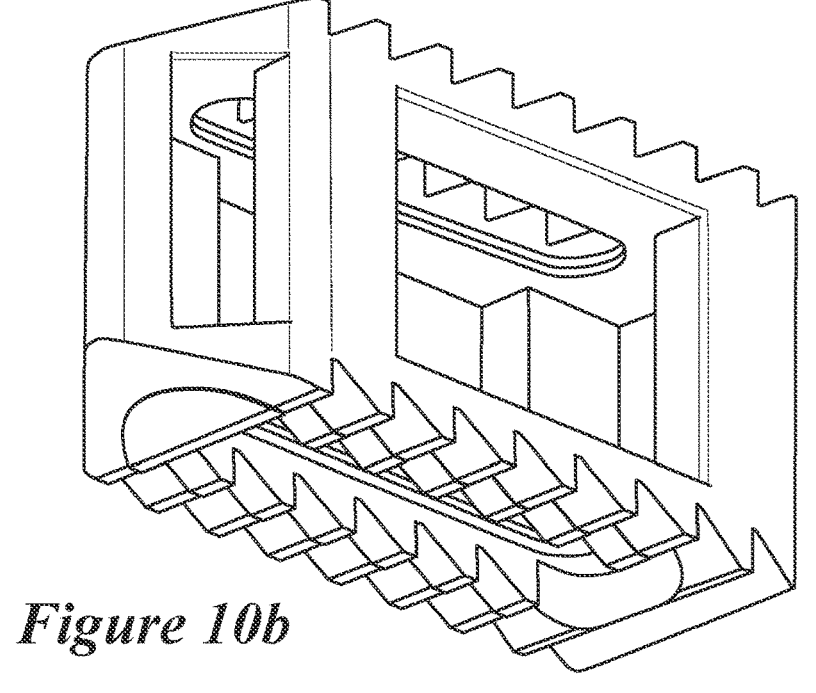
Figure 10C:
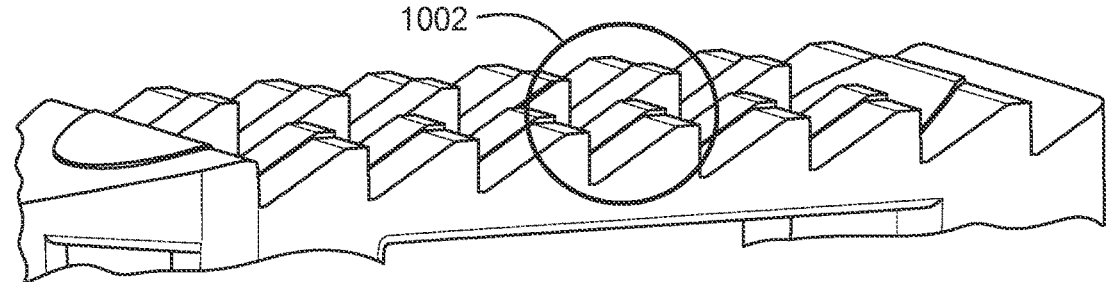

FIGS. 10a-c are side perspective and detail views of an embodiment of a piezoelectric spinal implant 1000. The embodiment shows a piezoelectric component 1002 that is taller than or level with the mechanically supportive implant to which applied forces will transfer to the piezoelectric component.

Figure 11A:
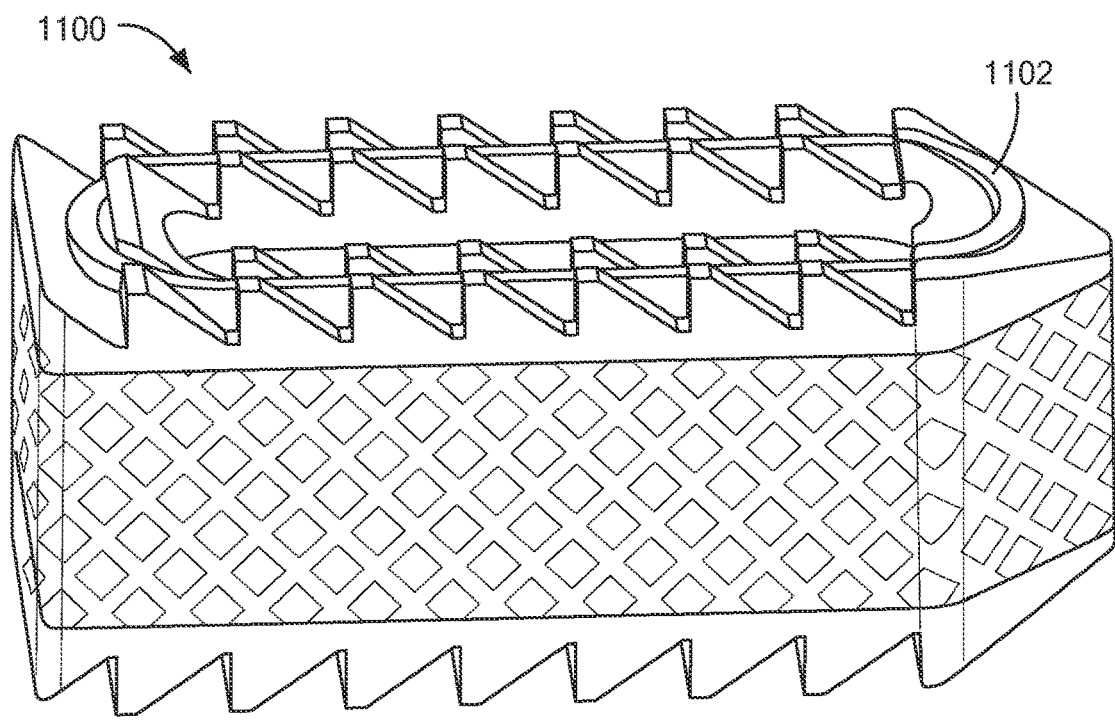
FIGS. 11*a-b* are side perspective views of another embodiment of a piezoelectric spinal implant.
Figure 11B:
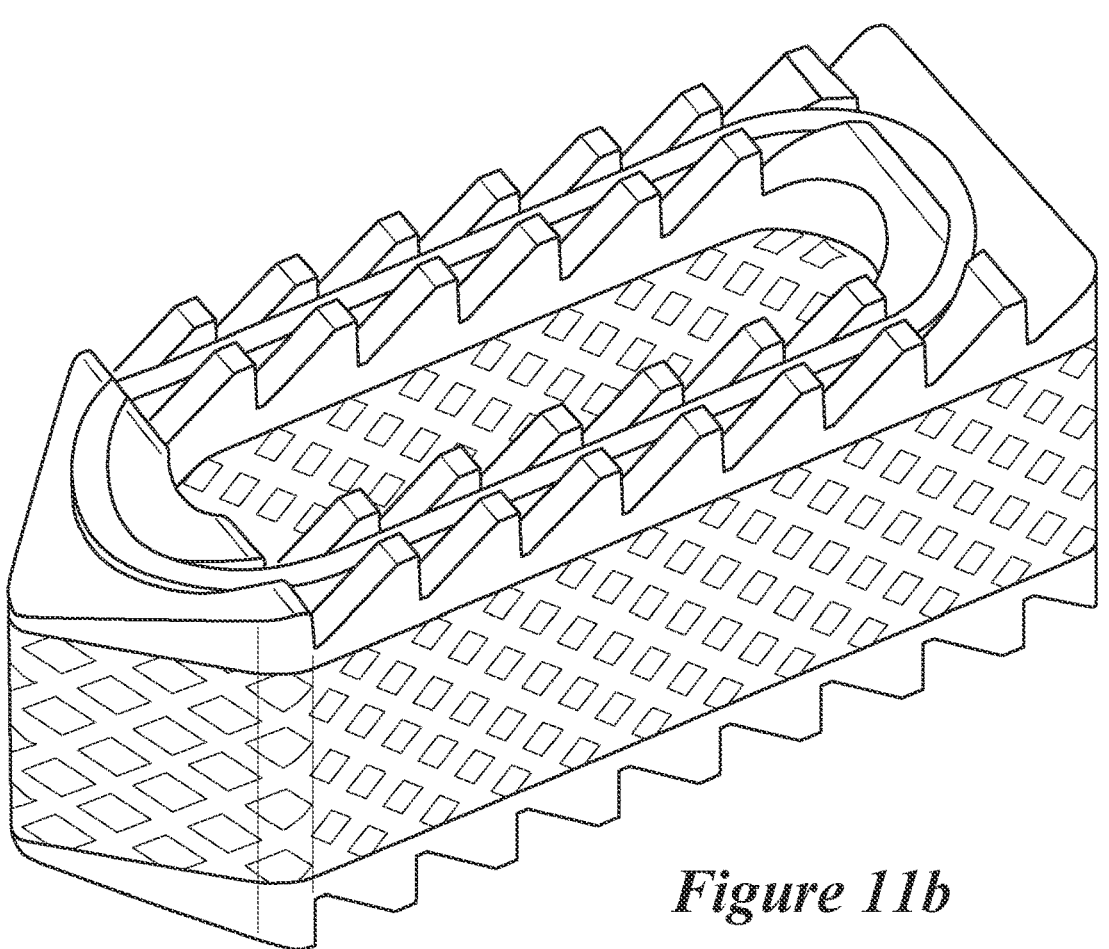

FIGS. 11a-b are side perspective views of an embodiment of a piezoelectric spinal implant 1100. The embodiment shows a piezoelectric component 1102 that is oval, ring, rectangle, or pill shaped and may be taller than or level with the mechanically supportive implant to which applied forces will transfer to the piezoelectric component.

Figure 12:
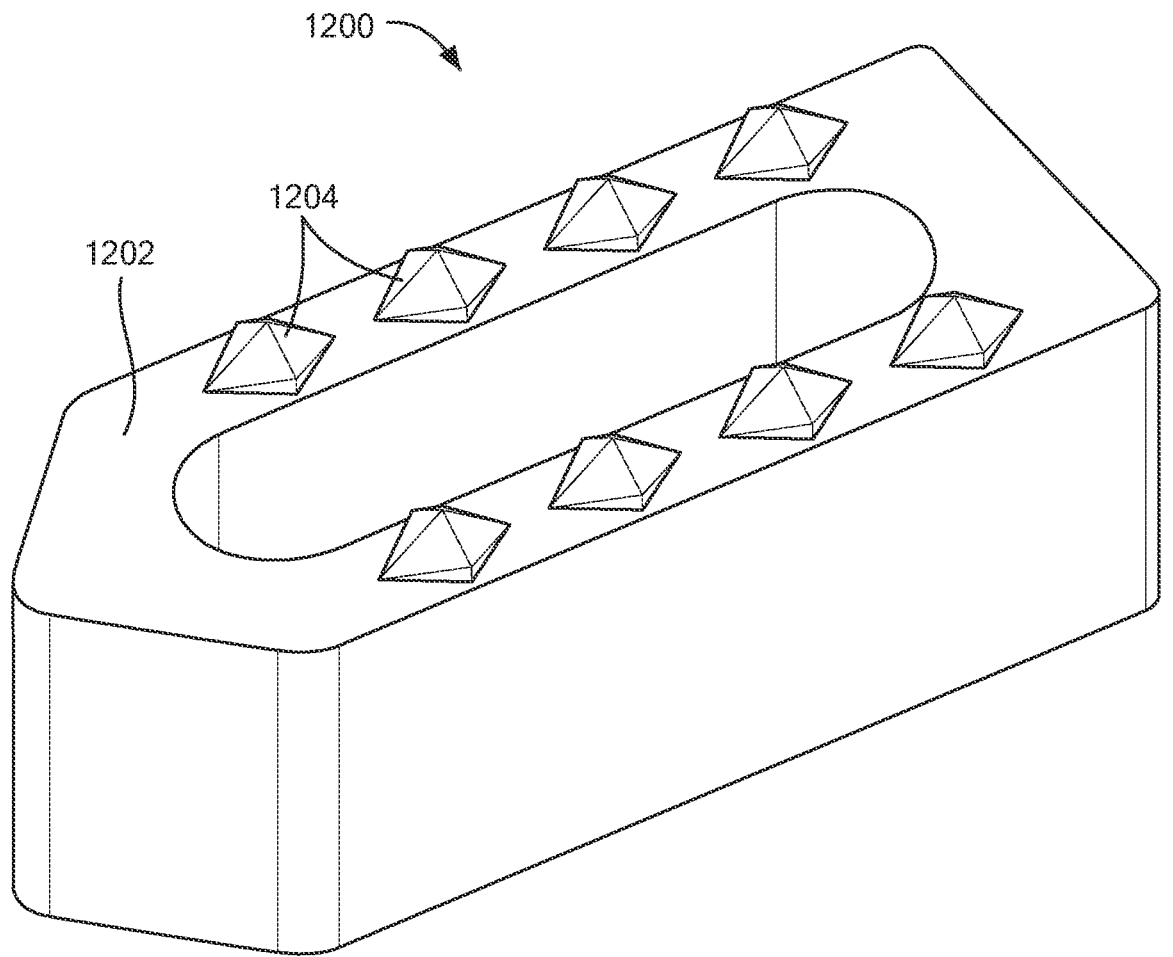
FIG. 12 is a top perspective view of another embodiment of a piezoelectric spinal implant.

FIG. 12 is a top perspective view of an embodiment of a piezoelectric spinal implant 1200. The embodiment shows a piezoelectric component 1202 that is shorter than or level with the mechanically supportive implant to which the forces applied will actuate the piezoelectric component 1202. The implant 1200 may have protrusions or spikes 1204 extending above or level with the piezoelectric component 1202.

Figures 13A, 13B, 13C:
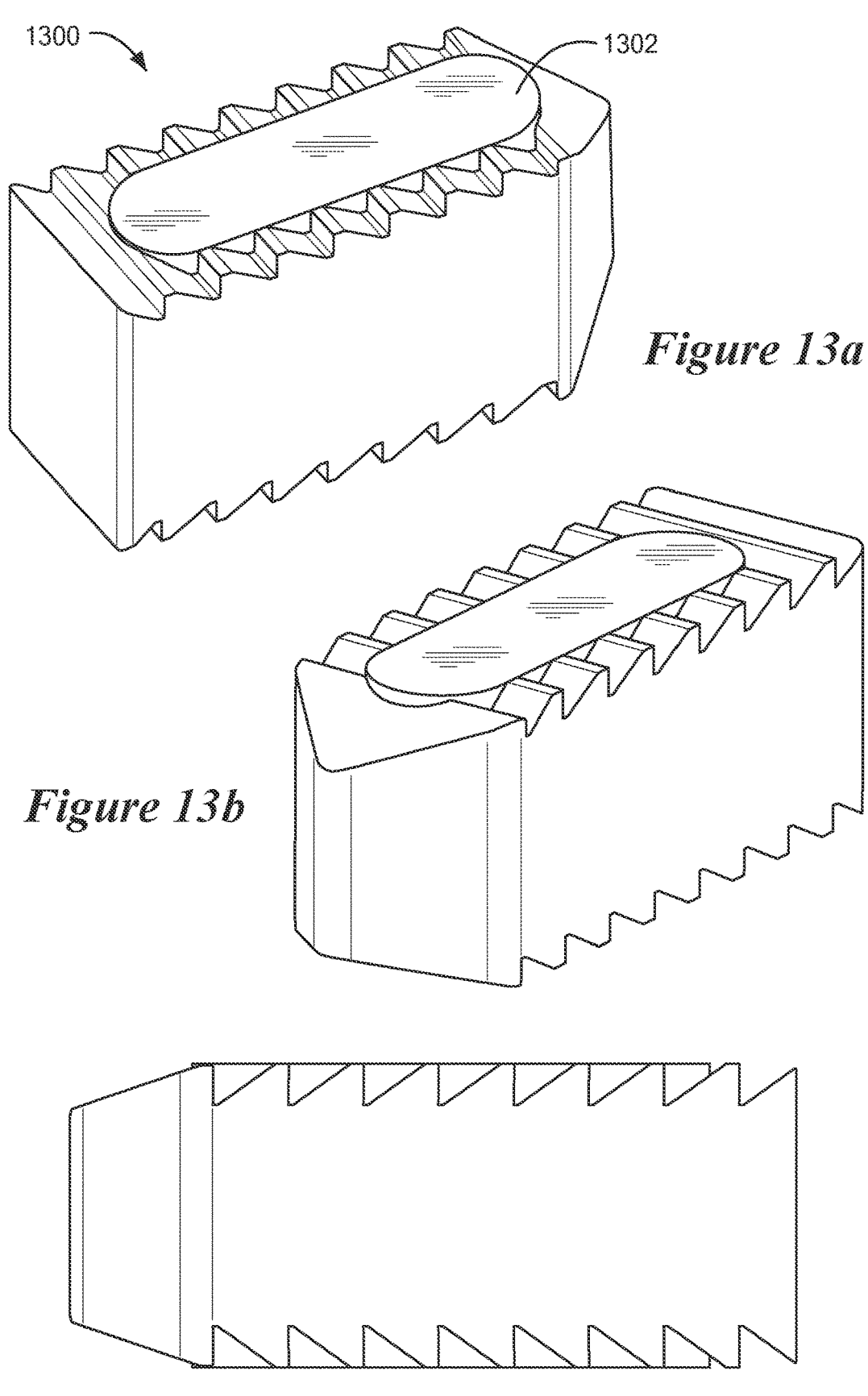
FIGS. 13*a-c* are side perspective and side views of another embodiment of a piezoelectric spinal implant.

FIGS. 13a-c are side perspective and side views of an embodiment of a piezoelectric spinal implant 1300. The embodiment shows a piezoelectric insert 1302 that is added independently to a traditional mechanically supportive implant. The insert can sit above, even with, or below the traditional implant. The insert may be inserted into the lumen of the spinal implant.

Figure 14A:
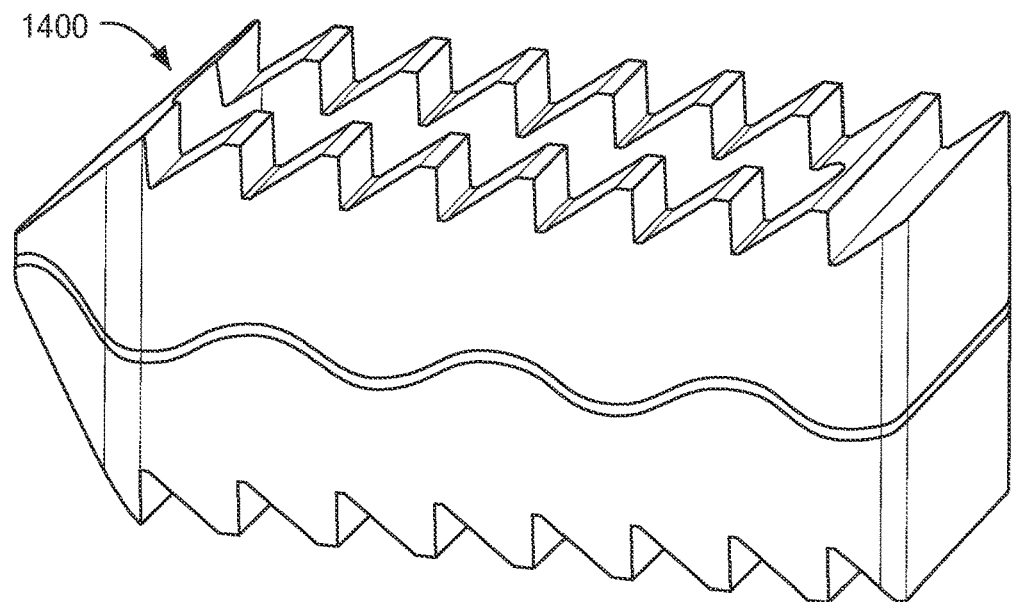
FIGS. 14*a-b* are side perspective and exploded views of another embodiment of a piezoelectric spinal implant.
Figure 14B:
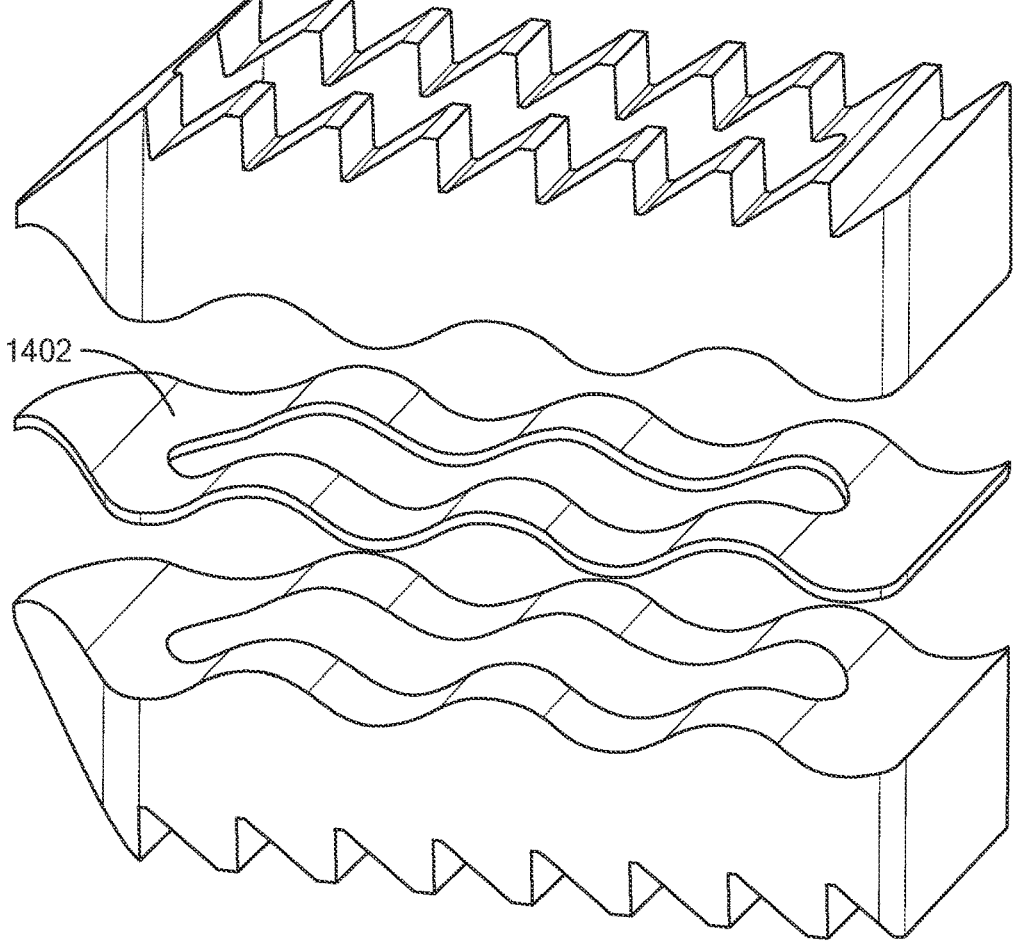

FIGS. 14a-b are side perspective and exploded views of an embodiment of a piezoelectric spinal implant 1400. The embodiment describes a wave design that non-uniformly loads the piezoelectric component 1402. Waves can extend front to back, side to side, or both and can be applied to the entire width and length or partial sections of the implant.

Figure 15A:
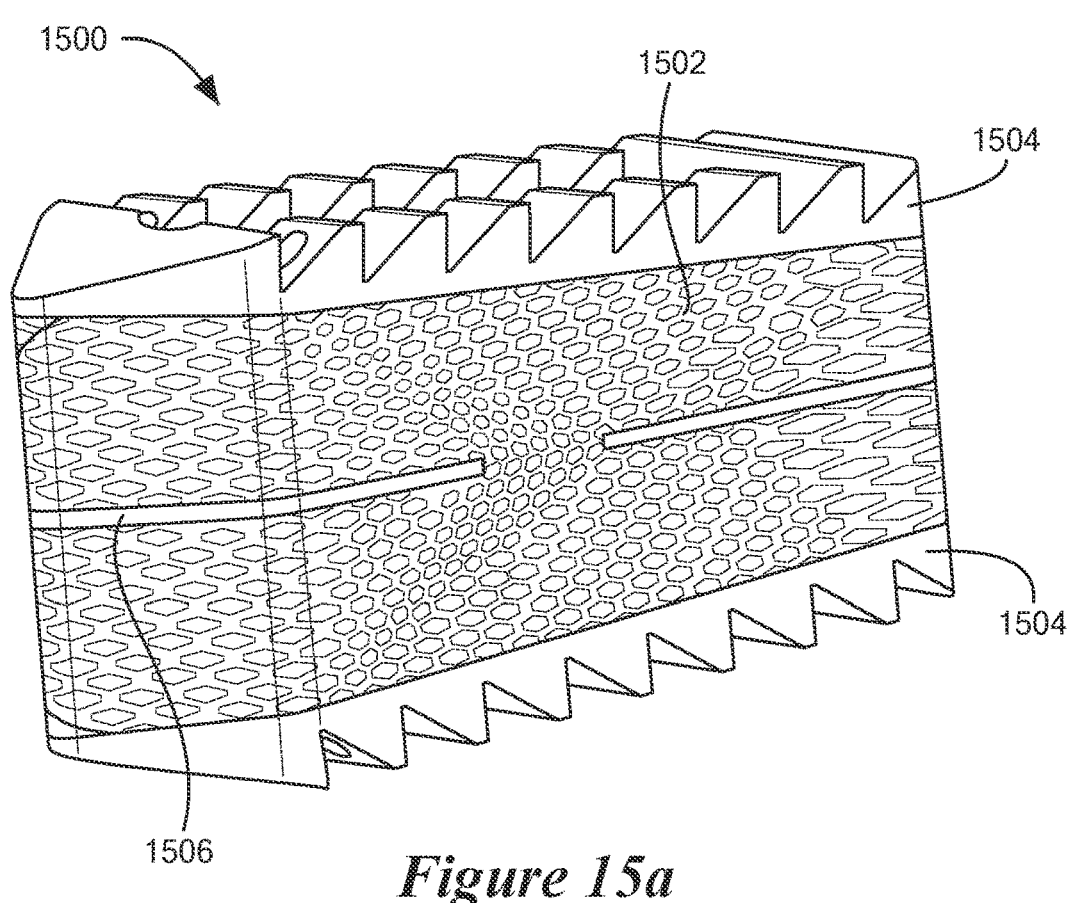
FIGS. 15*a-c* are side perspective and top detail views of another embodiment of a piezoelectric spinal implant.
Figure 15B:
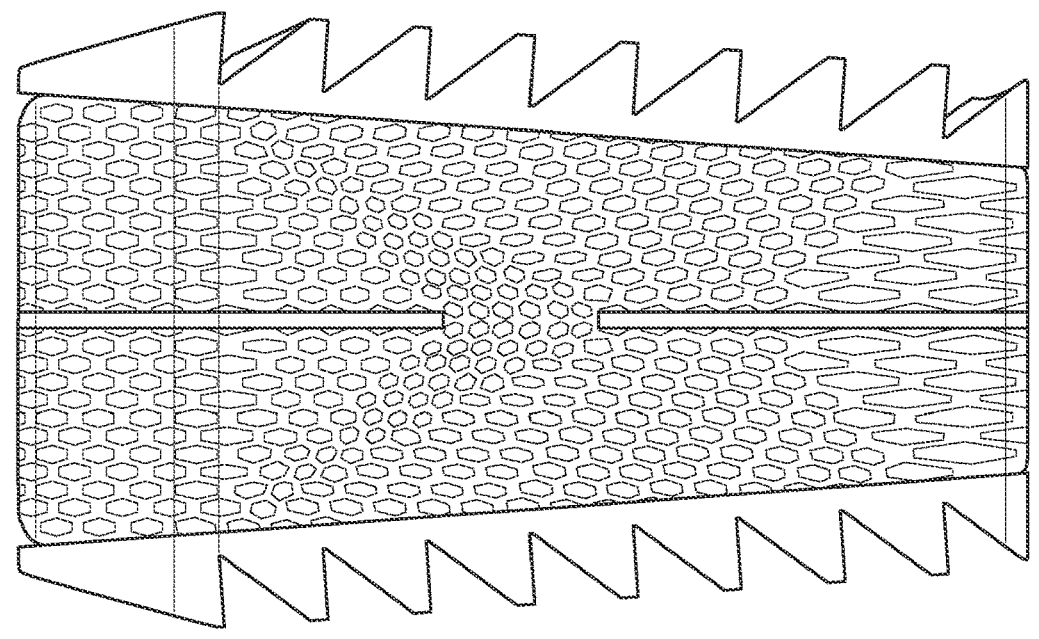
Figure 15C:
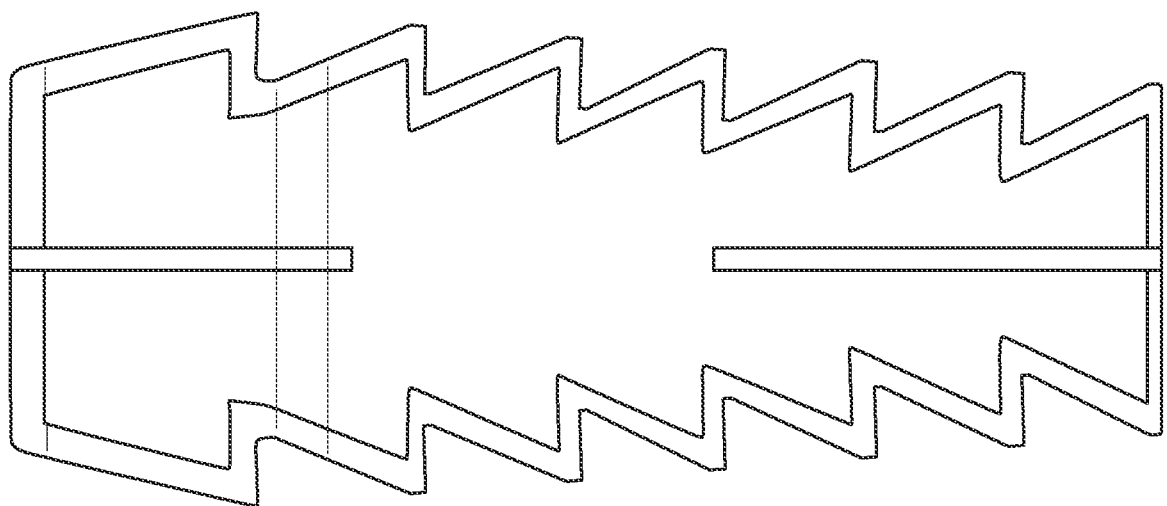
Figure 16A:
FIGS. 16*a-d* are front and side perspective views of another embodiment of a piezoelectric spinal implant.
Figure 16B:
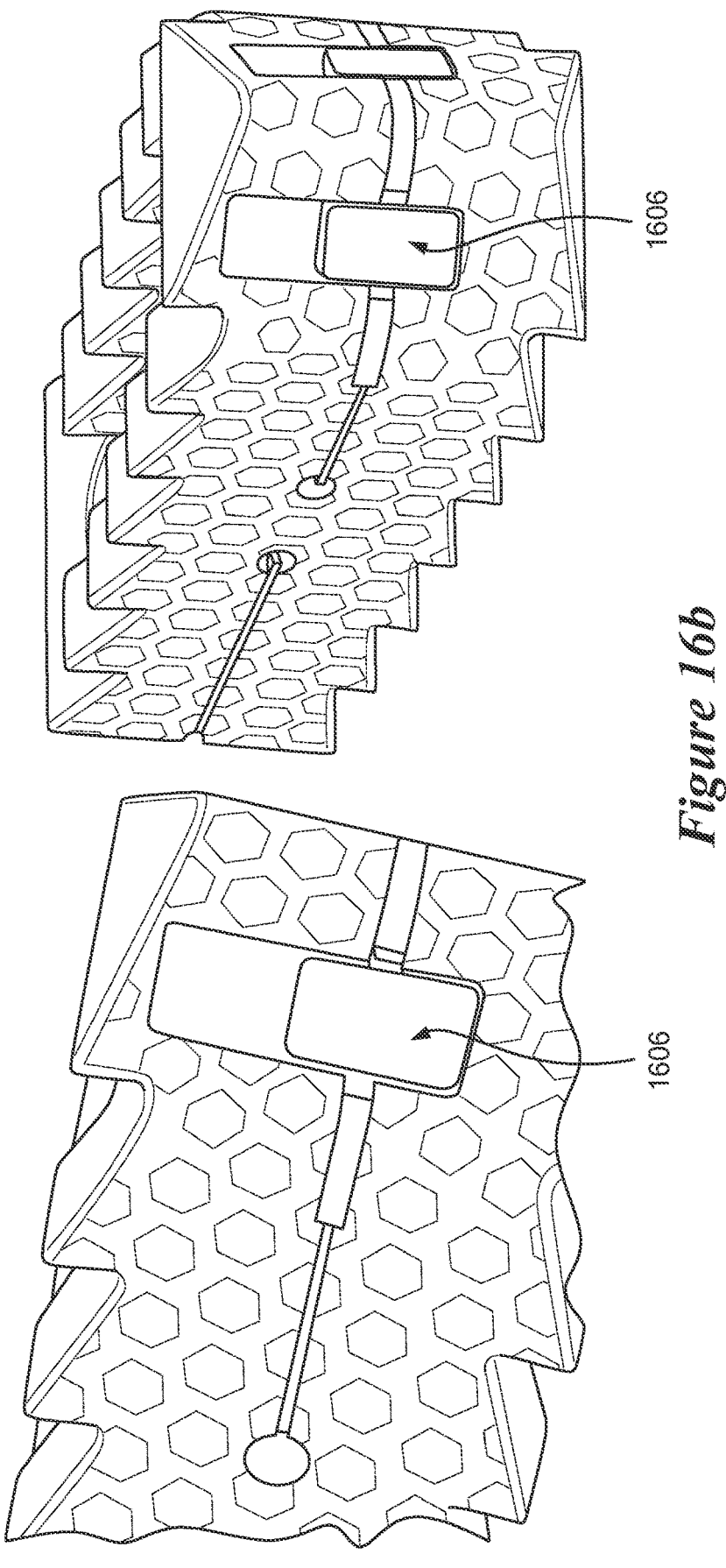
Figure 16C:
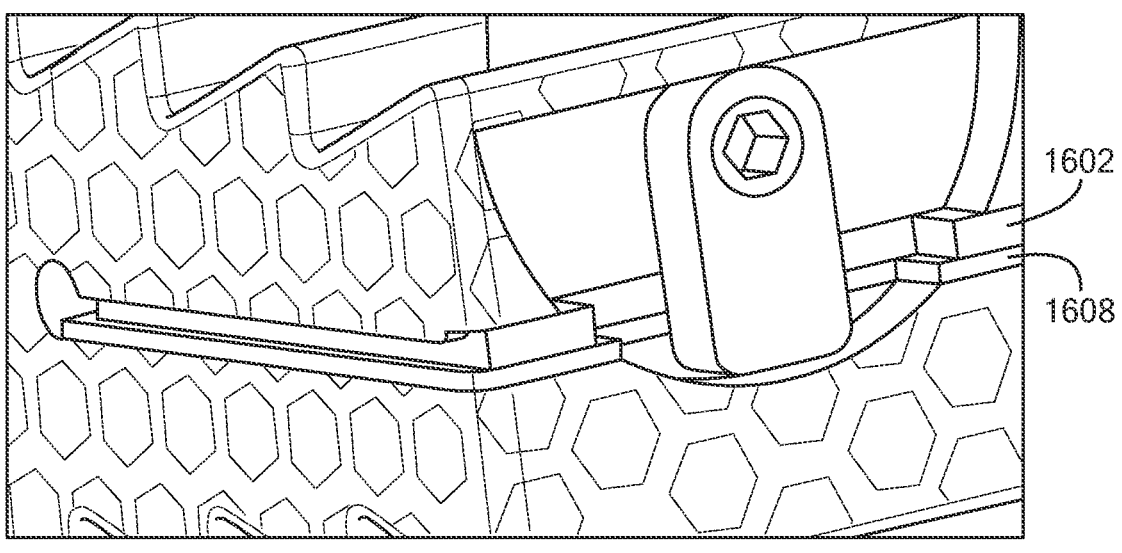
Figure 16D:
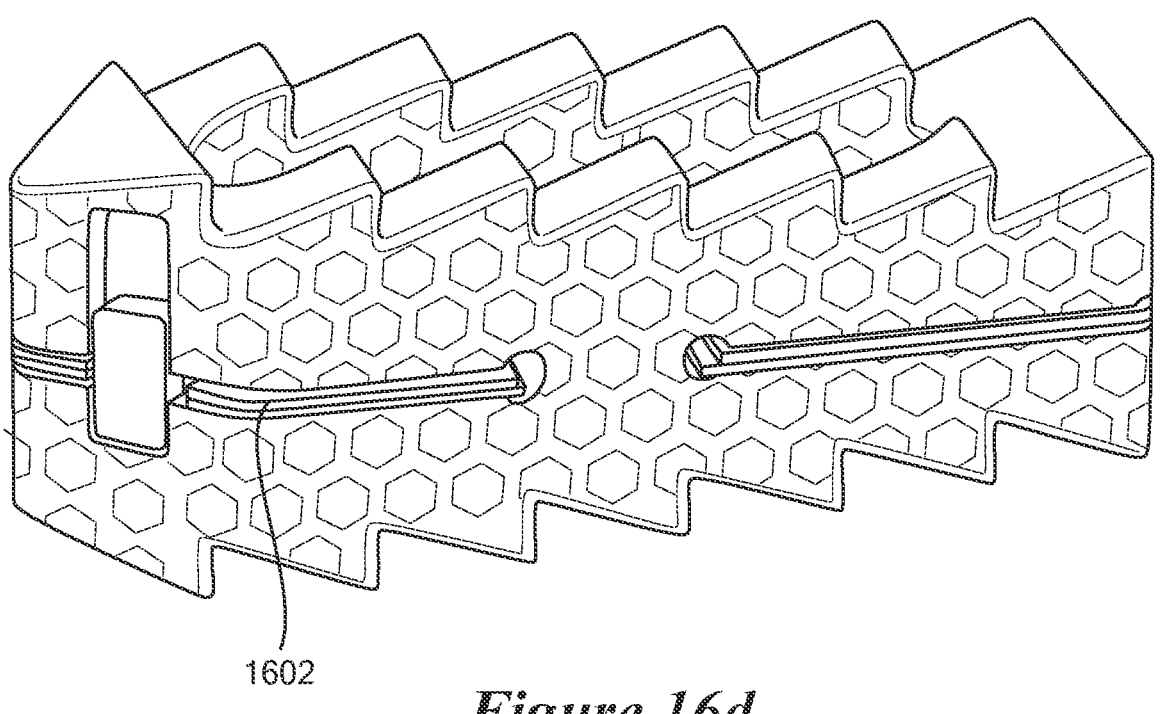

FIGS. 15a-c are side perspective and top detail views of an embodiment of a piezoelectric spinal implant 1500. The embodiment shows a mechanically loaded lattice 1502 or other load bearing geometry that allows the force to transfer from the endplates 1504 to one or more: piezoelectric components 1506 located between the endplates. The lattice can have a uniform stiffness throughout the implant or a variable stiffness that is variable based on location.

FIGS. 16a-d are front and side perspective views of an embodiment of a piezoelectric spinal implant 1600. The embodiment shows a mechanically loaded lattice or other load bearing geometry that allows the force to transfer from the endplates to a piezoelectric component 1602 located at a location between the endplates. The lattice can have a uniform stiffness throughout the implant or a variable stiffness that is variable based on location. The piezoelectric component 1602 can be inserted into a slot built inside the implant and captured in place using a tab or other blocking mechanism, such as a swing lock 1604 or a slide tab 1606. The assembly can contain an insulating sheet, film, or block 1608 on one side of the piezoelectric component 1602 to prevent short circuit or offsetting positive/negative output.

Figure 17A:
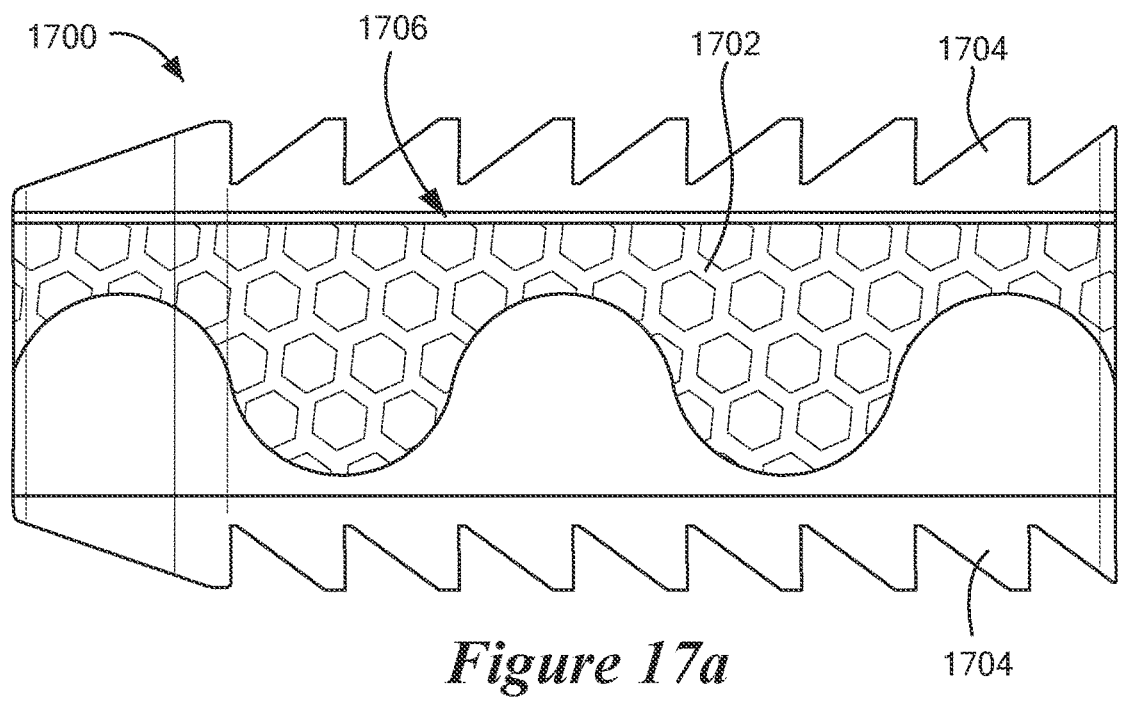
FIGS. 17*a-b* are right side and side perspective views of another embodiment of a piezoelectric spinal implant.
Figure 17B:
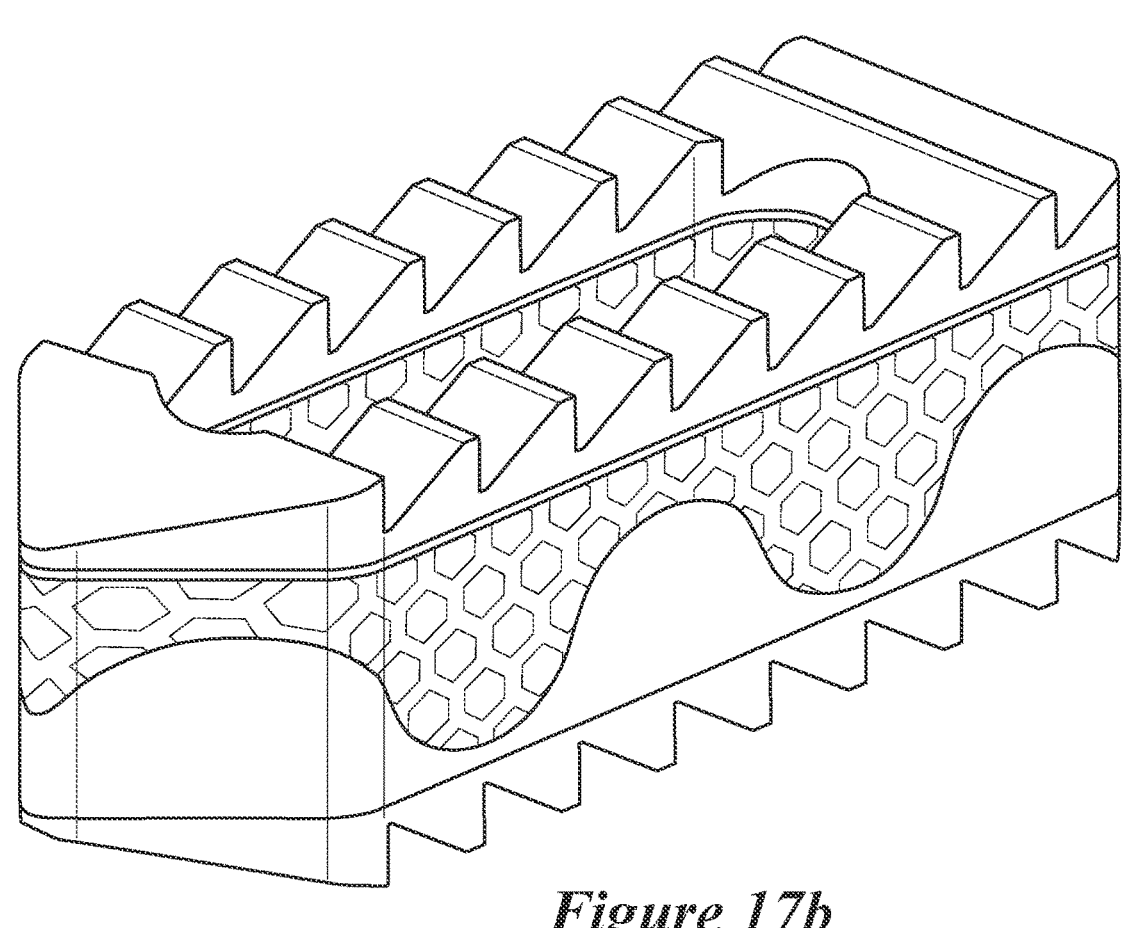

FIGS. 17a-b are right side and side perspective views of an embodiment of a piezoelectric spinal implant 1700. The embodiment shows a mechanically loaded lattice 1702 or other load bearing geometry that allows an applied force to transfer from the endplates 1704 to a piezoelectric component 1706 located between the endplates 1704. The lattice 1702 can have a uniform stiffness throughout the implant or a variable stiffness that is variable based on location. The lattice 1702 or structural geometry can be in the shape of a flat sided rectangular block or have waves or other geometric fluctuations to provide an uneven distribution or force to the piezoelectric material.

Figure 18:
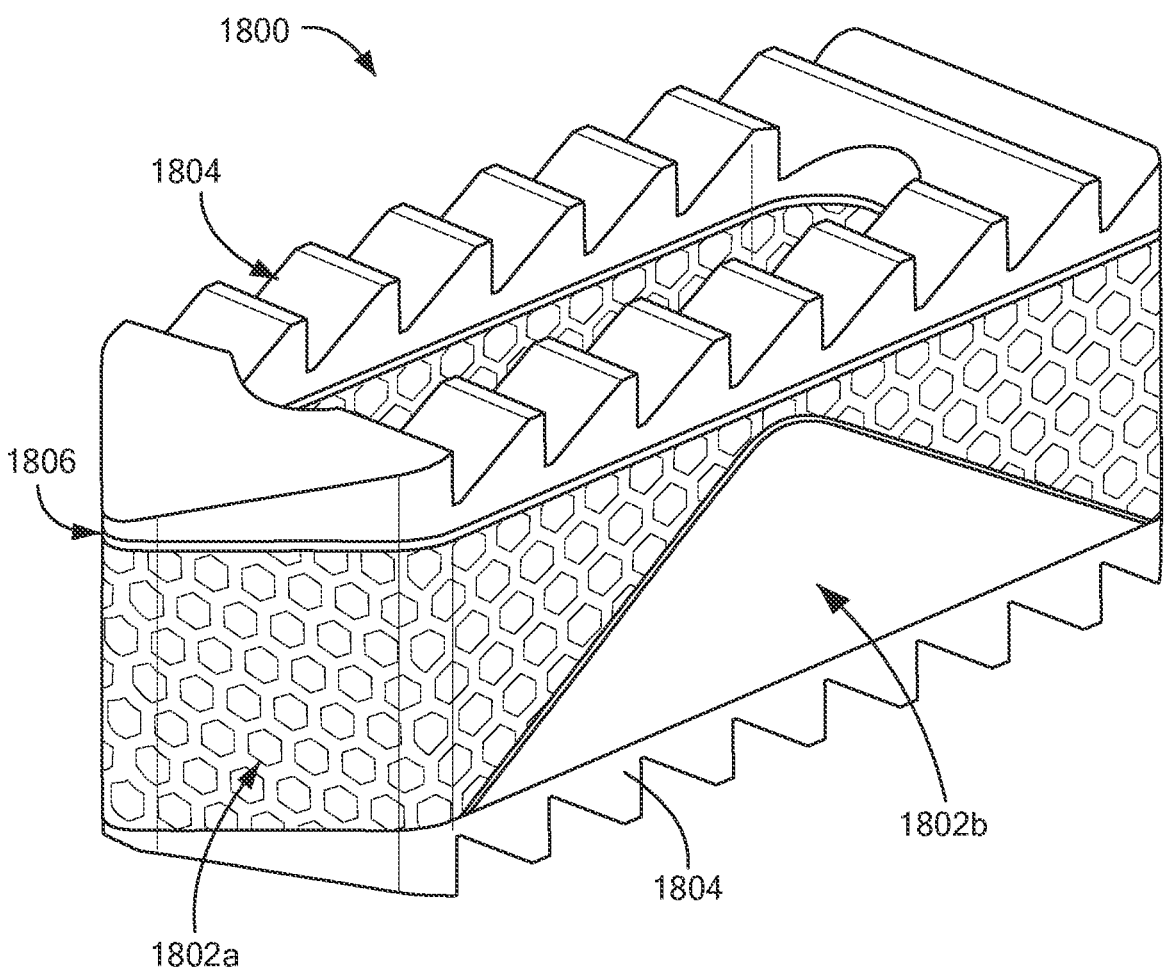
FIG. 18 is a right side perspective view of another embodiment of a piezoelectric spinal implant.
Figures 19A, 19B:
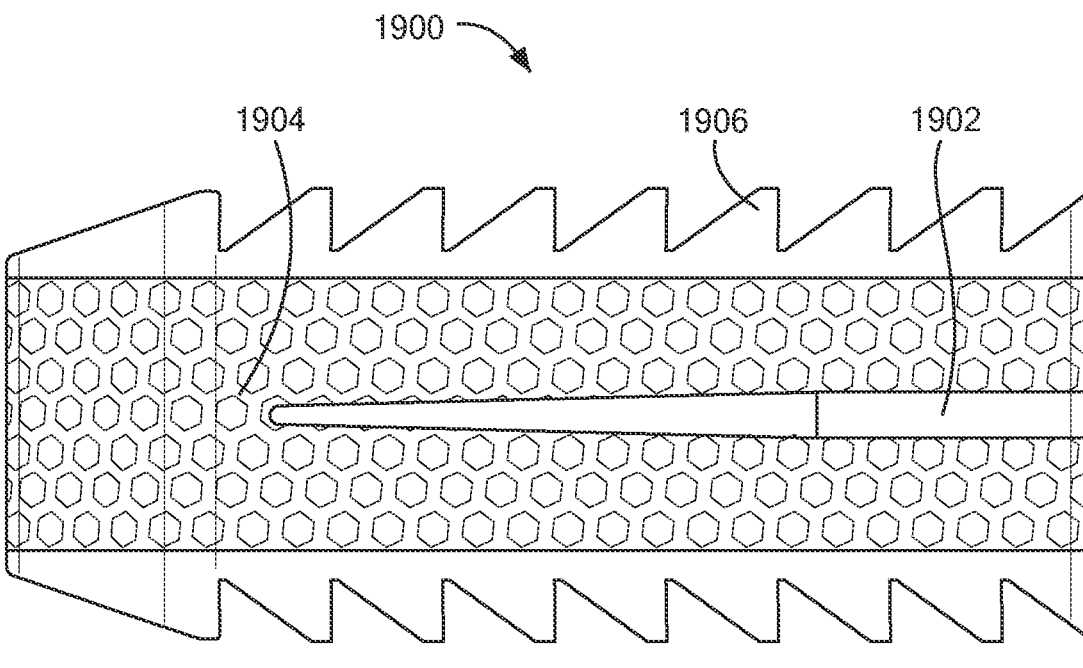
FIGS. 19*a-f* are right side, top perspective, and side perspective views of another embodiment of a piezoelectric spinal implant.
Figure 19C:
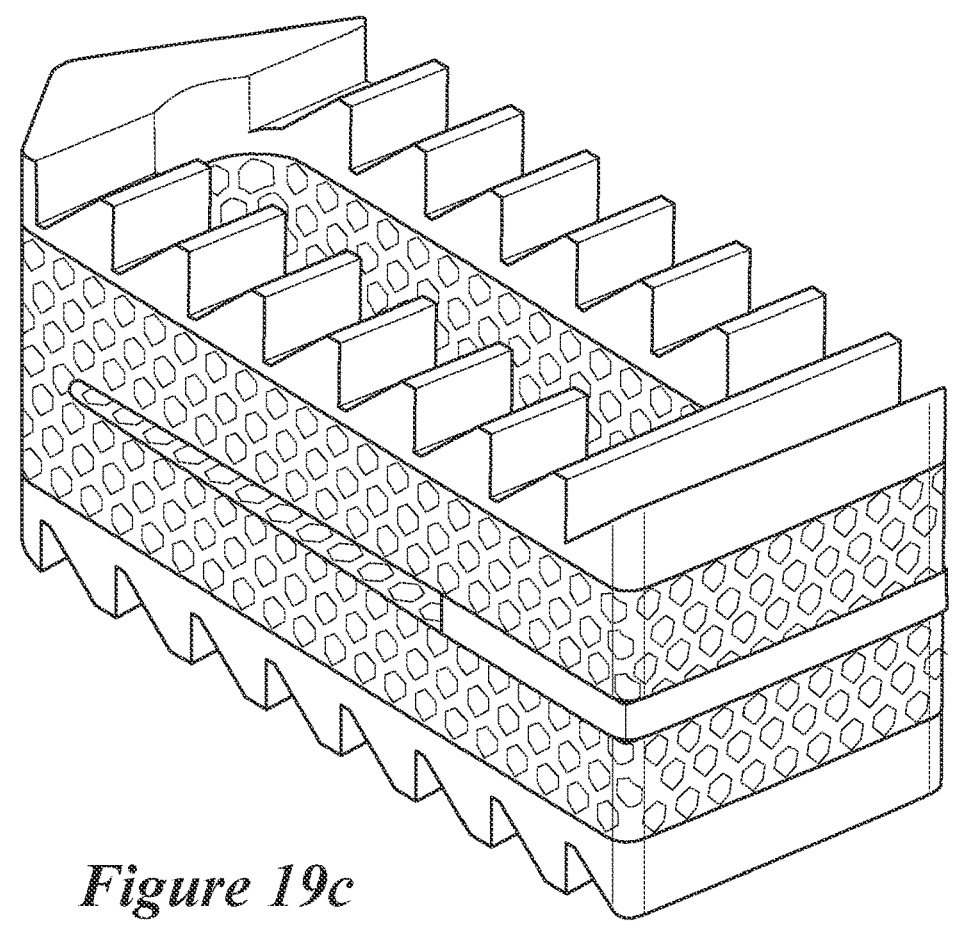
Figure 19D:
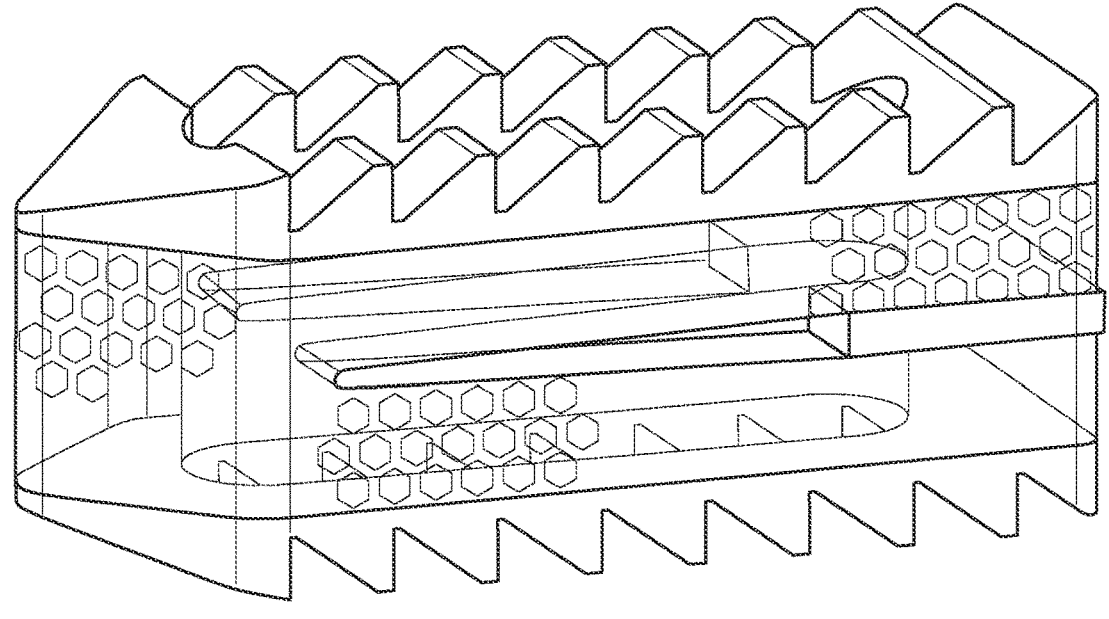
Figure 19E:
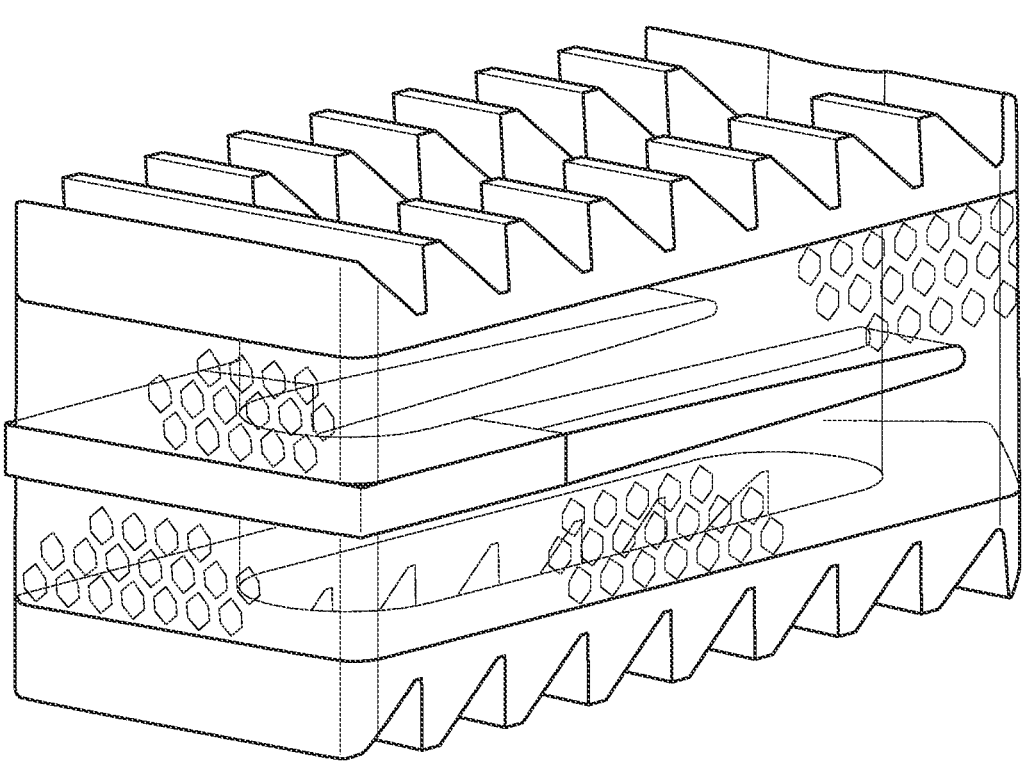
Figure 19F:
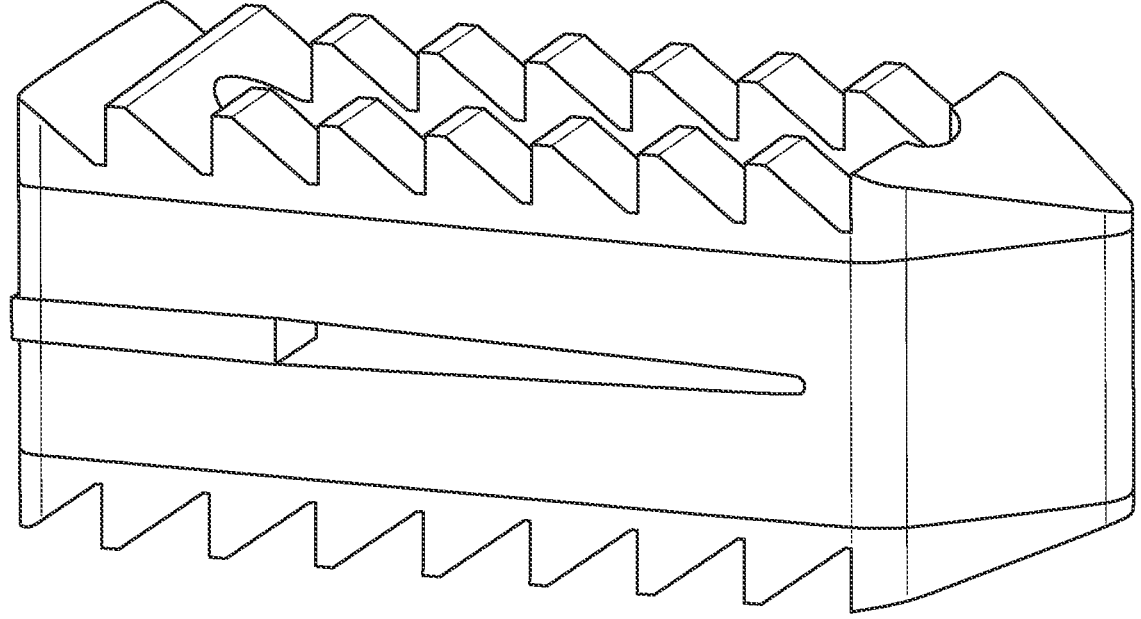

FIG. 18 is a right side perspective view of an embodiment of a piezoelectric spinal implant 1800. The embodiment shows a mechanically loaded lattice 1802a & 1802b or other load bearing geometry that allows an applied force to transfer from the endplates 1804 to a piezoelectric component 1806 located between the endplates 1804. The lattice 1802 a&b can have a uniform stiffness throughout the implant or a variable stiffness that changes based on location. For example the lattice may have a soft portion 1802a and a stiff portion 1802b. The lattice or structural geometry can be in the shape of a flat sided rectangular block or have waves or have other geometric fluctuations to provide an uneven distribution or force to the piezoelectric material.

FIGS. 19a-f are right side, top perspective, and side perspective views of an embodiment of a piezoelectric spinal implant 1900. The embodiment shows an implant with piezoelectric component 1902 on one side opposite a flexible column or hinge 1904 that allows an applied force to transfer from the endplate 1906 to the piezoelectric component.

Figure 20A:
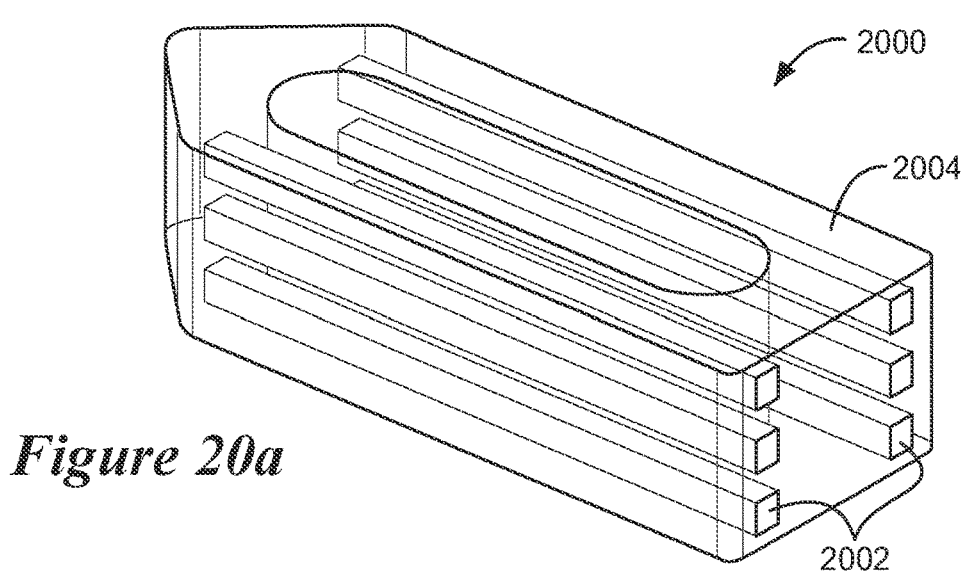
FIGS. 20*a-c* are partially transparent rear perspective, top perspective, and rear perspective views of another embodiment of a piezoelectric spinal implant.
Figure 20B:
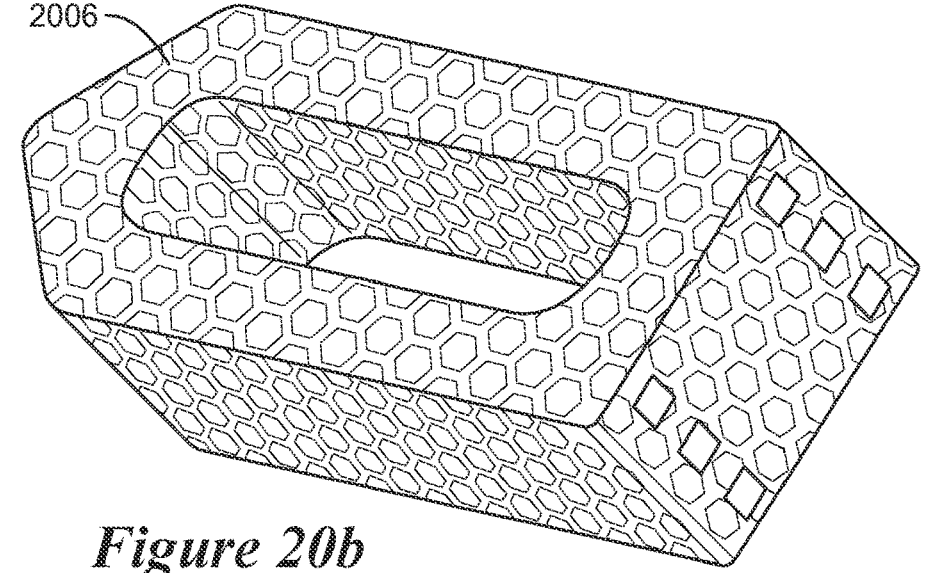
Figure 20C:
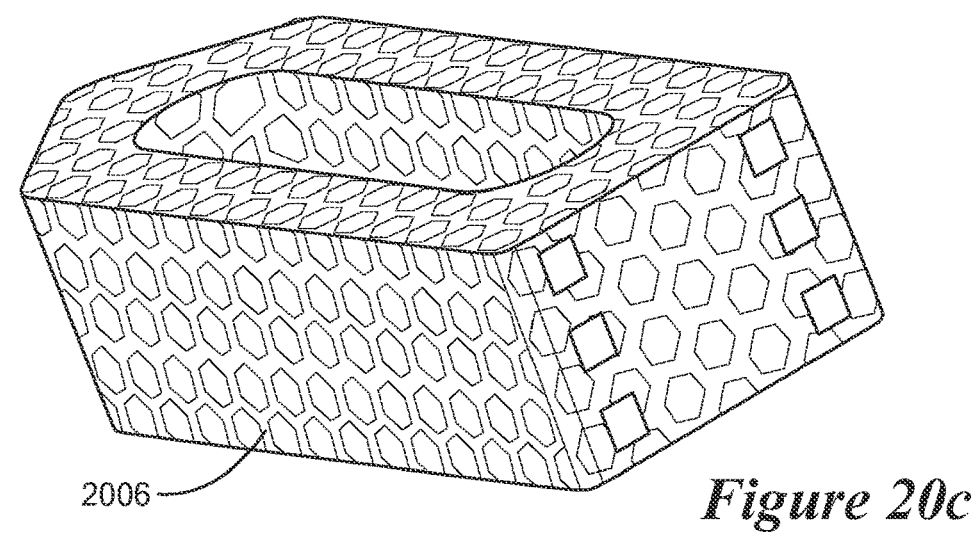

FIGS. 20a-c are partially transparent rear perspective, top perspective, and rear perspective views of an embodiment of a piezoelectric spinal implant 2000. The embodiment shows one or more rods or rails 2002 installed into an implant that is constructed by a conductive or insulating solid material 2004 and/or a load bearing lattice 2006.

Figure 21:
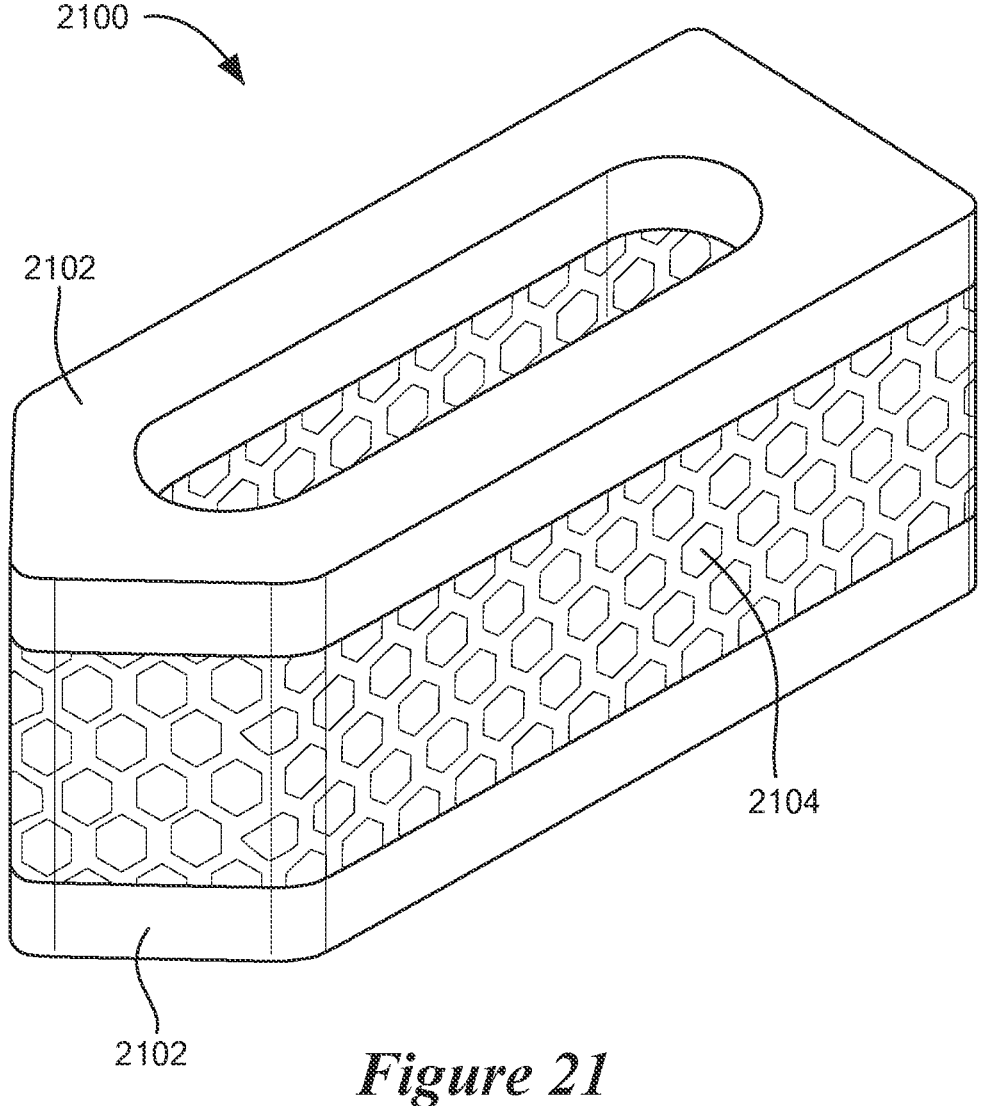
FIG. 21 is a front perspective view of another embodiment of a piezoelectric spinal implant.
Figures 22A, 22B, 22C, 22D:
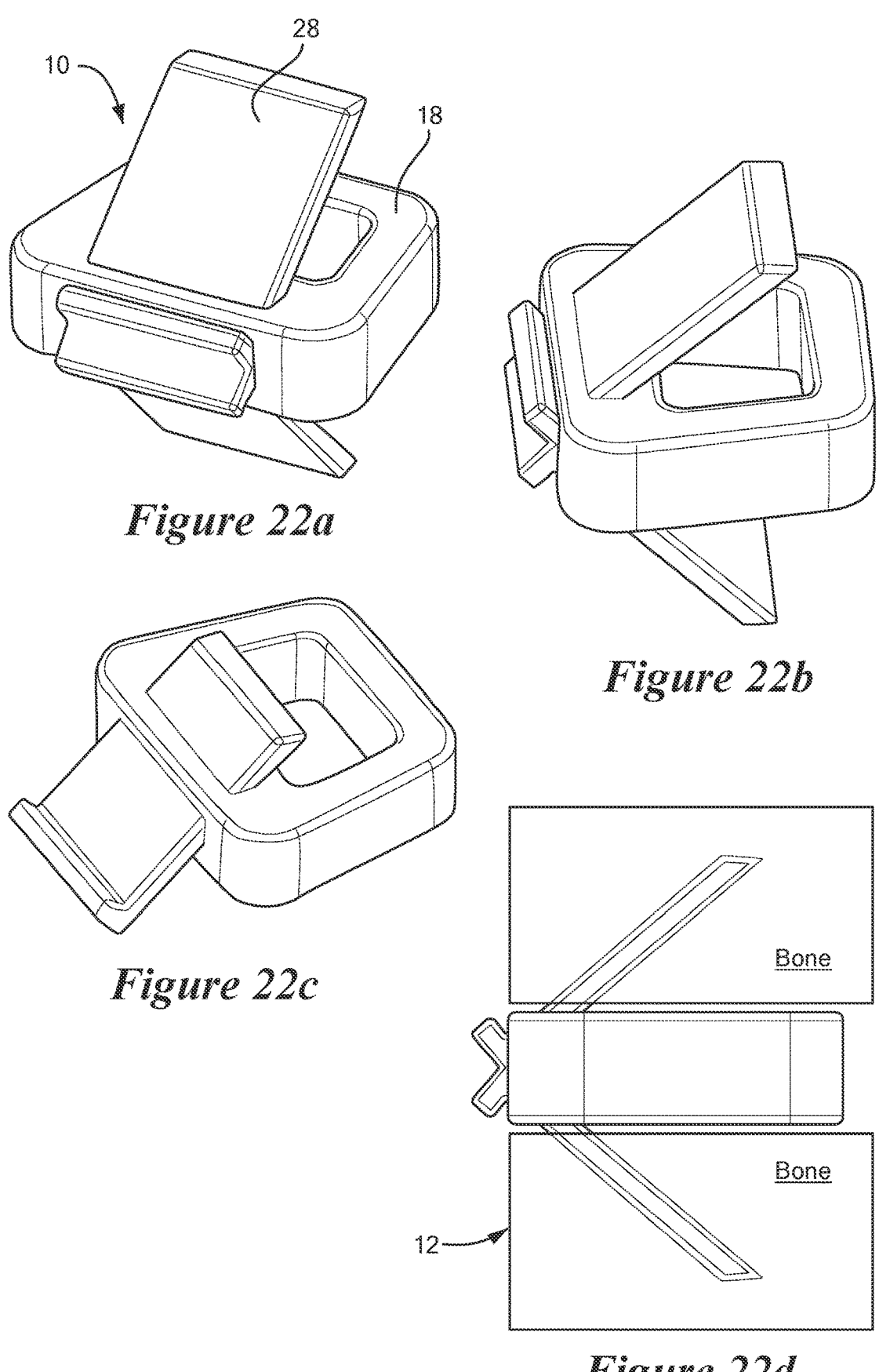
FIGS. 22*a-d* are front, side, and top perspective views of another embodiment of a piezoelectric spinal implant.

FIG. 21 is a front perspective view of an embodiment of a piezoelectric spinal implant 2100. The embodiment shows an implant constructed from one or two piezoelectric endplates 2102 assembled to a center core 2104 that can be made from a conductive or insulating material. The center core can be a solid piece, uniform or non-uniform lattice, or combination of solid and lattice structures.

FIGS. 22a-d are front, side, and top perspective views of an embodiment of a piezoelectric spinal implant. The embodiment shows a bone anchor made from a piezoelectric material that extends through the implant and into the bone. In this embodiment, the implant 12 may be configured to include piezoelectric wings 28 that are configured to extend through the cage body 18 and be affixed within the vertebrae.

Figure 23:
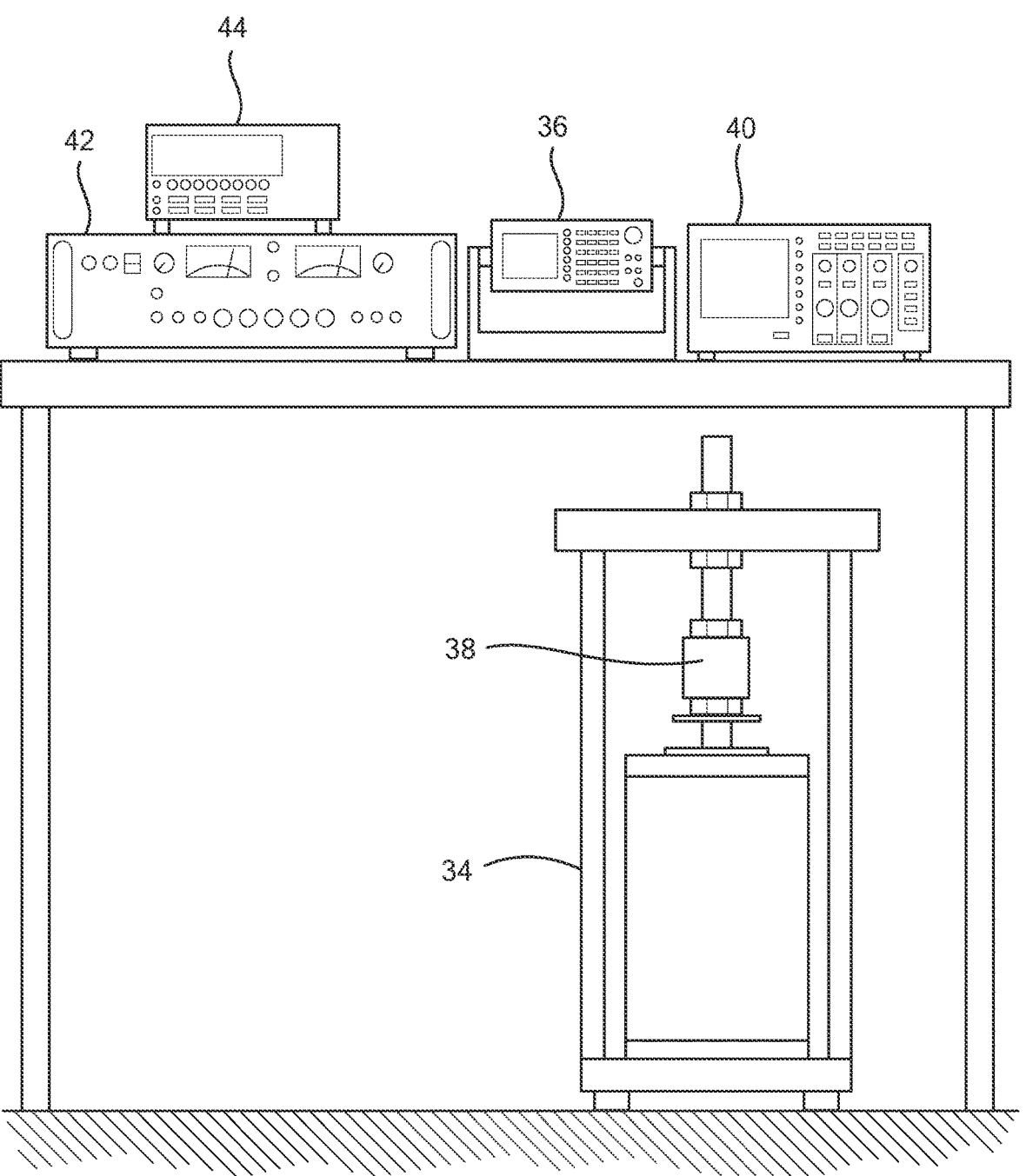
FIG. 23 is a schematic representation of a test set up using a force shaker to replicate the force applied to the implant by user when walking, in accordance with an embodiment of the invention.

FIG. 23 is a schematic representation of a test set up using a force shaker to replicate the force applied to the implant by user when walking.

In one embodiment, the current generated by the piezoelectric film layers were calculated using the experimental set up shown in FIG. 23, which is designed to mimic the frequency associated with the natural walking gait of a user. The tests were carried out by attaching the spinal implant to a vibration shaker 34, capable of generating about 100 pounds of force. The function generator 36 controls the vibration shaker 34, with the frequency of force applied expressed in voltage. A 2 Hz signal was then sent to the vibration shaker 34, which represents the speed of typical bipedal walking. The implant was then propelled into the force sensor 38 which records a force in mV on the oscilloscope 40. Positive and negative leads were attached to the implant and to a power amplifier 42 and current meter 44, which register the current and voltage output experienced across the surface of the implant. As can be seen from the data described below and shown in FIGS. 24 through 29, as pressure/force is applied to the piezoelectric material on the implant, an electrical current is generated. As the force applied to the implant increases, so does the current generated by the implant itself.

Figure 24:
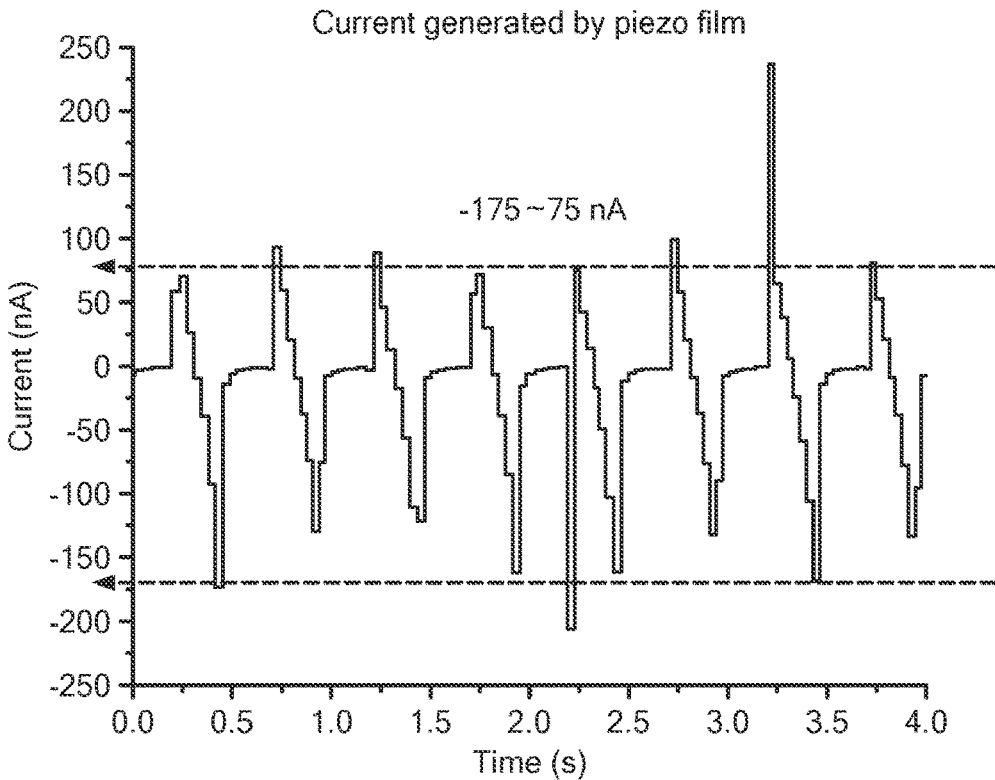
FIGS. 24-29 are graphical representations of the current and voltage produced by the implant under 10, 15, and 20 V of shaking power at 2 Hz frequency, in accordance with an embodiment of the invention.
Figure 25:
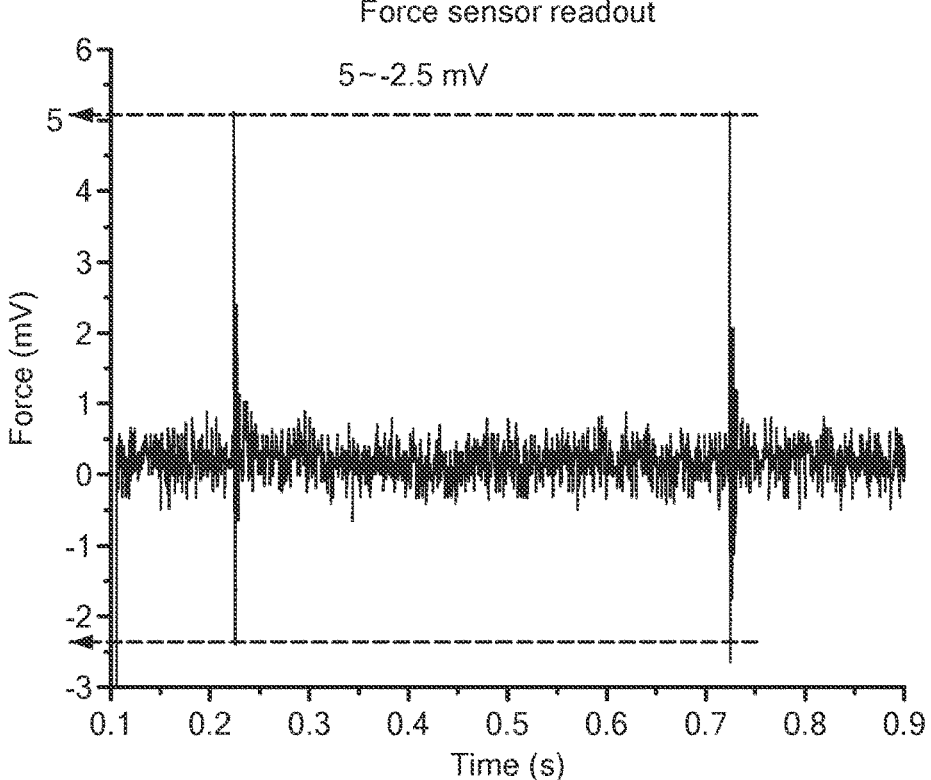
Figure 26:
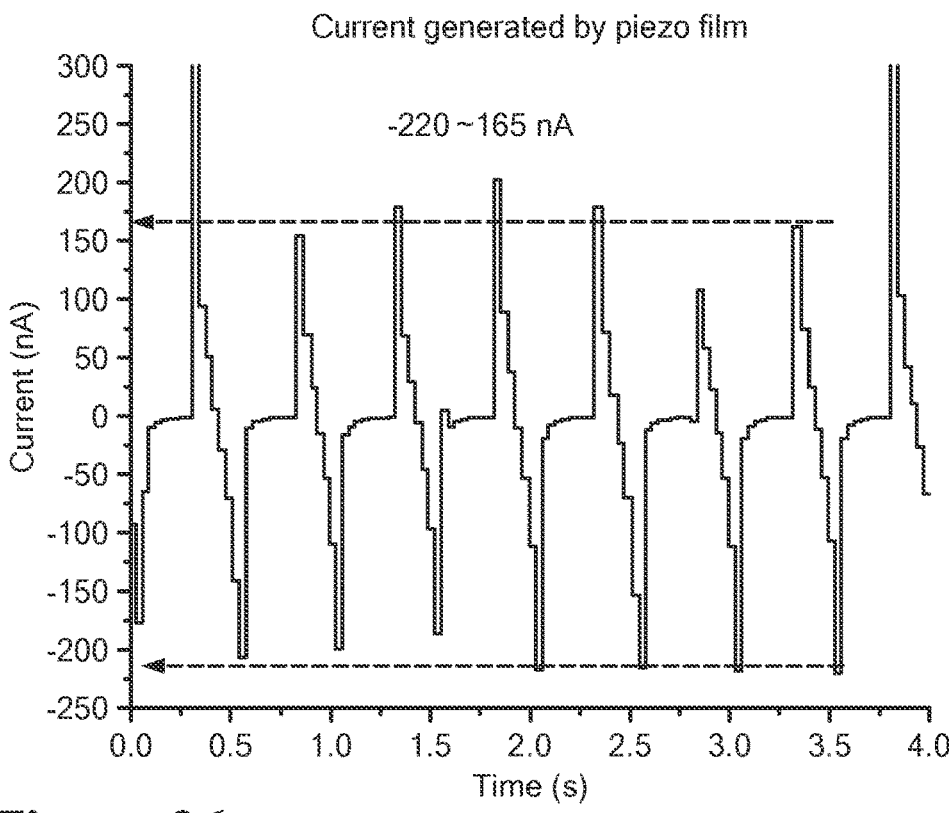
Figure 27:
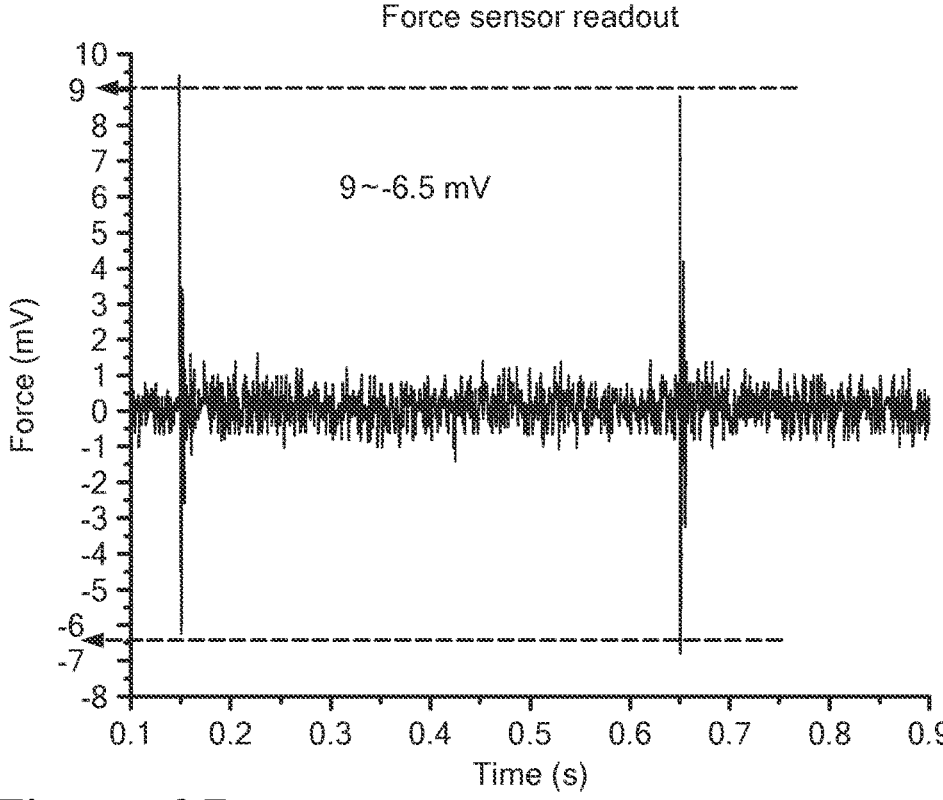
Figures 28, 29:
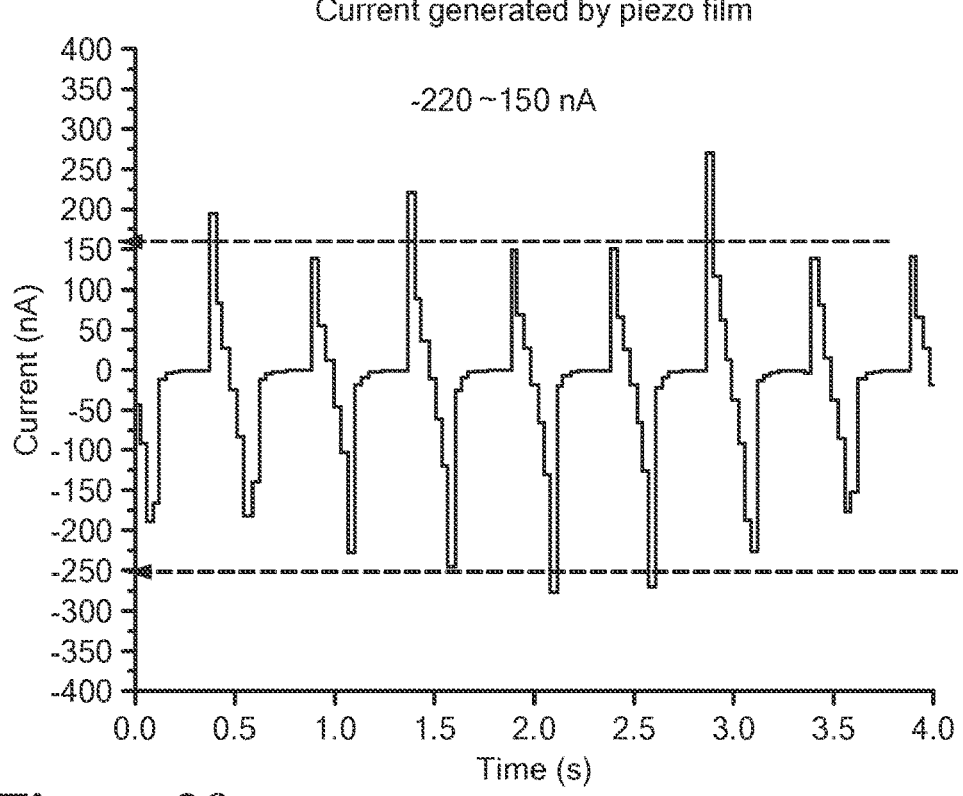
Figure 30:
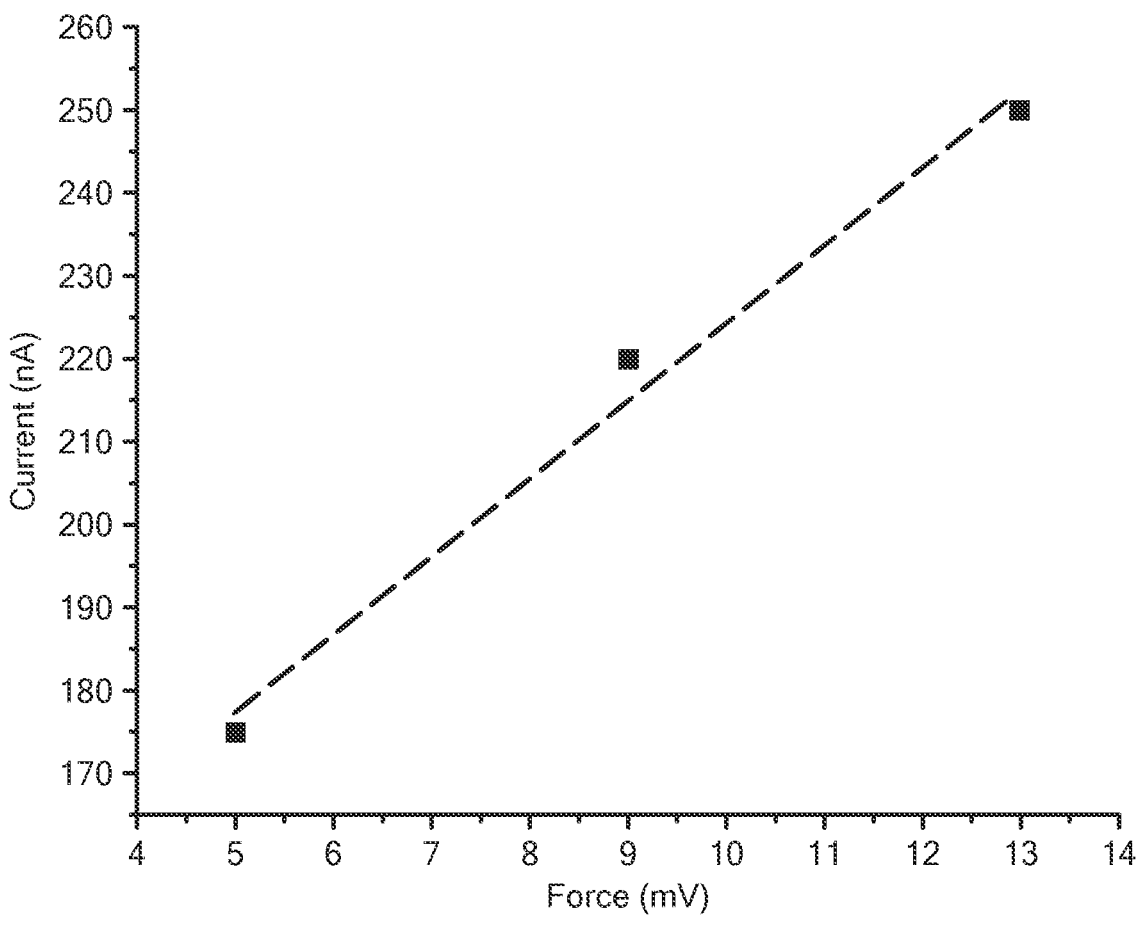
FIG. 30 is the graphical representation of the current generated by the implant under varying forces, in accordance with an embodiment of the invention.

Specifically, using the experimental procedure, it was determined that the current generated by the piezoelectric film under 10 v of shaking power was about −175 to about 75 nA and the voltage was about 5 to about −2.5 mV, as shown in FIGS. 24 and 25. Under 15 v of shaking power, the current and voltage generated were about −220 to about 165 nA and 9 to about −6.5 mV, respectively, as shown in FIGS. 26 and 27. Under about 20 v, the current was about −250 to about 150 nA and the voltage was about 13 to about −8 mV, as shown in FIGS. 28 and 29. As can be seen in FIG. 30, the increasing force applied to the implant is associated with higher current in a linear fashion. One would anticipate based on the linear relationship demonstrated in the experimental setup that the force experienced during normal walking (approximately 1000 Newtons) would increase the expected current to about 0.5 uA.

FIGS. 24-29 are graphical representations of the current and voltage produced by the implant under 10, 15, and 20 V of shaking power at 2 Hz frequency.

FIG. 30 is the graphical representation of the current generated by the implant under varying forces.

Figure 31:
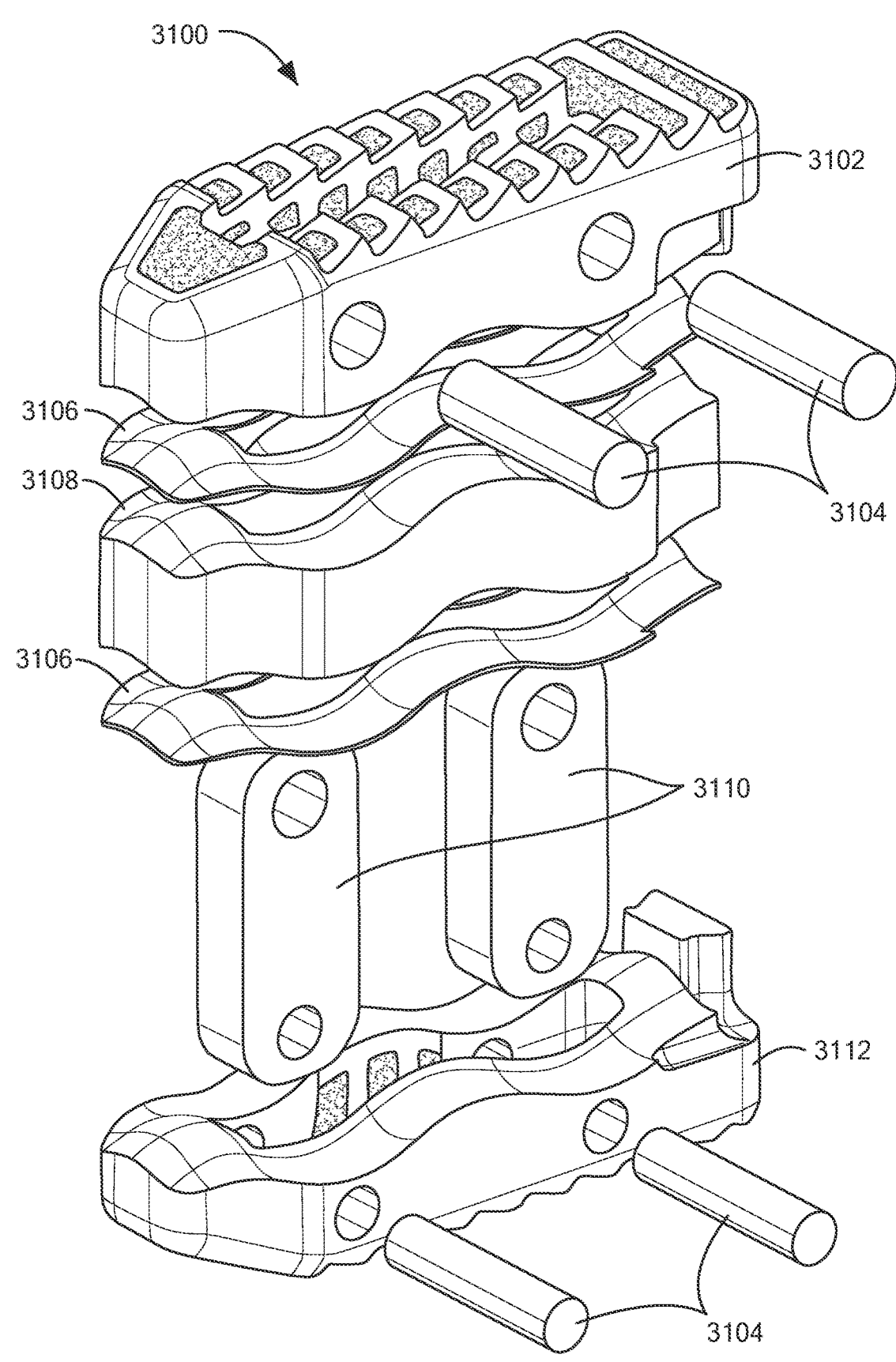
FIG. 31 is an exploded view of a "3 piece" piezoelectric spinal implant, in accordance with an embodiment of the invention.

Referring now to FIG. 31, an exploded view of an embodiment of a piezoelectric spinal implant 3100 (which may be called a spinal interbody) is shown. The spinal implant 3100 comprises a top endplate 3102 which may have machined holes through its sides and a plurality of teeth or other protrusions extending from its upper, i.e., outer, surface. The top endplate 3102 may have a bottom, or inner, surface that has undulations, waves, zig-zags, or another non-planar structural geometry that distributes compressive or shear forces applied to the endplate unevenly to a piezo-electric material 3106. The bottom endplate 3112 may similarly have a non-planar inner surface that distributes forces unevenly to a piezoelectric material and a plurality of teeth or protrusions on its outer, or bottom, surface. The bottom endplate 3112 may also have machined holes through its sides. The spinal implant 3100 may also comprise assembly pins 3104, which are configured to slot into the machined holes on the top endplate 3102 and the bottom endplate 3112, and further into connecting brackets 3110. The piezoelectric components 3106 may be configured to provide an electrical output that corresponds to a load applied to the outer surfaces of the top and bottom endplates. The top and bottom endplates may also be called first and second endplates, and may be made of an insulating material or a conductive material. They may be attached to a first and second vertebra, respectively. The connecting brackets 3110 may be made of an insulating material or a conductive material.

The piezoelectric components 3106 may be substantially planar in shape prior to assembly, and deformed into a non-planar shape, such as having undulations, waves, zig-zags, curves, creases, and/or bends, due to the application of a force to the top and bottom endplates. The piezoelectric components 3106 may conform to the inner surfaces of the endplates and the upper and bottom surfaces of the cage body 3108. The force may be the force applied due to assembly, a compression force, (such as a spinal compression force) or a shear force, or a combination of such forces. The force may be about 10 N, 25 N, 50 N, 100 N, 200 N, 500 N, 700 N, 1000 N, 1500 N, 3000 N, 5000 N, or 10,000 N. The force may be variable and range between an upper and lower bound. The electrical output may include a voltage of about 0.1 mV, 0.3 mV, 0.5 mV, 1 mV, 10 mV, 25 mV, 100 mV, 200 mV, 500 mV, 700 mV, 1 V, 2 V, 3 V, 4 V, 5 V, 6 V, 7 V, 10 V, 15 V, or 20 V. The electrical voltage output may be variable and range between an upper and lower bound. The electrical output may include a current of about 50 nA, 100 nA, 500 nA, 1000 nA, 3000 nA, 5000 nA, 7000 nA, 10,000 nA, 50,000 nA, 100,000 nA, 250,000 nA, 500,000 nA, 750,000 nA, 1 mA, 5 mA, 10 mA, 15 mA, 25 mA, 35 mA, or 50 mA. The electrical current output may be variable and range between an upper and lower bound. All ranges between any of the above values are hereby disclosed.

The spinal implant 3100 also comprises a cage body 3108 (a.k.a. intermediate body, or middle layer). The cage body 3108 may be made of an insulating material or a conductive material. It may have top and bottom surfaces with undulations, waves, zig-zags, curves, bends, creases, or other non-planar structural geometry. Such non-planar structural geometry may cause or further assist the piezoelectric component(s) 3106 to have non-planar shapes when a force is applied to the top and bottom endplates.

Figure 32A:
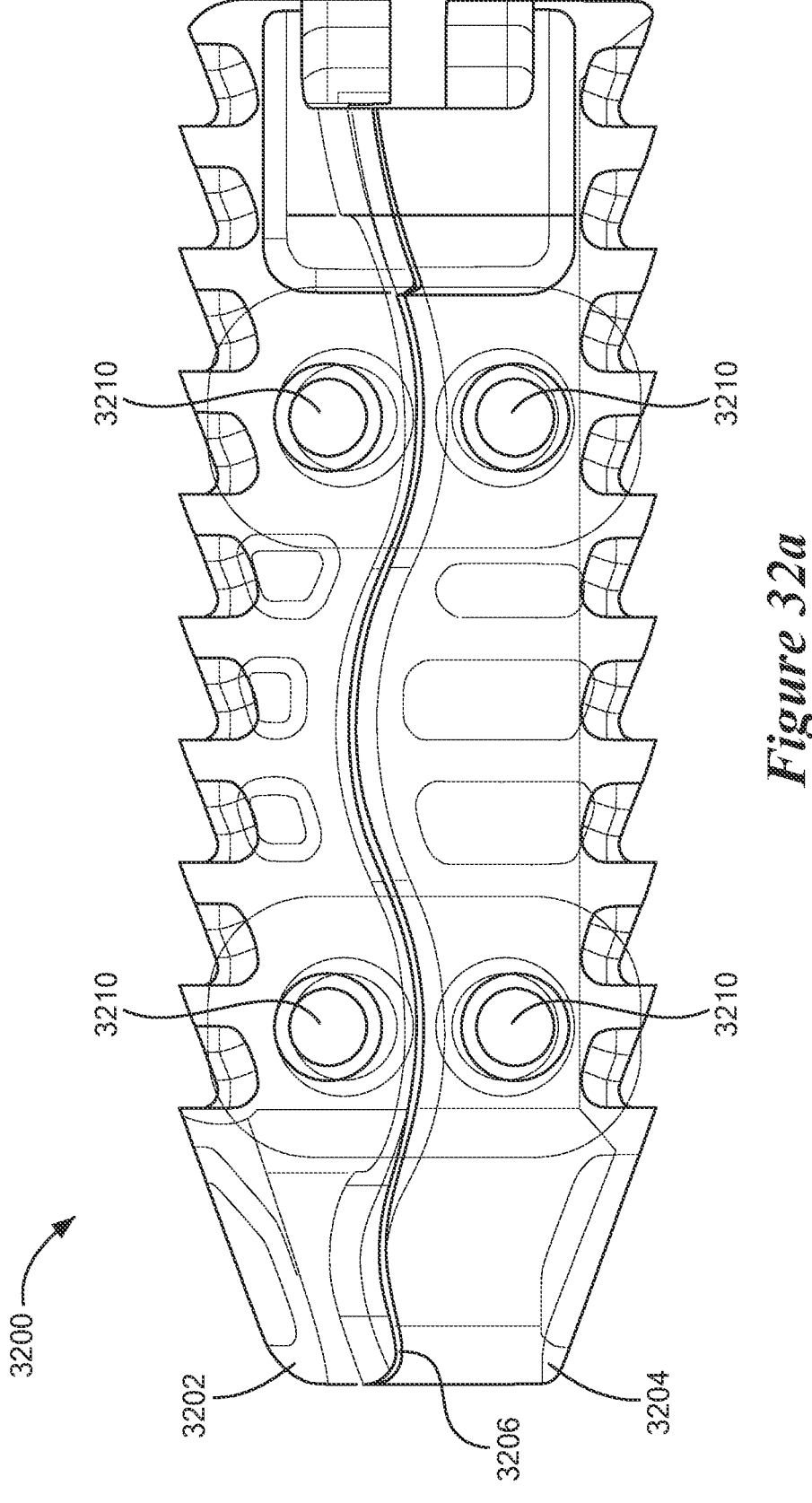
FIGS. 32*a* & 32*b* are an assembled and exploded view of a "2 piece" piezoelectric spinal implant, in accordance with an embodiment of the invention.
Figure 32B:
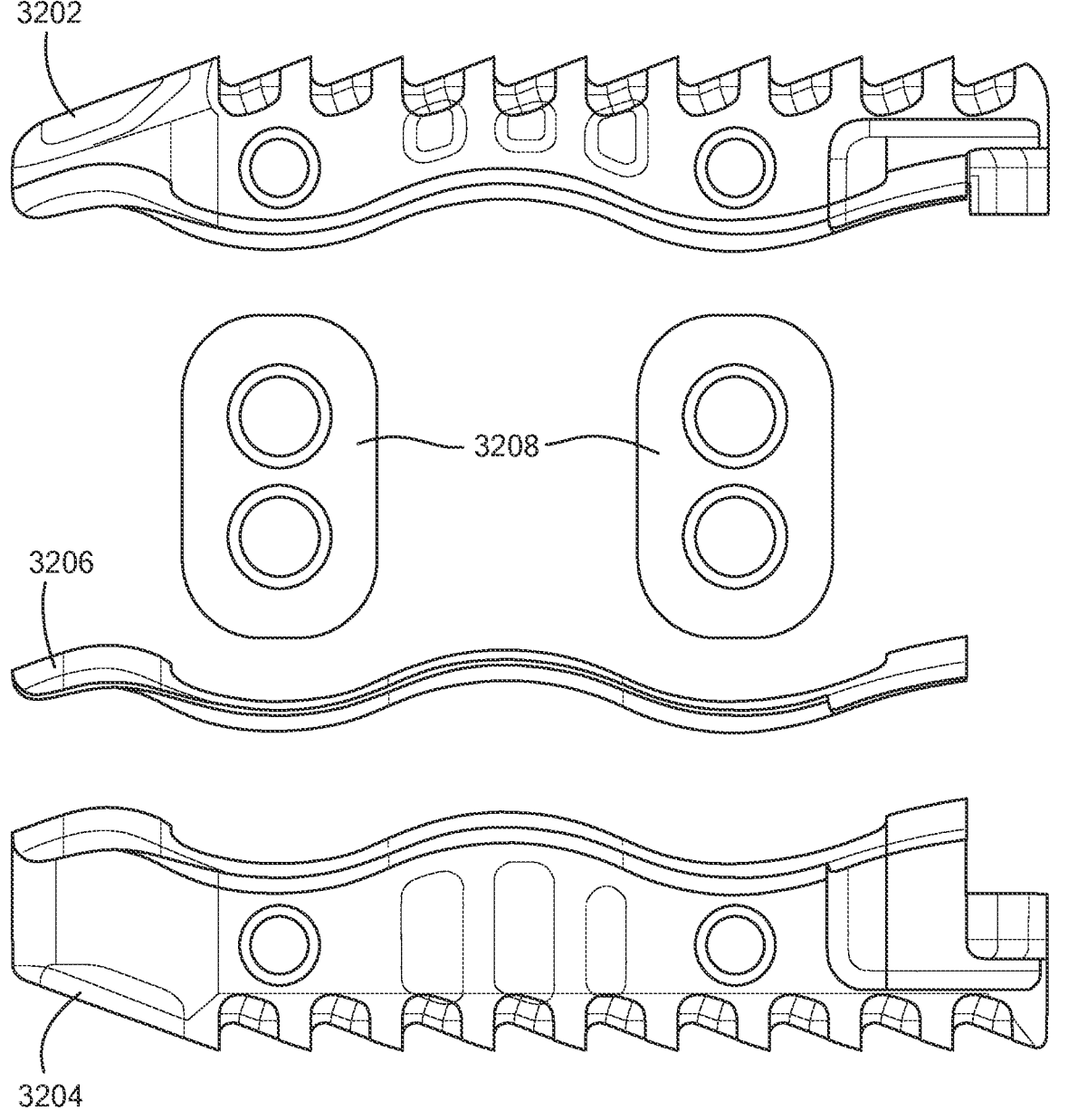

Referring now to FIGS. 32*a* and 32*b*, an embodiment of a piezoelectric spinal implant 3200 is shown. FIG. 32*a* shows an assembled implant and FIG. 32*b* shows an exploded view of the implant. This embodiment comprises a top endplate 3202, a bottom endplate 3204, a single piezoelectric component 3206, connecting brackets 3208, and assembly pins 3210. These components may be similar to components described in relation to FIG. 31.

Figure 33A:
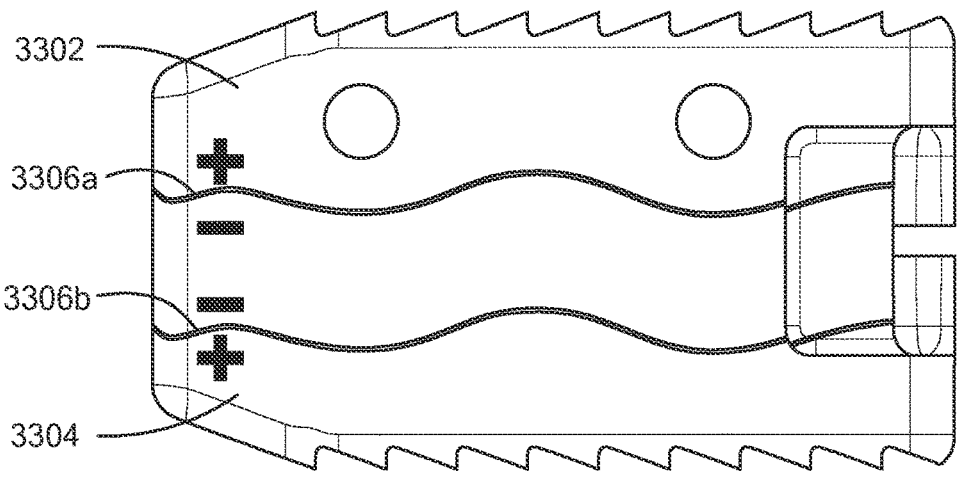
FIGS. 33*a*, 33*b* & 33*c* are views of a piezoelectric spinal implant with piezoelectric components in varying orientations, in accordance with an embodiment of the invention.
Figure 33B:
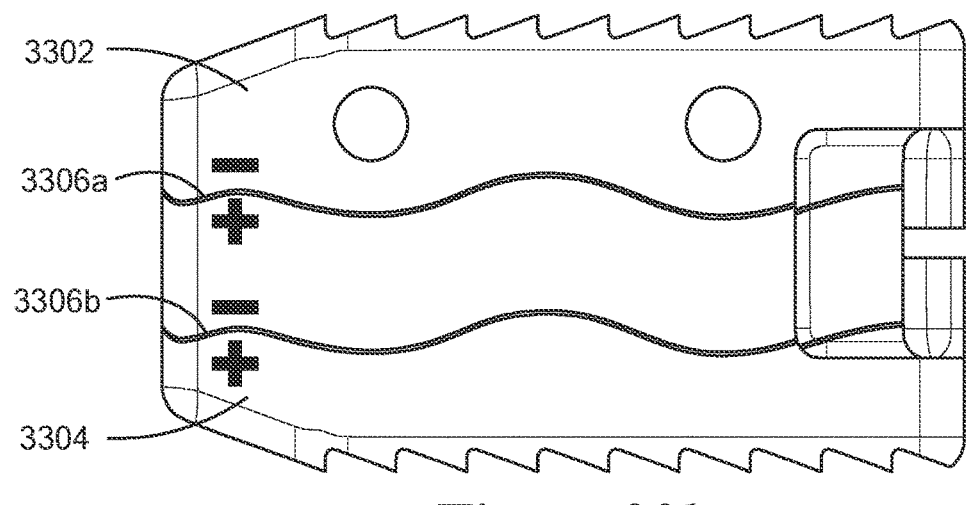
Figure 33C:
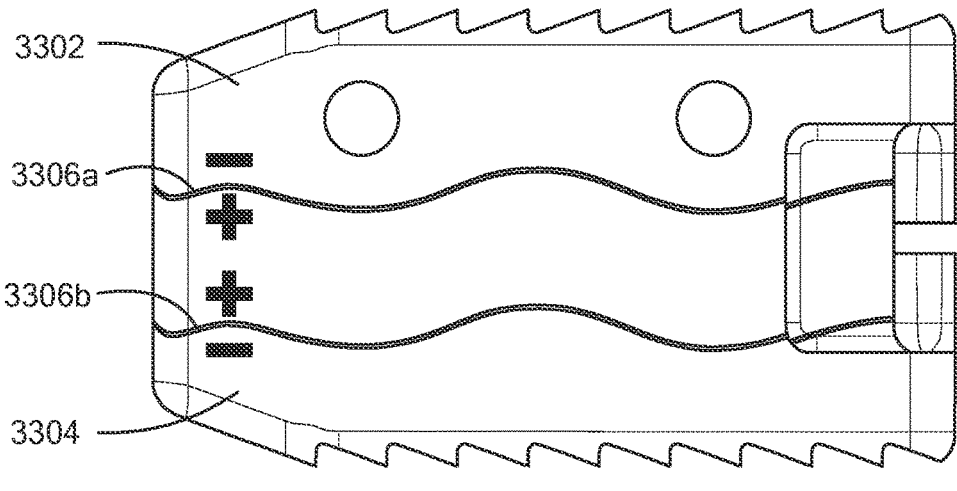

Referring now to FIGS. 33*a*, 33*b*, and 33*c*, several embodiments of a piezoelectric spinal implant are shown. The spinal implant comprises top endplate 3302, bottom endplate 3304, and piezoelectric components 3306*a* and 3306*b*. As shown by the figures, the piezoelectric components may be disposed in any orientation of positive and negative. Other embodiments may also have piezoelectric components in various orientations of positive and negative.

Figure 34A:
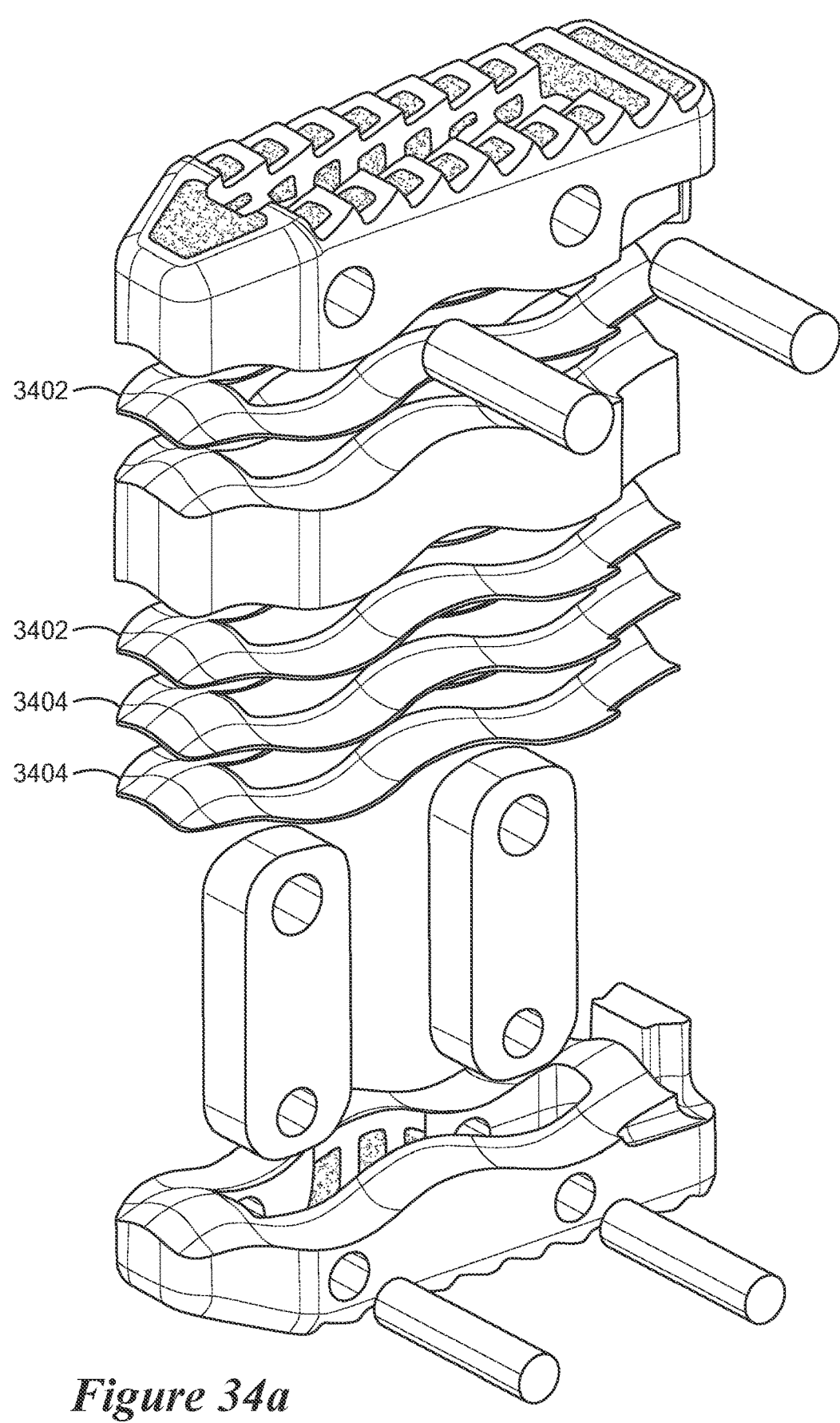
FIGS. 34*a* & 34*b* are exploded views of piezoelectric spinal implants with piezoelectric components comprised of one or more layers, in accordance with an embodiment of the invention.
Figure 34B:
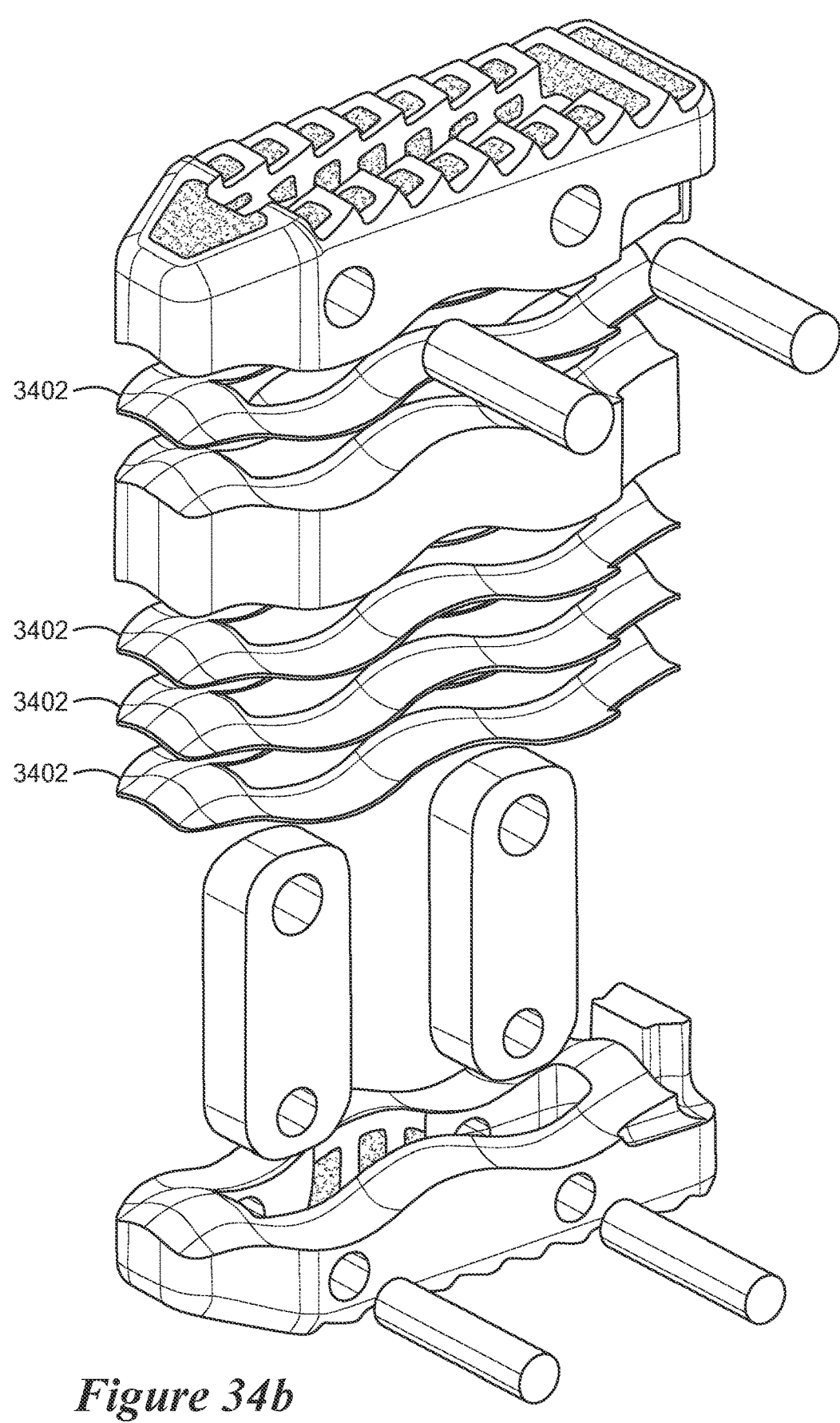

Referring now to FIGS. 34*a* and 34*b*, several embodiments of a piezoelectric spinal implant are shown. These embodiments comprise piezoelectric components made up of at least one layer. These layers may be piezoelectric layers 3402 or non-piezoelectric layers 3404. The non-piezoelectric layers 3404 would act as an insulator. For each piezoelectric component there are one or more piezoelectric layers, like shown in FIG. 34*b*, and there may be zero, one, or more than one non-piezoelectric layers like shown in FIG. 34*a*. The piezoelectric layers may be a piezoelectric polymer, and the non-piezoelectric layers may be a non-piezoelectric polymer.

Figure 35:
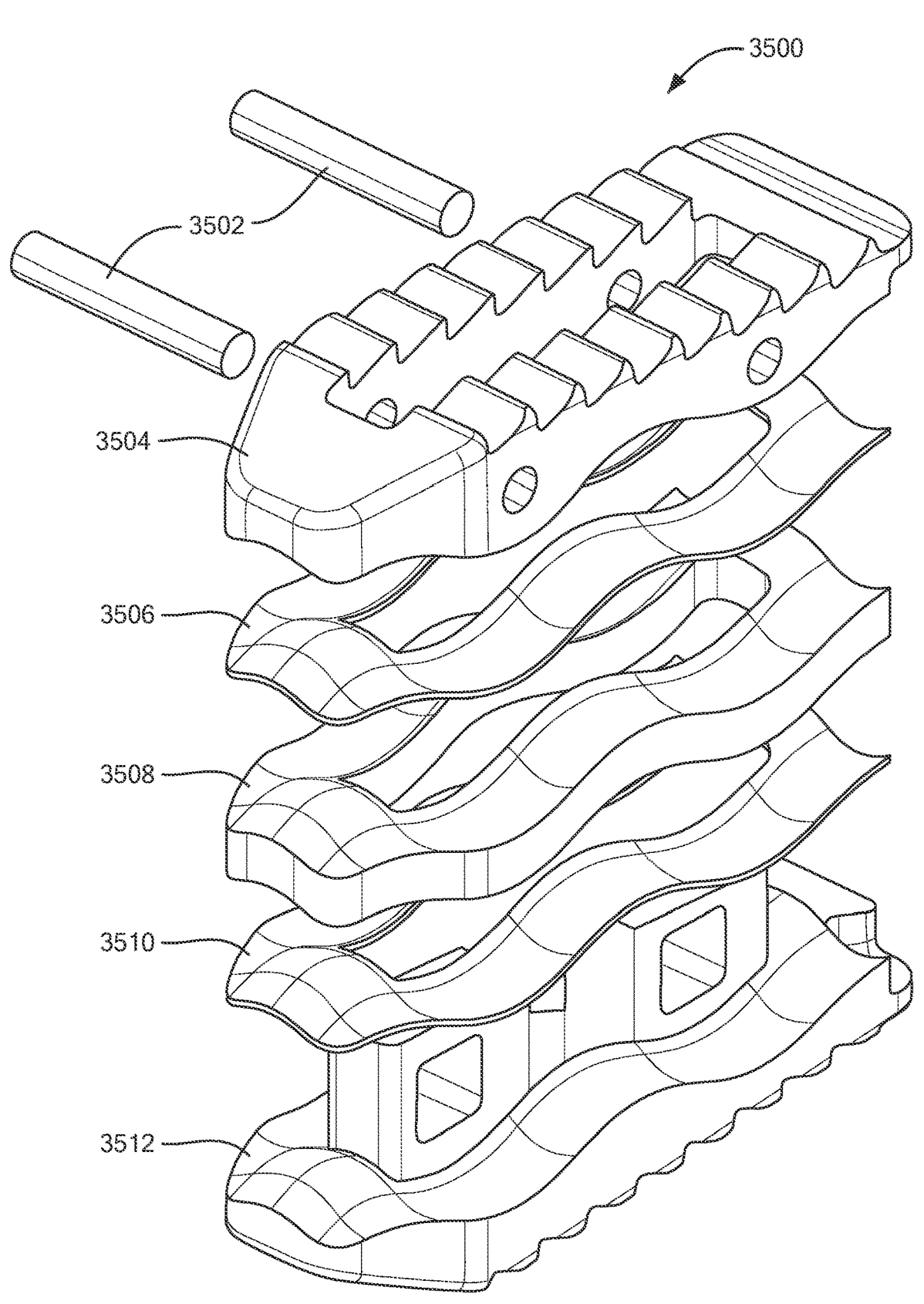
FIG. 35 is an exploded view of another embodiment of a "3 piece" piezoelectric spinal implant, in accordance with an embodiment of the invention.

Referring now to FIG. 35, an embodiment of a piezoelectric spinal implant 3500 is shown. The implant 3500 contains: assembly pins 3502 made of machined titanium or another suitable material; a top endplate 3504 made of 3D-printed titanium which has a contoured bottom surface; a piezoelectric component 3506 that deforms to the contours during assembly and that strains under compressive or shear load to produce electric output; an intermediate insulator body 3508 made of PEEK (polyetheretherketone) or another suitable insulator that has contoured top and bottom surfaces to match the endplate inner surfaces; a second piezoelectric component 3510 that deforms to the contours during assembly and that strains under compressive or shear load to produce electric output; and a bottom endplate 3512 made of 3D-printed titanium, with a contoured top surface, and with connecting components configured to receive the assembly pins 3502 in order to hold the assembled implant together.

Figure 36A:
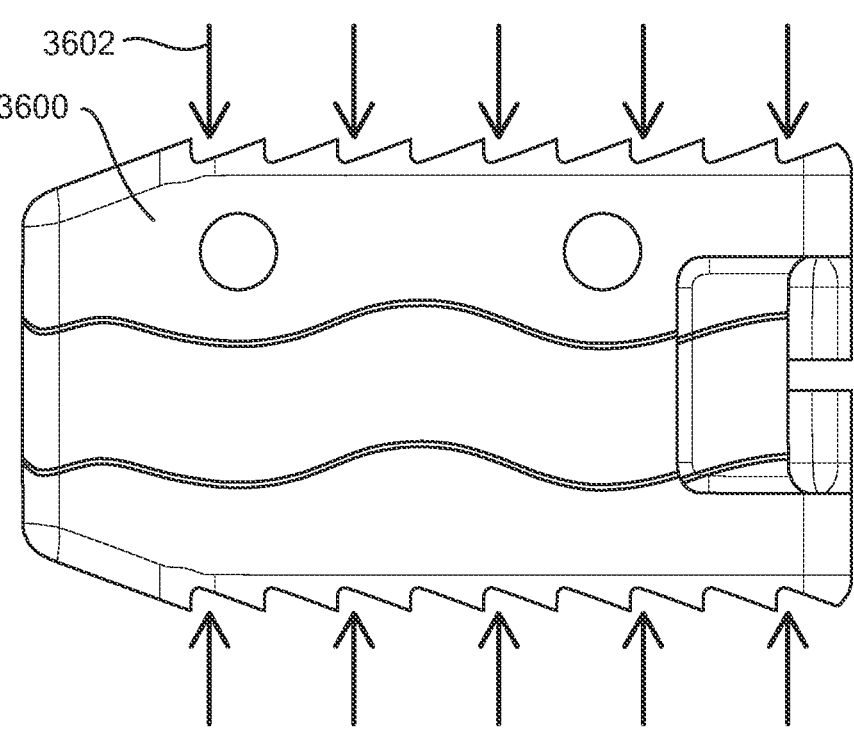
FIGS. 36*a* & 36*b* show piezoelectric spinal implants under compressive and shear loads, in accordance with an embodiment of the invention.
Figure 36B:
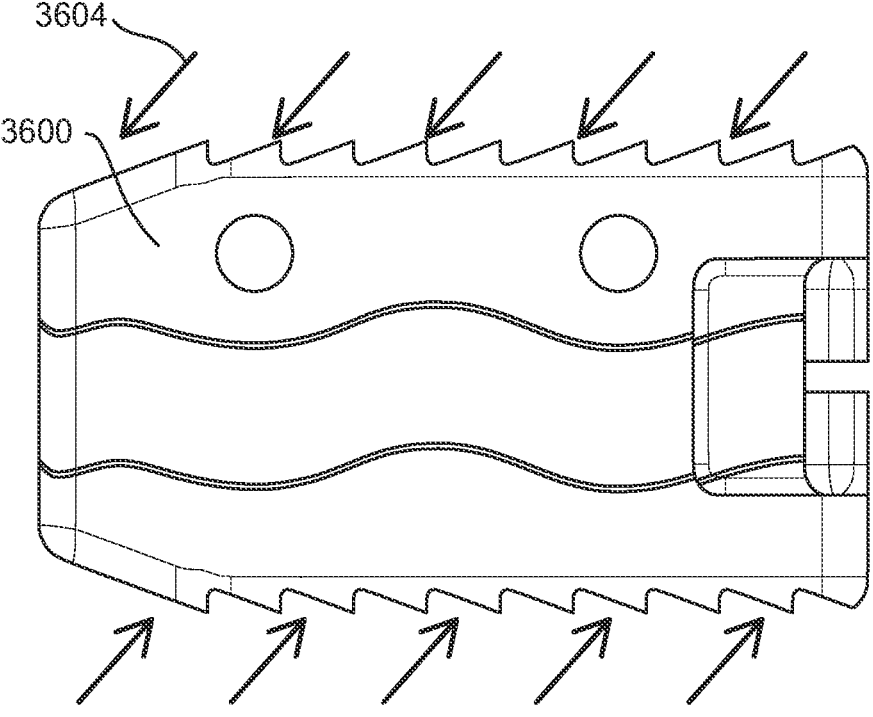

Referring now to FIGS. 36*a* and 36*b*, an embodiment of a piezoelectric spinal implant 3600 is shown under load. In FIG. 36*a*, the implant 3600 is under a compressive load. Compressive forces 3602 are acting upon the top and bottom surfaces of the implant 3600. In FIG. 36*b*, the implant is under a shear load. Shear forces, or forces that have a shear component, 3604 are acting upon the top and bottom surfaces of the implant 3600. Both compressive (or axial) loading and shear loading of the implant can activate the piezoelectric component(s). These forces may be spinal forces the implant sees while implanted between vertebrae.

Figure 37A:
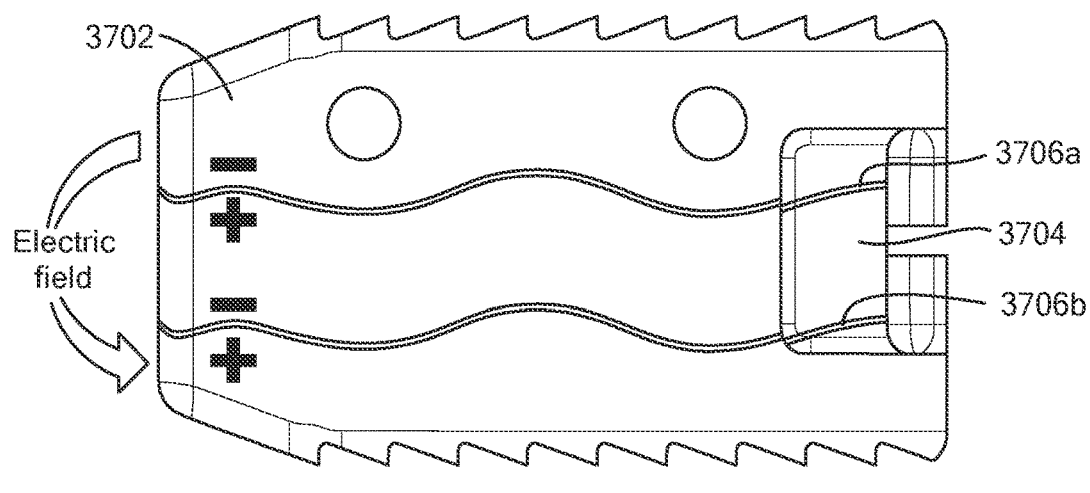
FIGS. 37*a*, 37*b* & 37*c* show piezoelectric spinal implants with piezoelectric components in varying orientations generating differing electric fields, in accordance with an embodiment of the invention.
Figure 37B:
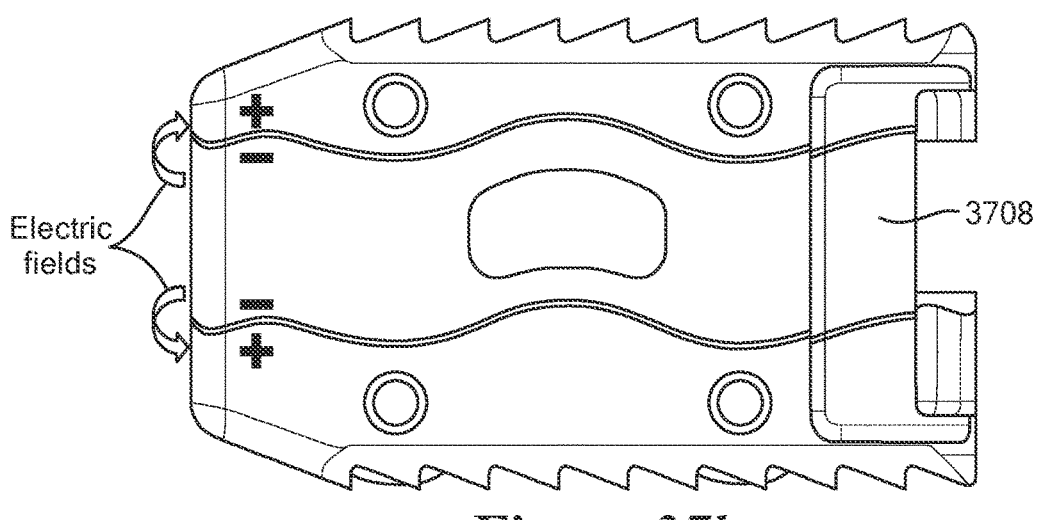
Figure 37C:
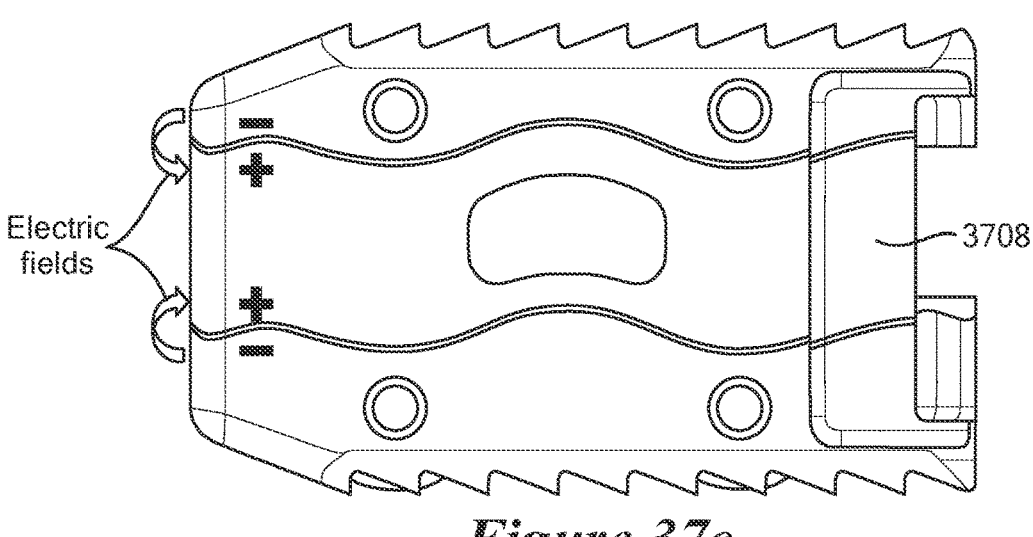

Referring now to FIGS. 37*a*, 37*b*, and 37*c*, several embodiments of a piezoelectric spinal implant are shown. In FIG. 37*a*, the spinal implant is configured with piezoelectric components 3706*a* and 3706*b* in a matching orientation, wherein the negative side is oriented towards the top of the implant 3702. In FIG. 37*a*, the intermediate body 3704 is acting as an insulator, while the endplates are acting as conductors. The configuration of FIG. 37*a* results in a large electric field spanning from the top endplate to the bottom endplate. It is also contemplated that the configuration of the piezoelectric components 3706*a* & *b* may be reversed, which would result in an electric field of reversed direction. In FIGS. 37*b* and 37*c*, the spinal implant is configured such that the piezoelectric components are in opposite or mirrored orientations, and the intermediate body 3708 is a conductor. This results in multiple smaller electric fields as shown.

Figure 38:
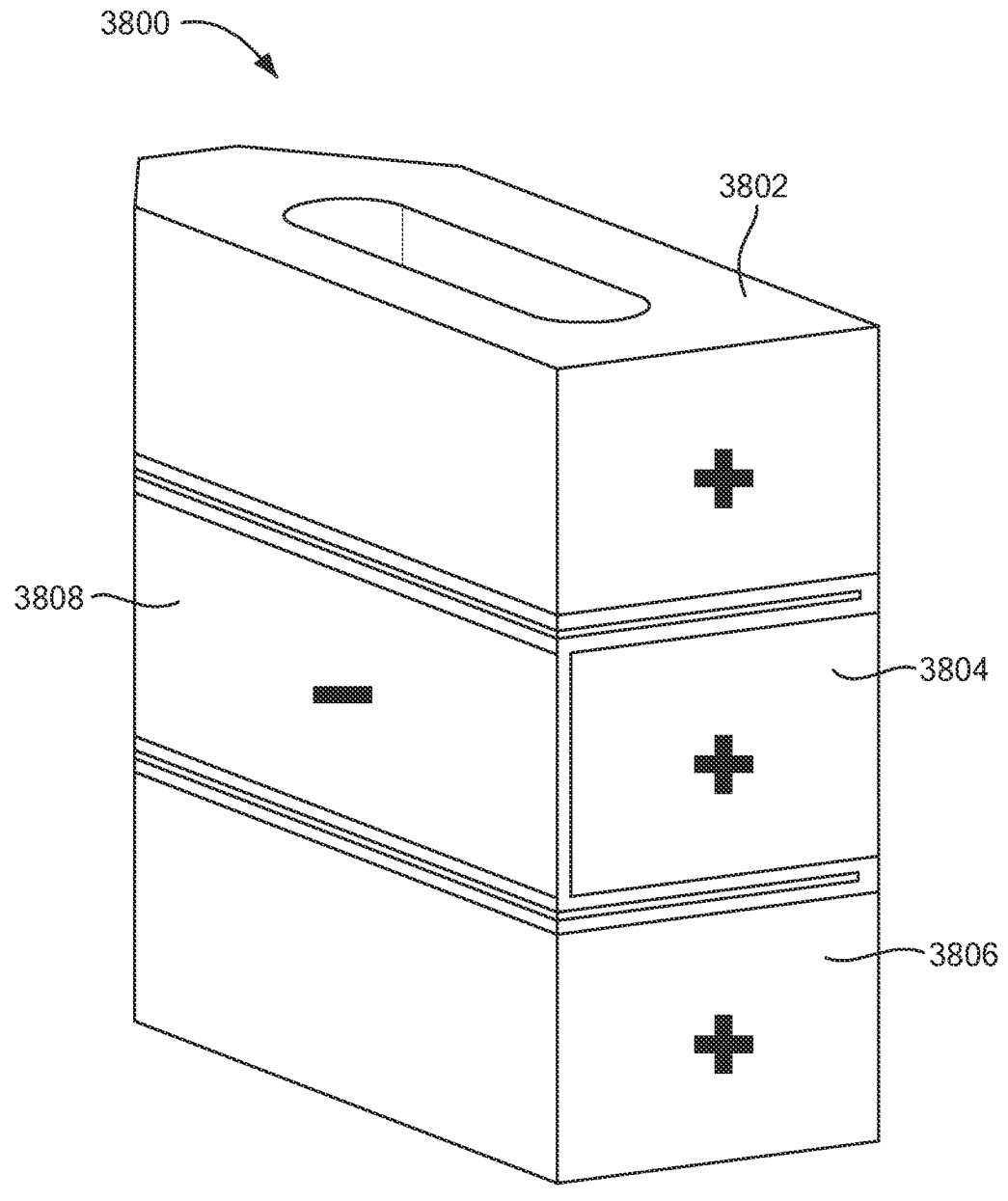
FIG. 38 is a piezoelectric spinal implant with a wrapped or folded piezoelectric component, in accordance with an embodiment of the invention.

Referring now to FIG. 38, an embodiment of a piezoelectric spinal implant 3800 is shown. In this embodiment, the implant 3800 comprises a top endplate 3802, a bottom endplate 3806, an intermediate body 3804, and a piezoelectric component 3808 folded and/or wrapped around the intermediate body 3804.

Figures 39A, 39B:
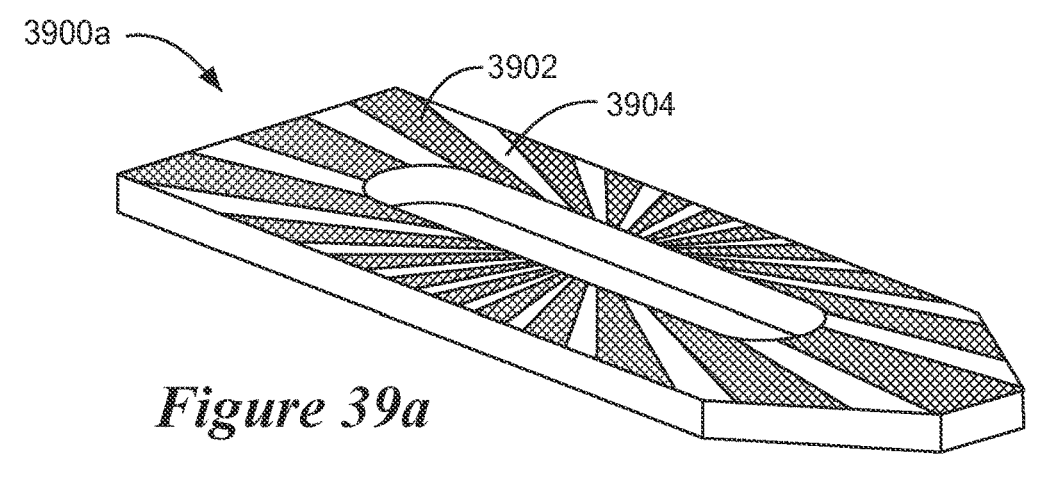
FIGS. 39*a* & 39*b* show a selectively conductive piezoelectric component and the same disposed in a spinal implant generating electric fields, in accordance with an embodiment of the invention.

Referring now to FIGS. 39*a* and 39*b*, an embodiment of a piezoelectric spinal implant 3900*b* is shown in which the piezoelectric component 3900*a* is selectively metalized or piezoelectrically neutralized (a.k.a. selectively conductive). Surface property changes may be made with metal surface applications or other conductive material to make select areas conductive, or by using laser treatment or other surface energy altering methodologies to remove piezoelectric properties in treated areas.

In FIG. 39*a*, the dark stripes 3902 represent piezoelectric portions of the component 3900*a*, and the light stripes 3904 represent non-piezoelectric portions. In FIG. 39*b*, spinal implant 3900*b* comprises a top endplate 3906, selectively metalized piezoelectric component 3900*a*, intermediate body 3912, second piezoelectric component 3914 (which may also be selectively metalized), bottom endplate 3916, and connecting bracket 3908. The selective metallization of piezoelectric component 3900*a* provides an electric field 3910 along multiples areas along the edge to give a more uniform distribution of electric output.

Figure 40A:
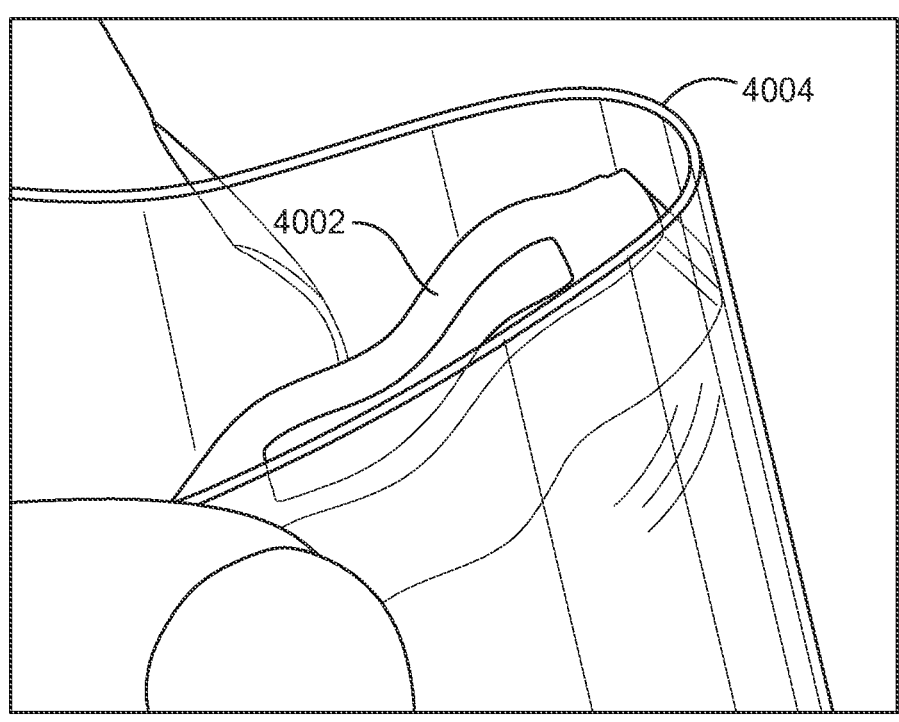
FIGS. 40*a* & 40*b* show a piezoelectric polymer wrapped around a spinal implant component, in accordance with an embodiment of the invention.
Figure 40B:
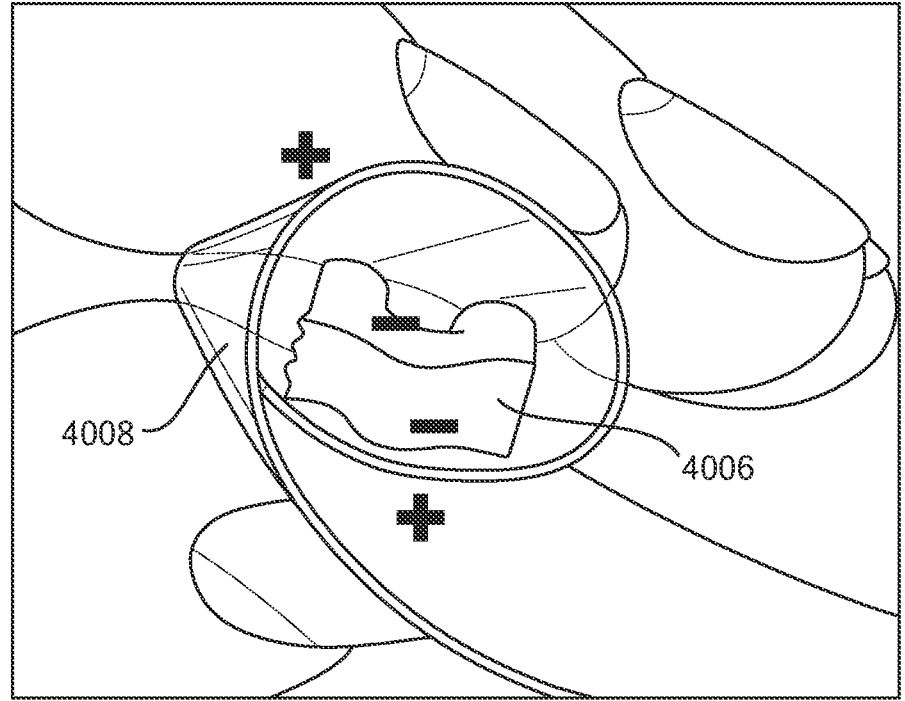

Referring now to FIGS. 40*a* and 40*b*, piezoelectric polymer (or other material) may be seen wrapped around a structural implant component, such as an endplate or intermediate body, in accordance with various embodiments of the invention. In FIG. 40*a*, piezoelectric polymer 4004 is being wrapped around side walls of an implant component. In FIG. 40*b*, piezoelectric polymer 4008 is being wrapped around the top, bottom, and side walls of an implant component.

Figure 41A:
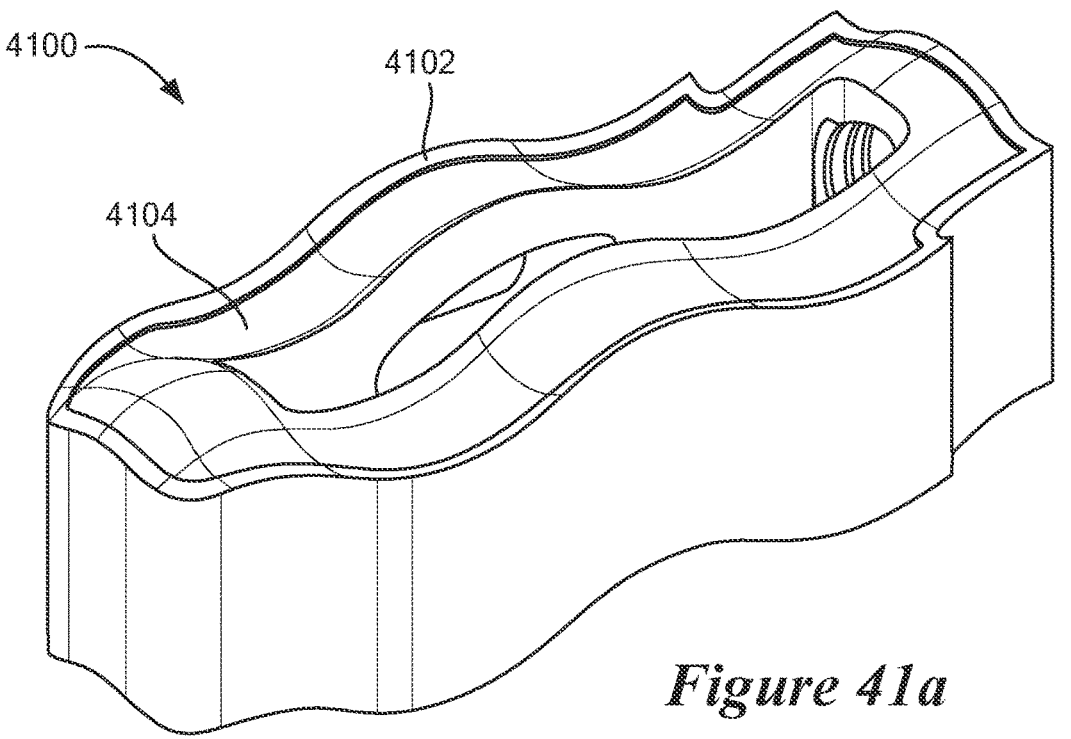
FIGS. 41*a*, 41*b* & 41*c* show an intermediate member of a piezoelectric spinal implant having an insulated outer surface and a conductive interior, in accordance with an embodiment of the invention.
Figure 41B:
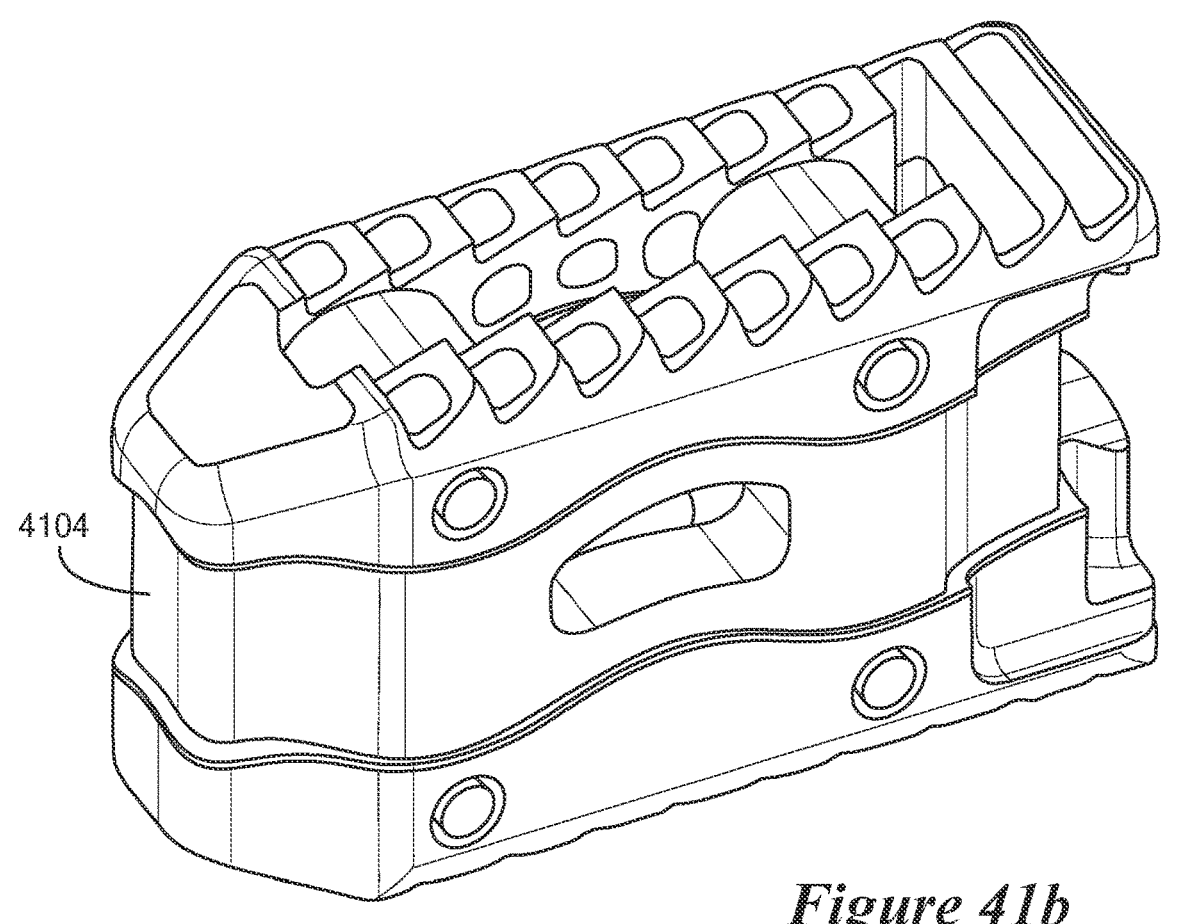
Figure 41C:
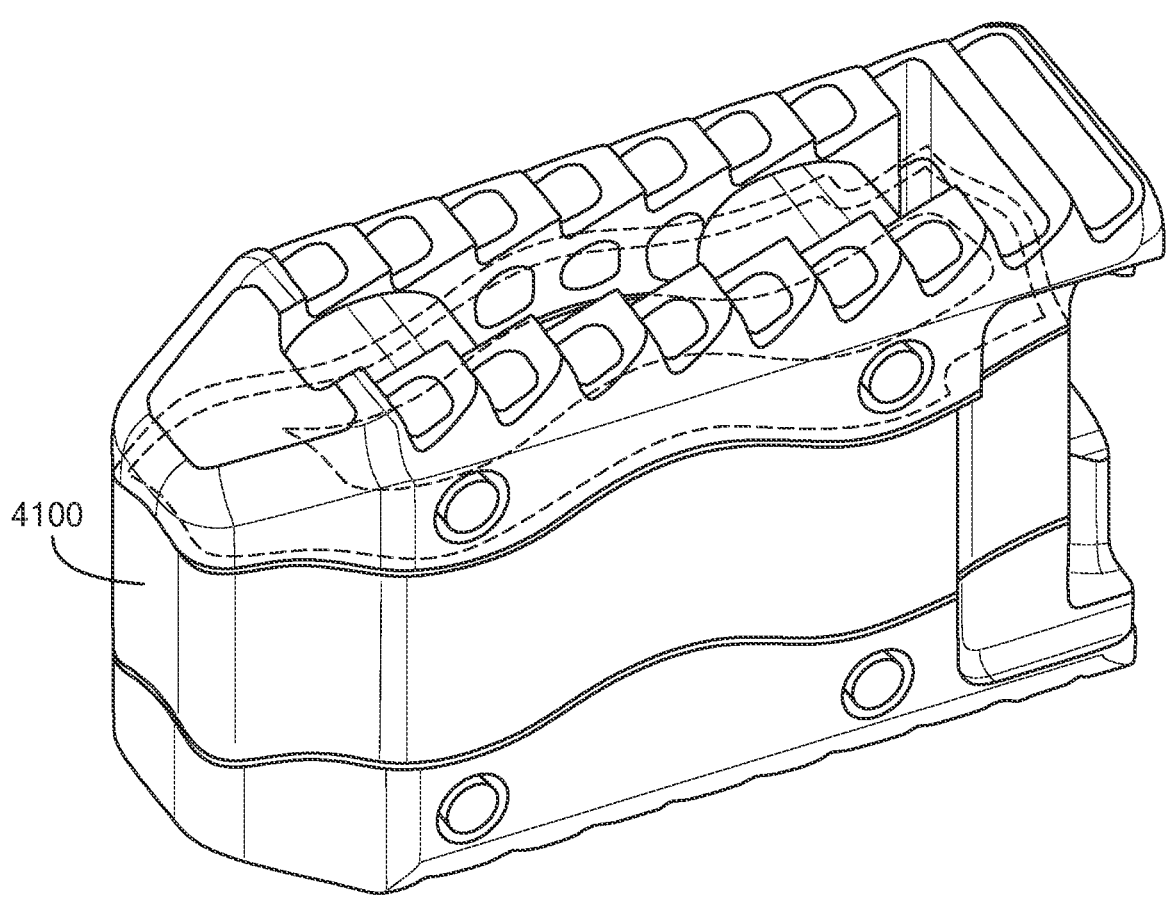

Referring now to FIGS. 41*a*, 41*b*, and 41*c*, an intermediate body 4100 is shown, in accordance with various embodiments of the invention. FIG. 41*a* shows intermediate body 4100 having a conductive inner portion 4104 and an insulted outer portion (or shell) 4102. The insulated outer portion 4102 can be used to change the electric field produced by piezoelectric components. FIG. 41*b* shows a piezoelectric spinal implant with inner portion 4104 of the intermediate body exposed. FIG. 41*c* shows a piezoelectric spinal implant with insulated outer portion 4102 of the intermediate body exposed.

Figure 42:
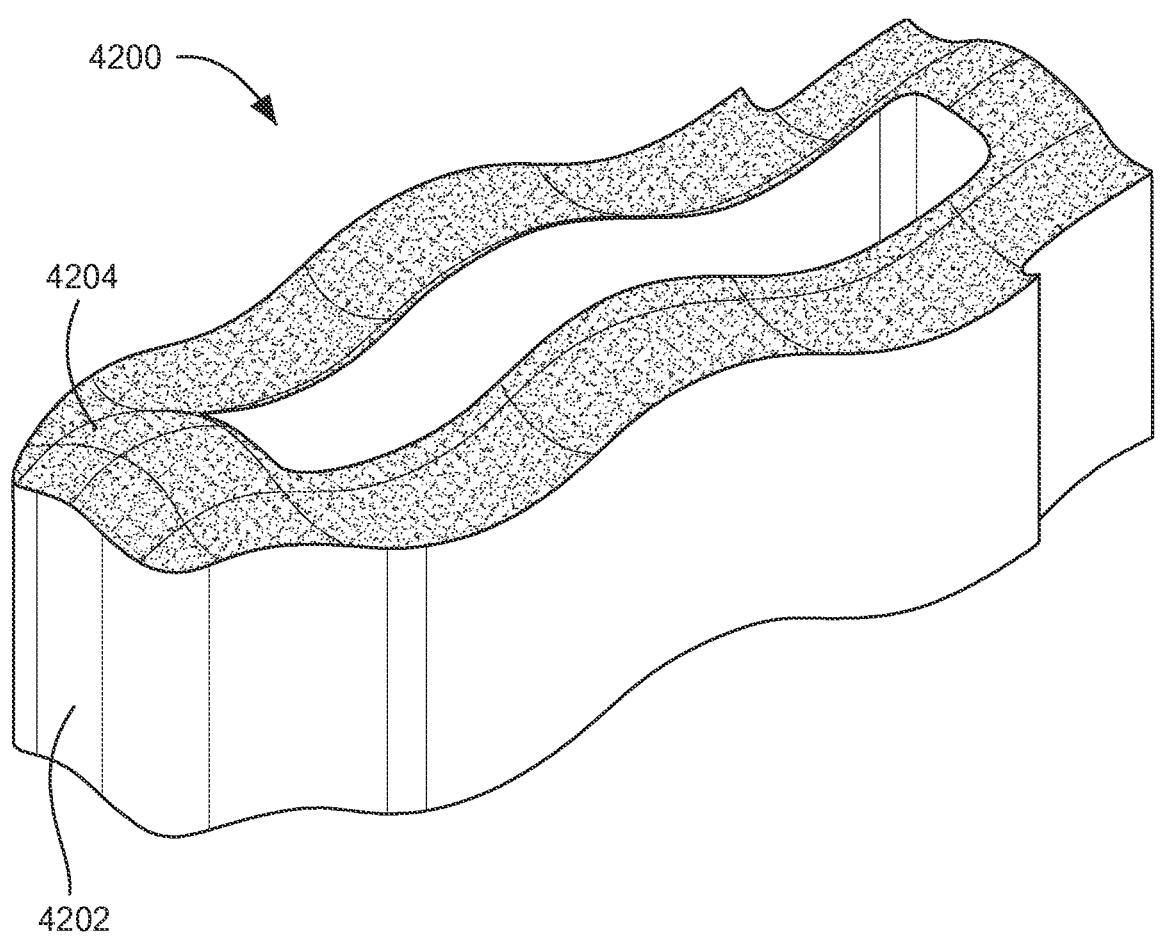
FIG. 42 shows an intermediate member made of an insulating material having a conductive coating, in accordance with an embodiment of the invention.

Referring now to FIG. 42, an intermediate body 4200 is shown, in accordance with an embodiment of the invention. The intermediate body 4200 comprises a PEEK body 4202, with a titanium coated top surface 4204. The bottom surface (not shown) may also be titanium coated. The titanium coated PEEK surfaces may draw energy from the entire surface of the piezoelectric layer.

Figure 43:
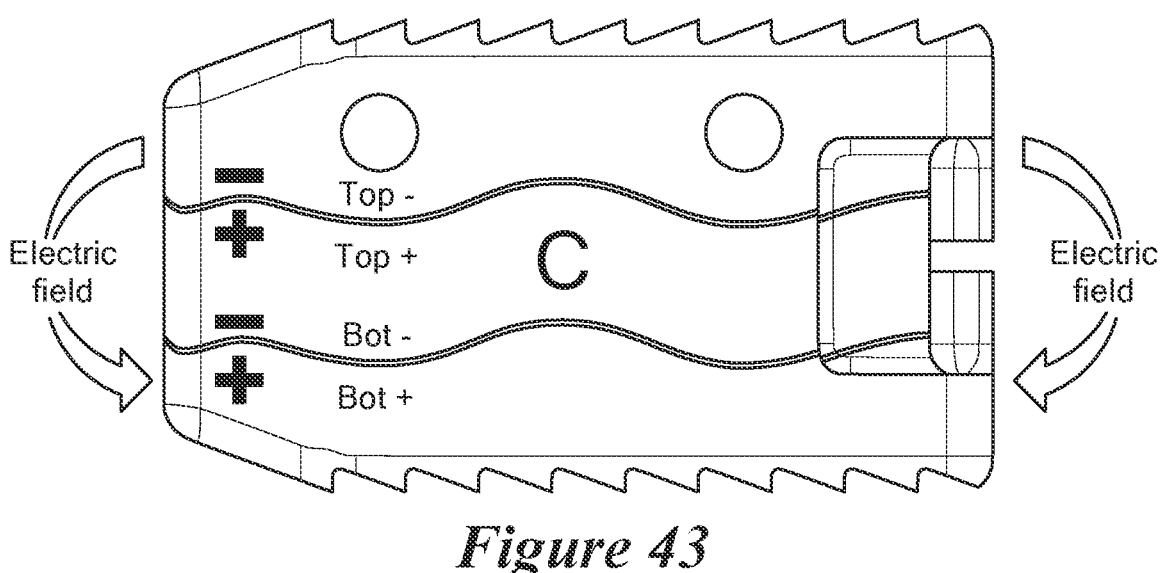
FIG. 43 shows a configuration of a piezoelectric spinal implant producing electric fields, in accordance with an embodiment of the invention.

Referring now to FIG. 43, a piezoelectric spinal implant is shown in accordance with an embodiment of the invention. The piezoelectric components are configured with negative sides facing upwards and positive sides facing downwards. The intermediate body is an insulator, as indicated by the "C", such that an electric field as shown is created to transverse the gap between the positively and negatively charged endplates when the piezoelectric components are activated.

Figure 44A:
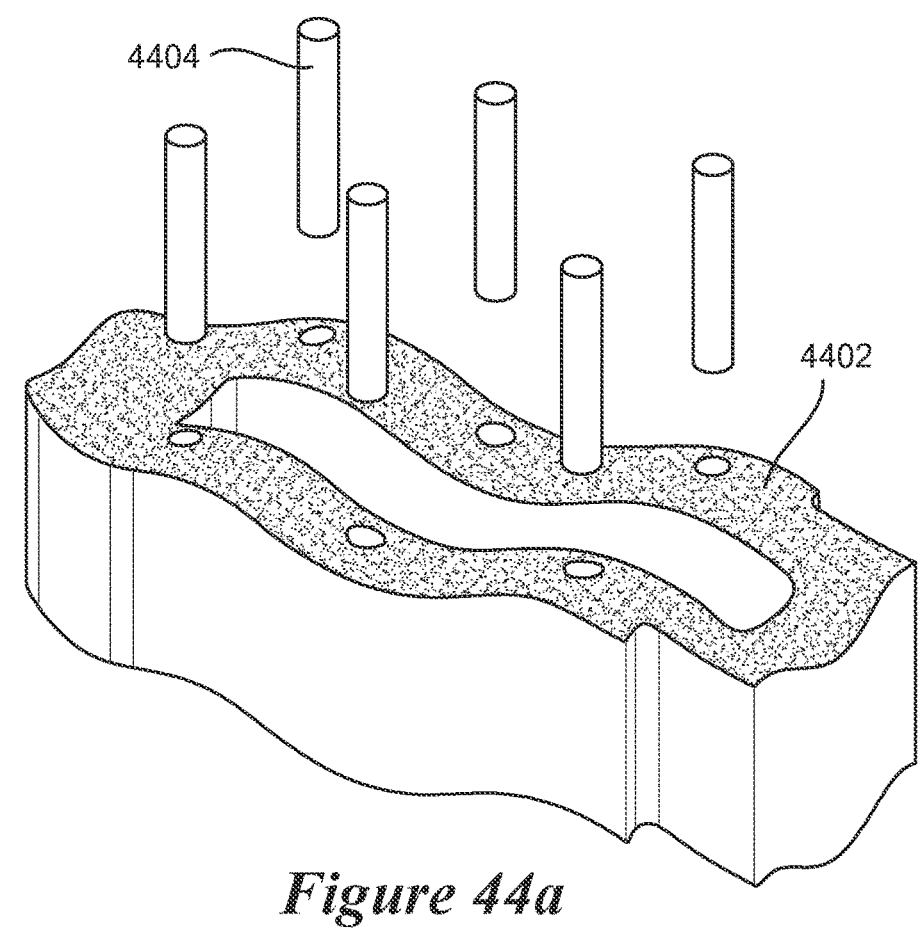
FIGS. 44*a* & 44*b* show an intermediate member having conductive pins and/or a conductively coated lumen, in accordance with an embodiment of the invention.
Figure 44B:
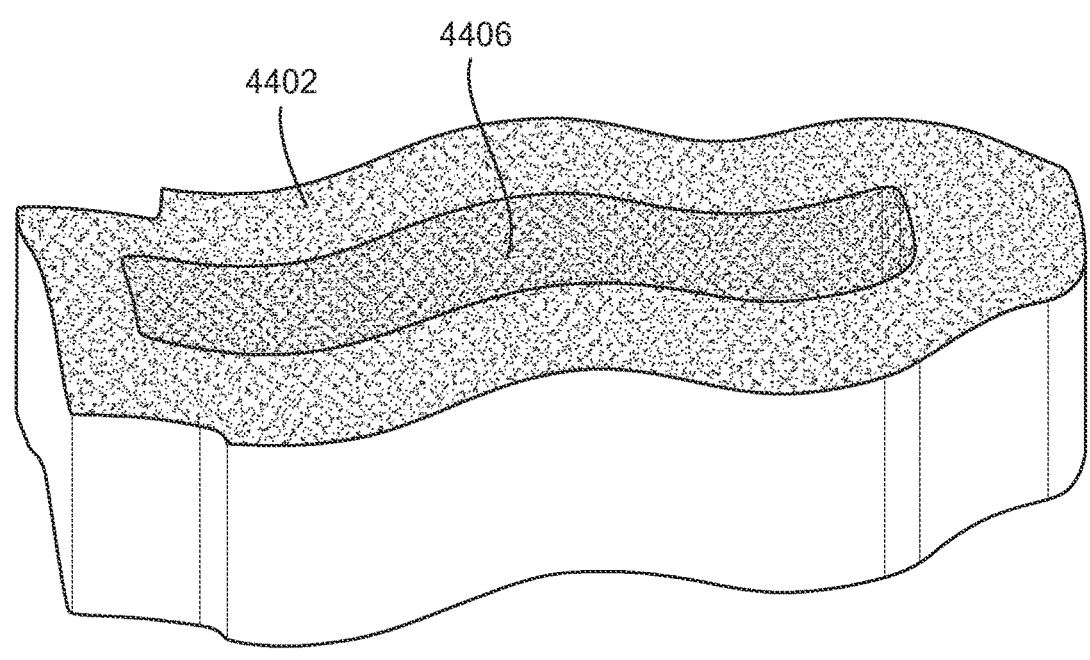

Referring now to FIGS. 44*a* and 44*b*, embodiments of intermediate bodies are shown. In FIG. 44*a*, titanium pins 4404 run from the top surface to the bottom surface of the titanium coated 4402 PEEK to electrically link [Top+] to [Bot−] of FIG. 43. FIG. 44*b* shows an intermediate body with titanium coating 4402 on its top and bottom (not shown) surfaces and additionally coating the inside of the lumen 4406. The embodiment of FIG. 44*b* may be used in conjunction or alternative with the embodiment of FIG. 44*a* to achieve the electric field effect of FIG. 43.

Figures 45A, 45B:
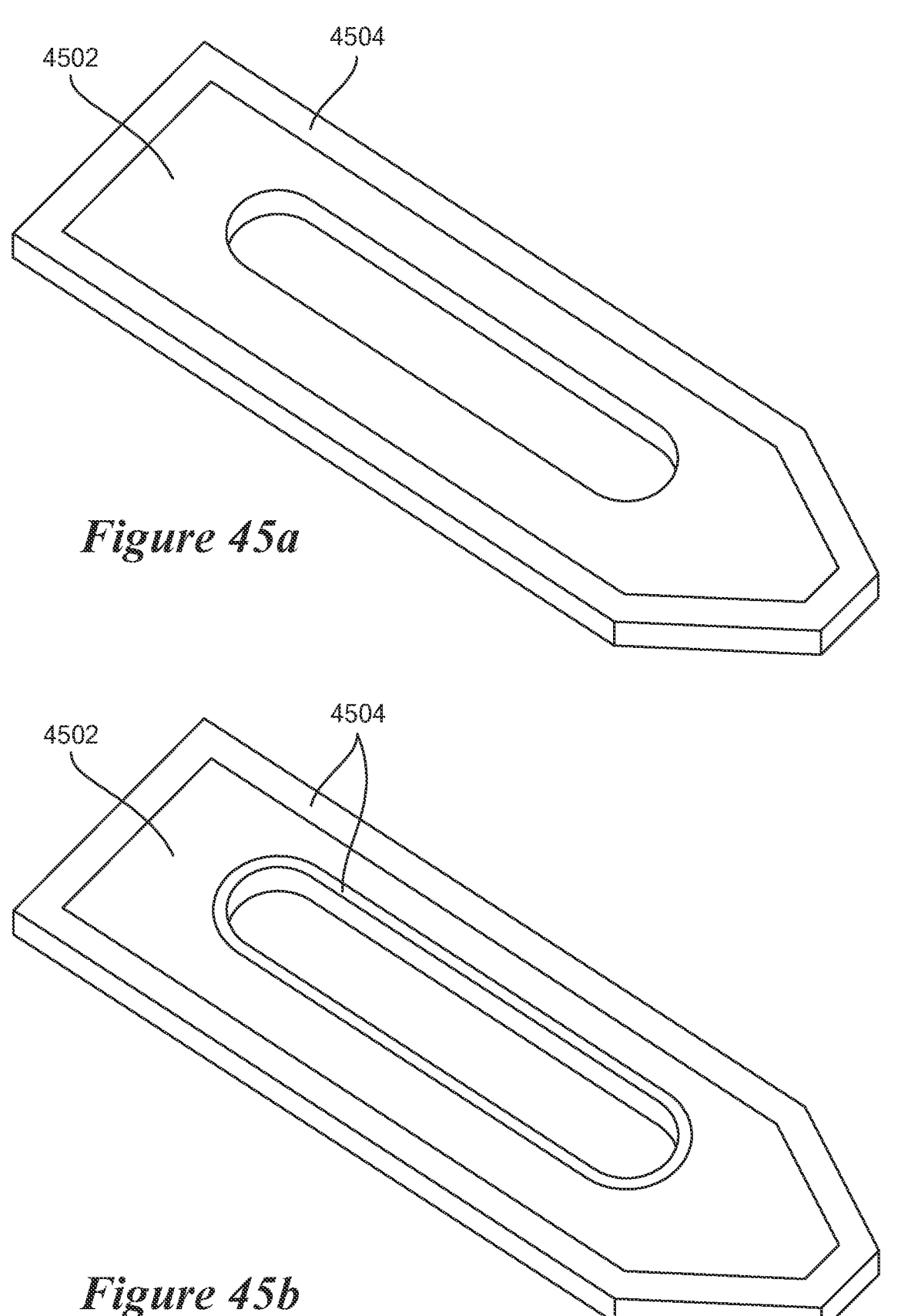
FIGS. 45*a* & 45*b* show selectively conductive piezoelectric components, in accordance with an embodiment of the invention.

Referring now to FIGS. 45*a* and 45*b*, embodiments of selectively conductive piezoelectric components are shown. These embodiments may be selectively metalized or piezoelectrically neutralized by the same processes used in relation to FIG. 39. In FIG. 45*a*, the exterior of the component is insulated, or non-piezoelectric 4504, while the interior of the component is piezoelectric 4502. In FIG. 45*b*, the exterior and interior borders are non-piezoelectric 4504, while the remainder, shown in dark grey, is piezoelectric. This design provides an electric field that is focused along the conductive component and will not short circuit along the periphery.

Figures 46A, 46B:
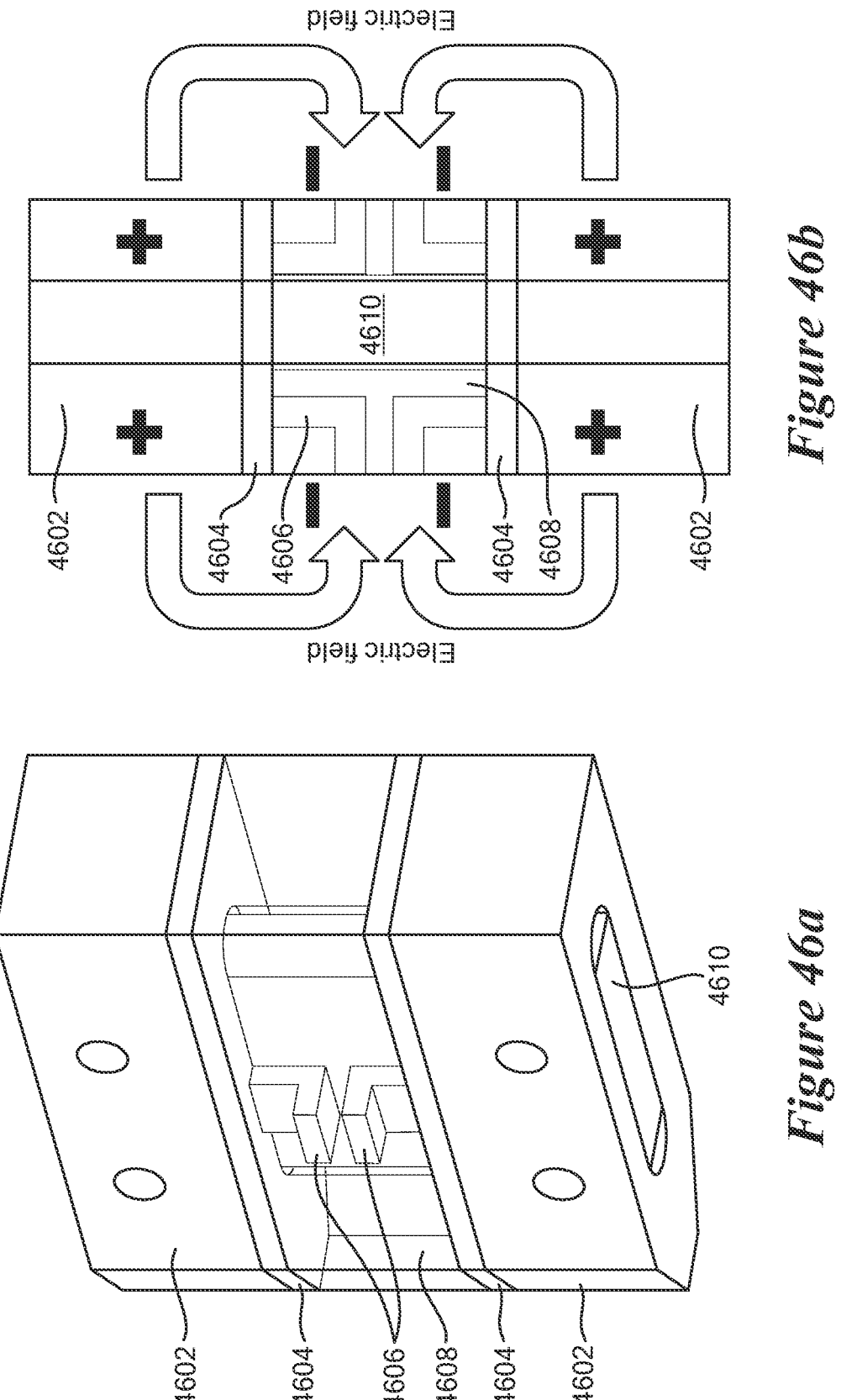
FIGS. 46*a* & 46*b* show an embodiment of a piezoelectric spinal implant with conductive jumpers, in accordance with an embodiment of the invention.

Referring now to FIGS. 46*a* and 46*b*, an embodiment of a piezoelectric spinal implant is shown, comprising additional conductive jumpers 4606. The implant shown in FIG. 46*a* comprises conductive endplates 4602, piezoelectric components 4604, an insulated intermediate body 4608, an inner assembly 4610, and conductive jumpers 4606 further comprising exposed leads that are flush with the exterior surface of the intermediate body. The diagram of FIG. 46*b* further explains this embodiment. The jumpers 4606 are in contact with the negative sides of the piezoelectric components 4604, while the conductive endplates 4602 are in contact with the positive sides of the piezoelectric components 4604, such that current will flow between the positive endplates 4602 and the conductive jumpers 4606 with a high concentration of negative charge, creating an electric field with a large volume. The jumpers 4606 may contact the inner assembly (e.g. a connecting bracket or connecting component) 4610, as shown in the right side of FIG. 46*b* or may be offset and contained internally to the insulated intermediate body 4608, as shown in the left side of FIG. 46*b*.

Figure 47A:
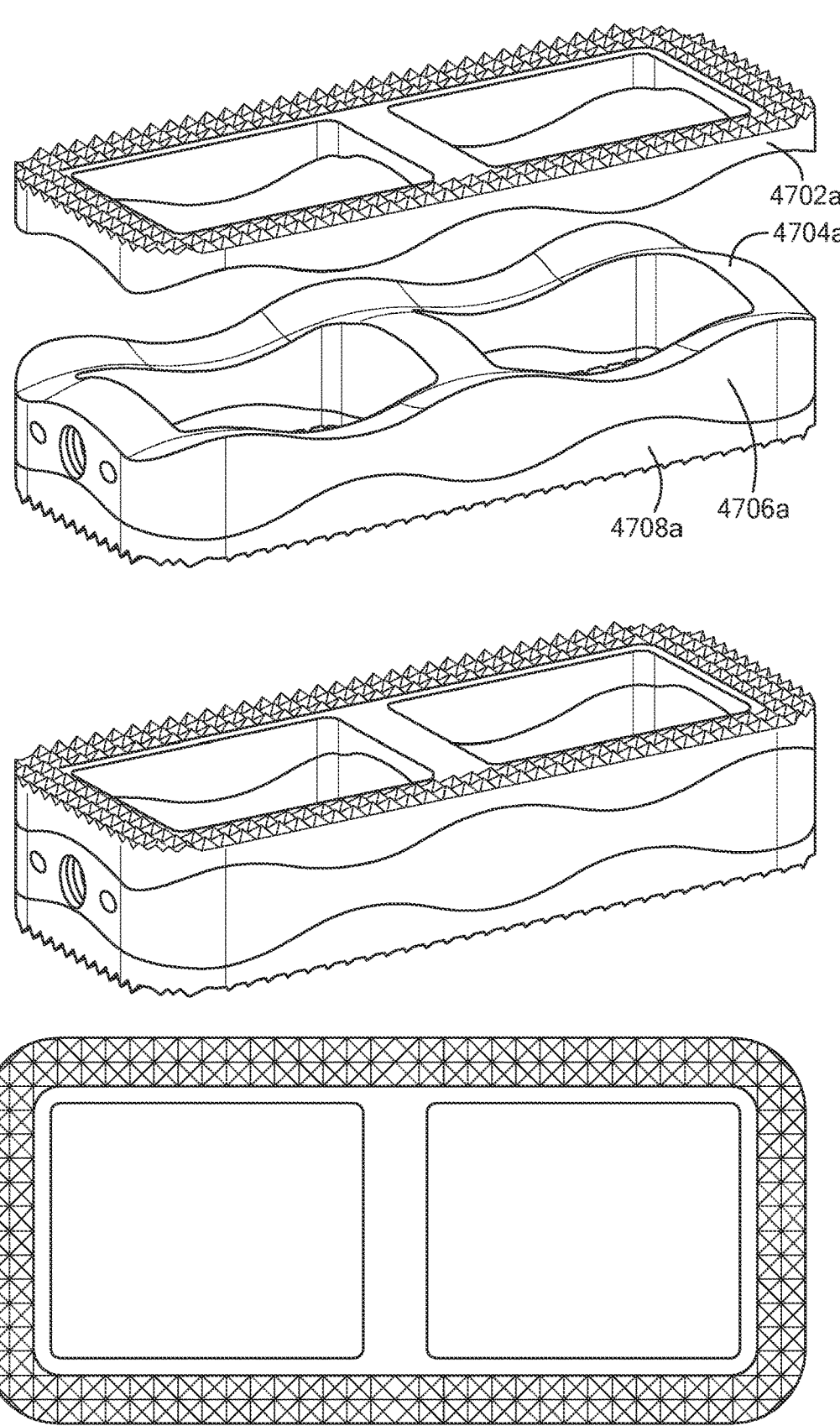
FIGS. 47*a* & 47*b* show piezoelectric spinal implants of varying shapes, in accordance with an embodiment of the invention.
Figure 47B:
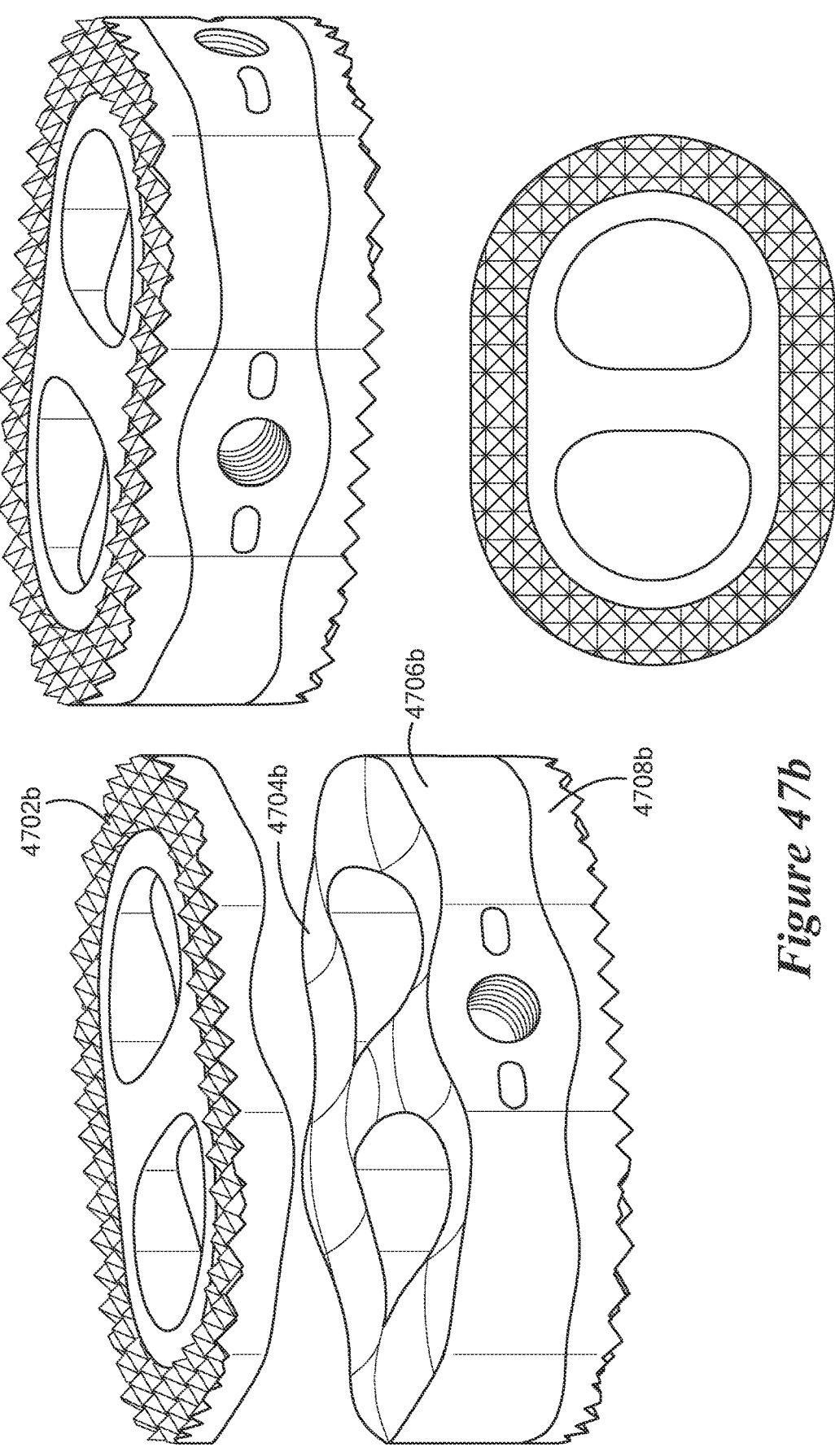

Referring now to FIGS. 47*a* and 47*b*, embodiments of differently shaped piezoelectric spinal implants are shown. Implant assemblies may be a variety of shapes and sizes. Implants according to this disclosure may be ALIF (anterior lumbar interbody fusion) implants, PLIF (posterior lumbar interbody fusion) implants, or L-LIF (lateral lumber interbody fusion) implants. Implants according to this disclosure may also be used in other spinal surgeries including, e.g., cervical and thoracic surgeries.

Figure 48:
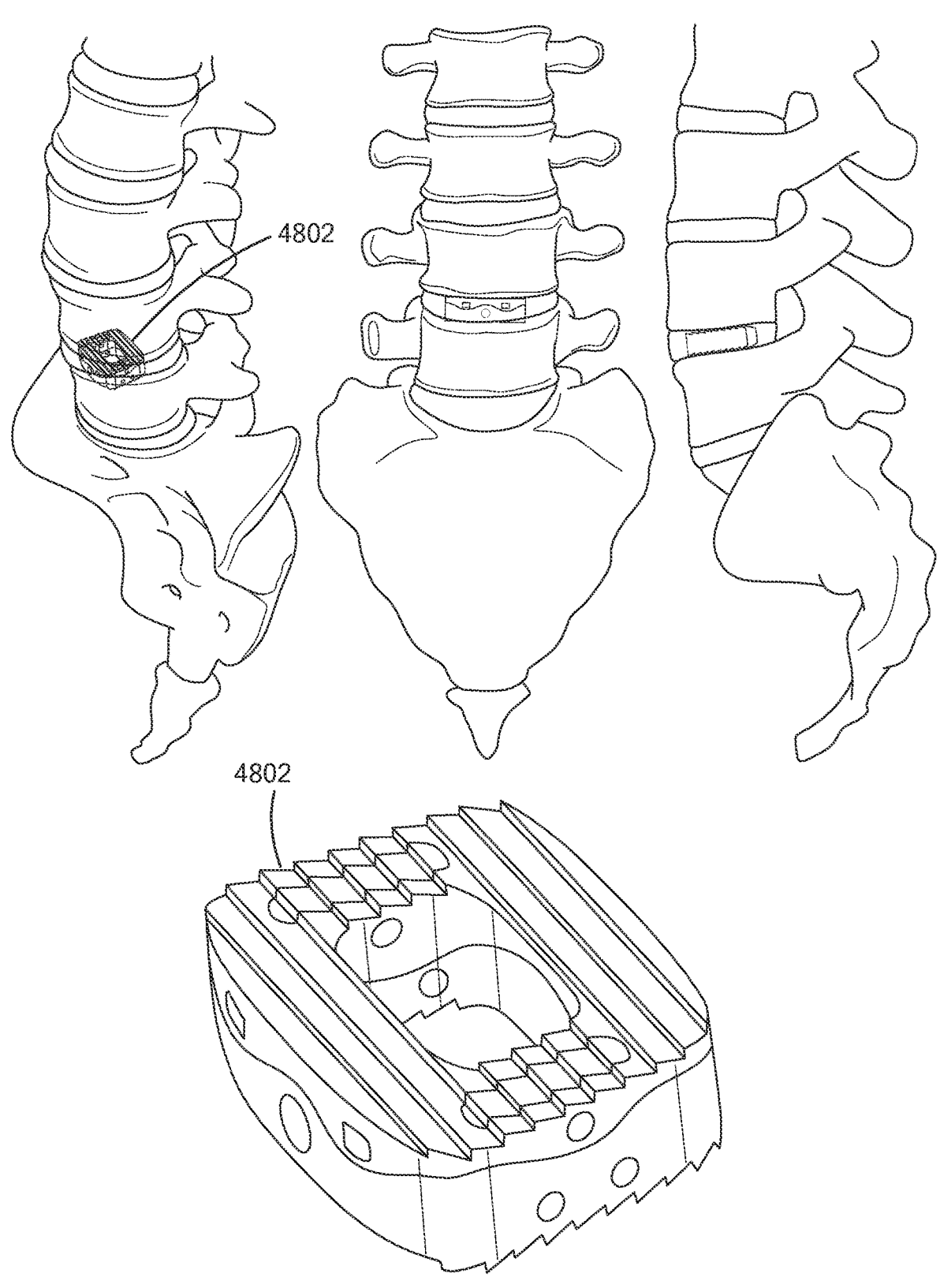
FIG. 48 shows a piezoelectric Anterior Lumbar Interbody Fusion (ALIF) implant, in accordance with an embodiment of the invention.

Referring now to FIG. 48, an embodiment of a piezoelectric ALIF spinal implant 4802 is shown. The implant 4802 is shown disposed between vertebrae in an oblique view, an anterior-posterior view, and a lateral view. A top perspective view of the implant 4802 is also shown.

Figure 49:
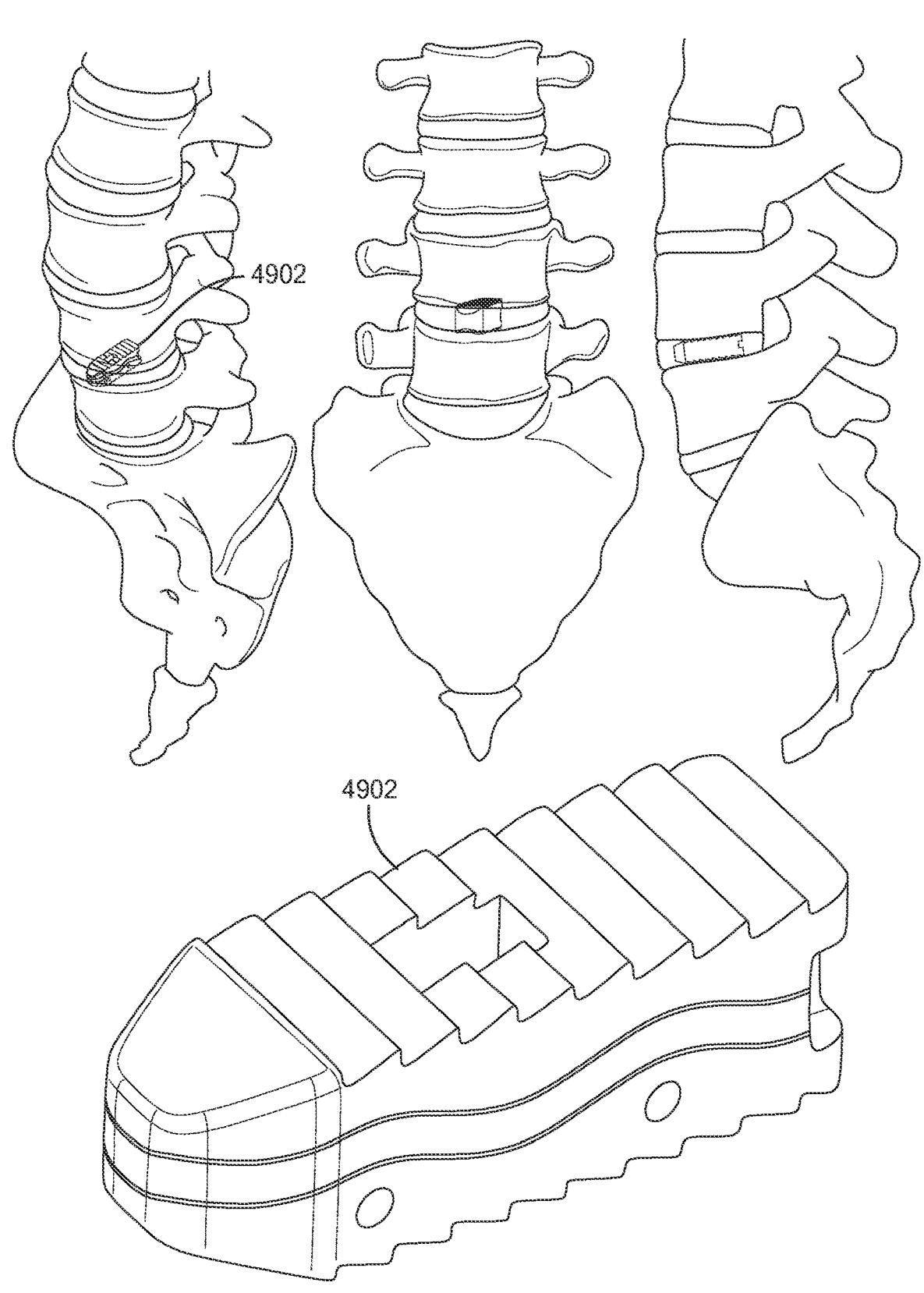
FIG. 49 shows a piezoelectric Posterior Lumbar Interbody Fusion (PLIF) implant, in accordance with an embodiment of the invention.

Referring now to FIG. 49, an embodiment of a piezoelectric PLIF spinal implant 4902 is shown. The implant 4902 is shown disposed between vertebrae in an oblique view, an anterior-posterior view, and a lateral view. A top perspective view of the implant 4902 is also shown.

Figure 50:
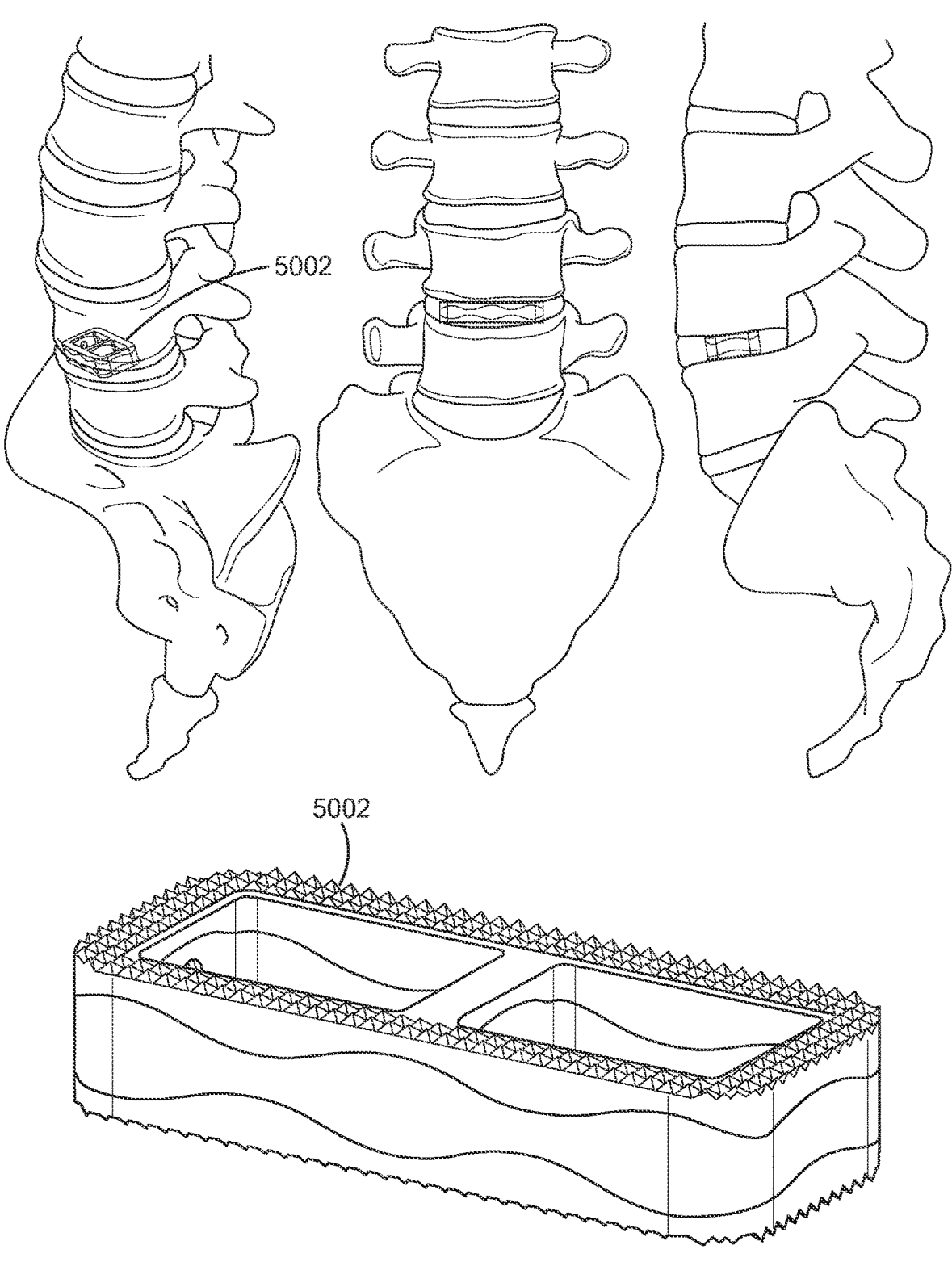
FIG. 50 shows a piezoelectric Lateral Lumbar Interbody Fusion (LLIF) implant, in accordance with an embodiment of the invention.

Referring now to FIG. 50, an embodiment of a piezoelectric L-LIF spinal implant is shown. The implant 5002 is shown disposed between vertebrae in an oblique view, an anterior-posterior view, and a lateral view. A top perspective view of the implant 5002 is also shown.

Figure 51A:
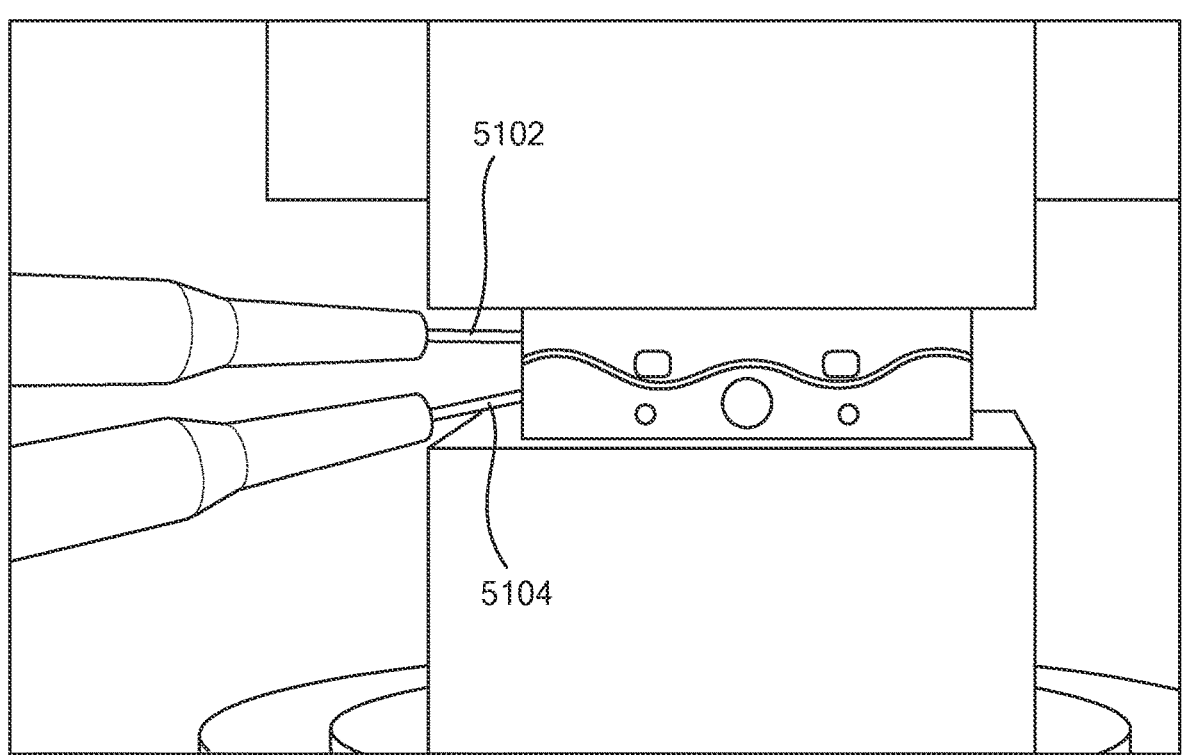
FIGS. 51*a*, 51*b*, and 51*c* show a test configuration and test data of an embodiment of a piezoelectric spinal implant.
Figure 51B:
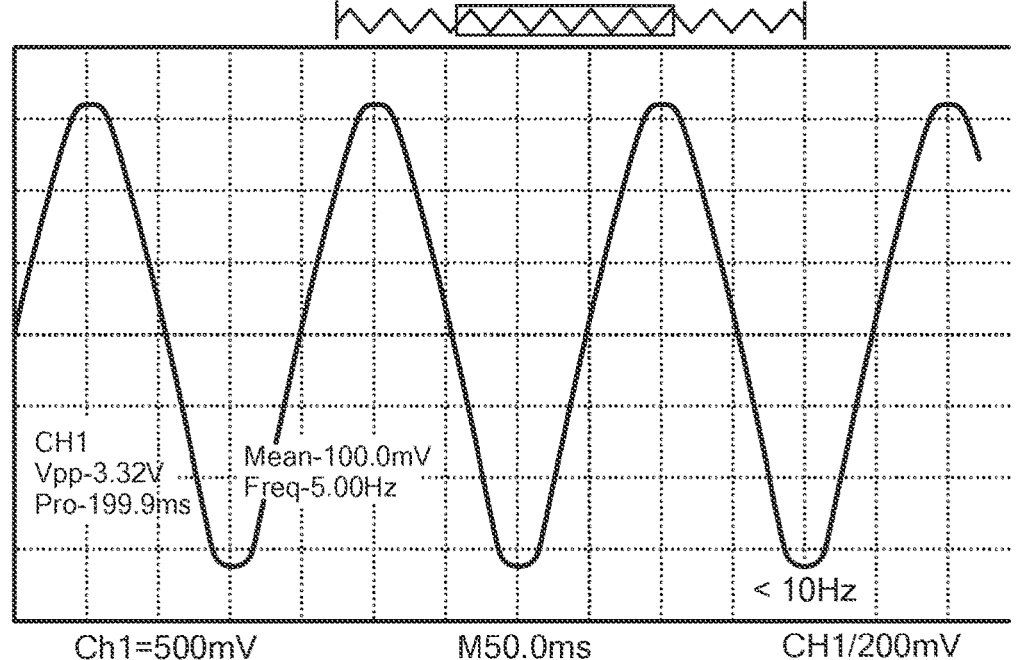
Figure 51C:
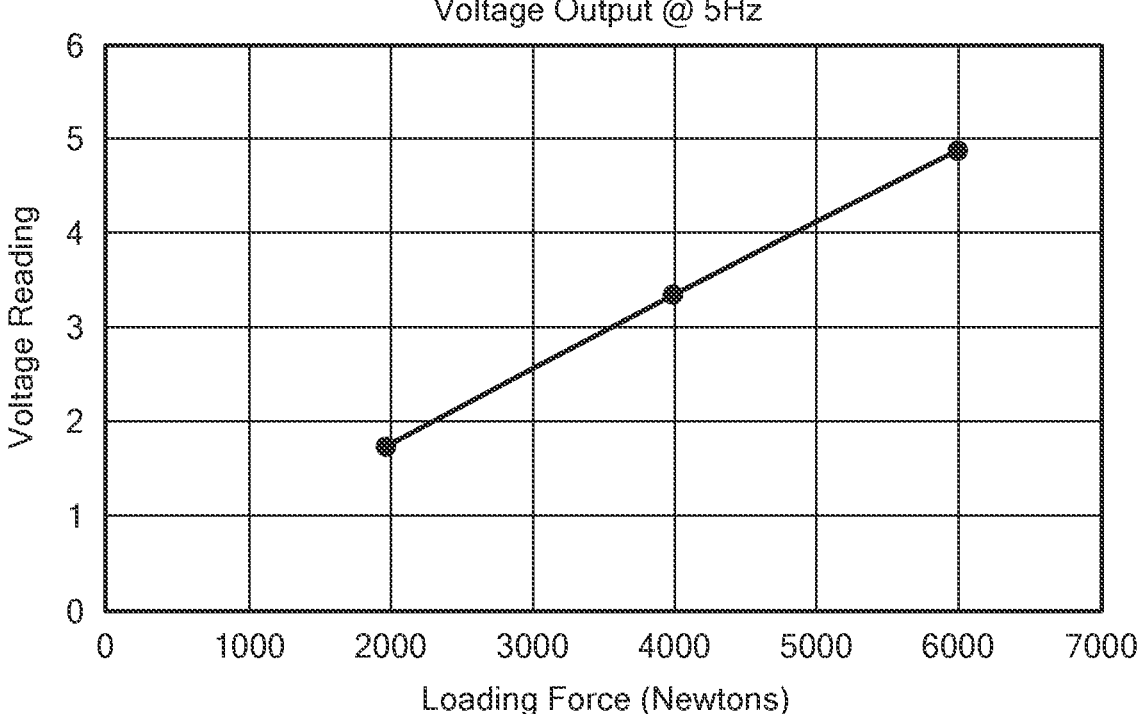

Referring now to FIGS. 51*a*, 51*b*, and 51*c*, a test configuration and test data of an embodiment of a piezoelectric spinal implant is shown. FIG. 51*a* shows a test configuration of an embodiment of a piezoelectric spinal implant inside of a mechanical testing machine, with an electrode 5102 on the top endplate and a ground lead 5104 on the bottom endplate. The endplates may undergo compressive and/or shear force. FIGS. 51*b* and 51*c* show results of a test in which electrical output is measured at the same frequency as the mechanical load—the voltage output measured is linearly correlated with the loading force.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the invention are to be understood as being in every respect illustrative and exemplary, but not restrictive, and the scope of the invention disclosed herein is not to be determined only from the detailed description of illustrative implementations but according to the full breadth permitted by patent laws. It is to be understood that the implementations shown and described herein are only illustrative of the principles of the present invention and that various modifications may be implemented by those skilled in the art without departing from the scope and spirit of the invention.

What is claimed is:

1. A spinal implant assembly comprising:
   a first endplate having a first non-planar inner surface;

a second endplate attached to the first endplate and having a second non-planar inner surface facing toward the first non-planar inner surface; and
   a component made entirely of a piezoelectric material, the component disposed between the first non-planar inner surface and the second non-planar inner surface and having a non-planar upper surface facing toward the first non-planar inner surface and a non-planar lower surface facing toward the second non-planar inner surface, wherein the first non-planar inner surface has first undulations and the second non-planar inner surface has second undulations, the first undulations including a first concave surface and a first convex surface, the first concave surface and the first convex surface together defining a first wavelike surface, the second undulations including a second concave surface and a second convex surface, the second concave surface and the second convex surface together defining a second wavelike surface.

2. The spinal implant assembly of claim 1, wherein the piezoelectric material includes a piezoelectric polymer.

3. The spinal implant assembly of claim 2, wherein the piezoelectric polymer includes polyvinylidene difluoride.

4. The spinal implant assembly of claim 1, wherein the first undulations and the second undulations are defined in a longitudinal direction of the spinal implant assembly and conform to one another, the first undulations and the second undulations to distribute compressive forces or shear forces applied to the first endplate and to the second endplate unevenly to the component.

5. The spinal implant assembly of claim 1, wherein the non-planar upper surface of the component conforms to and is adjacent to the first non-planar inner surface, and the non-planar lower surface of the component conforms to and is adjacent to the second non-planar inner surface.

6. The spinal implant assembly of claim 4, wherein the first undulations and the second undulations are further defined in a lateral direction of the spinal implant assembly.

7. The spinal implant assembly of claim 1, wherein the first endplate, the second endplate and the component are configured such that the first endplate and the second endplate are to cause a compressive force and a shear force on the component, at least one of the compressive force or the shear force to be distributed unevenly throughout the component.

8. The spinal implant assembly of claim 7, wherein the first endplate has a first outer surface and second endplates has a second outer surface, and wherein the component is configured to produce an electrical output corresponding to a load applied to the first outer surface and to the second outer surface.

9. The spinal implant assembly of claim 1, wherein the component is a first component, the piezoelectric material is a first piezoelectric material, the non-planar upper surface is a first non-planar upper surface, and the non-planar lower surface is a first non-planar lower surface, the spinal implant assembly further comprising:
   a second component including a second piezoelectric material the second component disposed between the first non-planar inner surface and the second non-planar inner surface and having a second non-planar upper surface facing toward the first non-planar inner surface and a second non-planar lower surface facing toward the second non-planar inner surface; and
   an intermediate body having a non-planar intermediate body top surface and a non-planar intermediate body bottom surface, the intermediate body disposed between the first component and the second component.

10. The spinal implant assembly of claim 9, wherein:

the first non-planar upper surface conforms to and is adjacent to the first non-planar inner surface, and the first non-planar lower surface conforms to and is adjacent to the non-planar intermediate body top surface of the intermediate body; and the second non-planar upper surface conforms to and is adjacent to the non-planar intermediate body bottom surface of the intermediate body, and the second non-planar lower surface conforms to and is adjacent to the second non-planar inner surface.

11. The spinal implant assembly of claim 9, wherein the intermediate body includes an electrically insulating material.

12. The spinal implant assembly of claim 1, further comprising at least one fastener connecting the first endplate and the second endplate to one another.

13. The spinal implant assembly of claim 12, wherein:

the first endplate defines a first lumen therein and a plurality of first holes through sides thereof;

the second endplate defines a second lumen therein and a plurality of second holes through sides thereof; and said at least one fastener includes:

a plurality of connecting brackets extending within the first lumen and the second lumen, each of the plurality of connecting brackets defining a top hole therein and a bottom hole therein, the top hole in registration with corresponding ones of the plurality of first holes, and the bottom hole in registration with corresponding ones of the plurality of second holes;

a plurality of top pins, respective ones of the plurality of top pins extending through the top hole of a corresponding one of said each of the plurality of connecting brackets and through corresponding ones of the plurality of first holes; and a plurality of bottom pins, respective ones of the plurality of bottom pins extending through the bottom hole of a corresponding one of said each of the plurality of connecting brackets and through corresponding ones of the plurality of second holes.

14. The spinal implant assembly of claim 13, wherein the plurality of connecting brackets include an electrically insulating material.

15. The spinal implant assembly of claim 13, wherein individual ones of the plurality of connecting brackets have flat side surfaces and rounded top and bottom ends.

16. The spinal implant assembly of claim 13, wherein the plurality of first holes, the plurality of second holes, the top hole of said each of the plurality of connecting brackets, the bottom hole of said each of the plurality of connecting brackets, the plurality of top pins, and the plurality of bottom pins have a cylindrical configuration.

17. The spinal implant assembly of claim 13, wherein the plurality of connecting brackets includes two connecting brackets spaced from one another in a longitudinal direction of the spinal implant assembly.

18. The spinal implant assembly of claim 12, wherein:

the first endplate defines a plurality of threaded first holes therein extending vertically;

the second endplate defines a plurality of threaded second holes therein extending vertically, respective ones of the plurality of threaded second holes in registration with respective corresponding ones of the plurality of threaded first holes to form respective threaded vertical fastener holes; and said at least one fastener includes a plurality of screws, respective ones of the plurality of screws extending through and engaging threads of respective ones of the threaded vertical fastener holes.

19. The spinal implant assembly of claim 18, wherein the plurality of screws include lag screws.

20. The spinal implant assembly of claim 18, wherein:

the first endplate has a first outer surface including first protrusions thereon, and the second endplate has a second outer surface including second protrusions thereon, the first protrusions and the second protrusions including at least one of teeth or spikes; and the plurality of screws include respective heads at a vertical distance below a topmost portion of the first protrusions.

21. The spinal implant assembly of claim 18, the plurality of screws including two screws spaced from one another in a longitudinal direction of the spinal implant assembly.

22. The spinal implant assembly of claim 1, wherein the first endplate has a first outer surface including first protrusions thereon, and the second endplate has a second outer surface including second protrusions thereon, the first protrusions and the second protrusions including at least one of teeth or spikes.

23. The spinal implant assembly of claim 1, wherein the component includes a plurality of distinct layers, wherein at least one of the distinct layers includes the piezoelectric material.

24. The spinal implant assembly of claim 1, wherein the first undulations extend across an entirety of the first inner surface, and the second undulations extend across an entirety of the second inner surface.

25. The spinal implant assembly of claim 1, wherein the second wavelike surface conforms to the first wavelike surface.

26. A kit to make a spinal implant assembly, the kit comprising:

a first endplate having a first non-planar inner surface;

a second endplate having a second non-planar inner surface, the first endplate and the second endplate configured to be attached to one another to form the spinal implant assembly; and a component made entirely of a piezoelectric material, the component to be disposed between the first non-planar inner surface and the second non-planar inner surface in the spinal implant assembly, the component further configured to a have, when part of the spinal implant assembly, a non-planar upper surface facing toward the first non-planar inner surface and a non-planar lower surface facing toward the second non-planar inner surface, wherein the first non-planar inner surface has first undulations and the second non-planar inner surface has second undulations, the first undulations including a first concave surface and a first convex surface, the first concave surface and the first convex surface together defining a first wavelike surface, the second undulations including a second concave surface and a second convex surface, the second concave surface and the second convex surface together defining a second wavelike surface.

27. The kit of claim 26, wherein the first undulations and the second undulations are defined in a longitudinal direction of corresponding ones of the first endplate and of the second endplate, and configured to conform to one another, and wherein, in the spinal implant assembly, the non-planar upper surface of the component conforms to and is adjacent to the first non-planar inner surface, and the non-planar lower surface of the component conforms to and is adjacent to the second non-planar inner surface.

28. The kit of claim 26, further comprising at least one fastener to connect the first endplate and the second endplate to one another to form the spinal implant assembly.

29. The kit of claim 28, wherein:

the first endplate defines a first lumen therein and a plurality of first holes through sides thereof;

the second endplate defines a second lumen therein and a plurality of second holes through sides thereof; and said at least one fastener includes:

a plurality of connecting brackets configured to extend within the first lumen and the second lumen, each of the plurality of connecting brackets defining a top hole therein and a bottom hole therein, the top hole configured to be in registration with corresponding ones of the plurality of first holes in the spinal implant assembly, and the bottom hole configured to be in registration with corresponding ones of the plurality of second holes in the spinal implant assembly;

a plurality of top pins, respective ones of the plurality of top pins configured to extend through the top hole of a corresponding one of said each of the plurality of connecting brackets and through corresponding ones of the plurality of first holes; and a plurality of bottom pins, respective ones of the plurality of bottom pins configured to extend through the bottom hole of a corresponding one of said each of the plurality of connecting brackets and through corresponding ones of the plurality of second holes.

30. The kit of claim 28, wherein:

the first endplate defines a plurality of threaded first holes therein extending vertically;

the second endplate defines a plurality of threaded second holes therein extending vertically, respective ones of the plurality of threaded second holes to be, in the spinal implant assembly, in registration with respective corresponding ones of the plurality of threaded first holes to form respective threaded vertical fastener holes; and said at least one fastener includes a plurality of screws, respective ones of the plurality of screws to extend through and to engage threads of respective ones of the threaded vertical fastener holes in the spinal implant assembly.

31. A method of making a kit for a spinal implant assembly, the method comprising:

forming a first endplate having a first non-planar inner surface;

forming a second endplate having a second non-planar inner surface, the first endplate and the second endplate configured to be attached to one another to form the spinal implant assembly;

forming a component made entirely of a piezoelectric material, the component to be disposed between the first non-planar inner surface and the second non-planar inner surface in the spinal implant assembly, the component further configured to a have, when part of the spinal implant assembly, a non-planar upper surface facing toward the first non-planar inner surface and a non-planar lower surface facing toward the second non-planar inner surface, wherein the first non-planar inner surface has first undulations and the second non-planar inner surface has second undulations, the first undulations including a first concave surface and a first convex surface, the first concave surface and the first convex surface together defining a first wavelike surface, the second undulations including a second concave surface and a second convex surface, the second concave surface and the second convex surface together defining a second wavelike surface; and organizing the first endplate, the second endplate, and the component together for joint provision as a kit for subsequent assembly into the spinal implant assembly.

32. The method of claim 31, wherein at least one of providing the first endplate or providing the second endplate includes using 3D printing.

* * * * *